United States Patent
Zhi

(10) Patent No.: US 10,449,210 B2
(45) Date of Patent: Oct. 22, 2019

(54) PRODRUG COMPOUNDS AND THEIR USES

(71) Applicant: LIGAND PHARMACEUTICALS, INC., San Diego, CA (US)

(72) Inventor: Lin Zhi, San Diego, CA (US)

(73) Assignee: LIGAND PHARMACEUTICALS INC., San Diego, CA (US)

( * ) Notice: Subject to any disclaimer, the term of this patent is extended or adjusted under 35 U.S.C. 154(b) by 86 days.

(21) Appl. No.: 15/118,821

(22) PCT Filed: Feb. 11, 2015

(86) PCT No.: PCT/US2015/015496
§ 371 (c)(1),
(2) Date: Aug. 12, 2016

(87) PCT Pub. No.: WO2015/123352
PCT Pub. Date: Aug. 20, 2015

(65) Prior Publication Data
US 2017/0056429 A1    Mar. 2, 2017

Related U.S. Application Data

(60) Provisional application No. 61/939,615, filed on Feb. 13, 2014, provisional application No. 61/988,101, filed on May 2, 2014, provisional application No. 61/988,118, filed on May 2, 2014.

(51) Int. Cl.
| | |
|---|---|
| *A01N 43/04* | (2006.01) |
| *A61K 31/70* | (2006.01) |
| *A61K 31/7072* | (2006.01) |
| *C07F 9/655* | (2006.01) |
| *C07F 9/6571* | (2006.01) |
| *C07F 9/6574* | (2006.01) |
| *C07F 9/6584* | (2006.01) |
| *C07F 9/09* | (2006.01) |
| *A61K 9/00* | (2006.01) |
| *A61K 31/661* | (2006.01) |
| *A61K 31/6615* | (2006.01) |
| *A61K 31/663* | (2006.01) |
| *A61K 31/675* | (2006.01) |

(52) U.S. Cl.
CPC ........ *A61K 31/7072* (2013.01); *A61K 9/0053* (2013.01); *A61K 31/661* (2013.01); *A61K 31/663* (2013.01); *A61K 31/6615* (2013.01); *A61K 31/675* (2013.01); *C07F 9/091* (2013.01); *C07F 9/098* (2013.01); *C07F 9/65515* (2013.01); *C07F 9/65744* (2013.01); *C07F 9/65746* (2013.01); *C07F 9/65842* (2013.01); *C07F 9/65844* (2013.01); *C07F 9/65846* (2013.01); *C07F 9/657154* (2013.01); *C07F 9/657181* (2013.01)

(58) Field of Classification Search
None
See application file for complete search history.

(56) References Cited

U.S. PATENT DOCUMENTS

| | | |
|---|---|---|
| 3,018,302 A | 1/1962 | Arnold et al. |
| 3,116,282 A | 12/1963 | Hunter |
| 3,328,388 A | 6/1967 | Shen et al. |
| 3,404,178 A | 10/1968 | Roy |
| 3,796,700 A | 3/1974 | Yoshioka et al. |
| 4,255,566 A | 3/1981 | Carrico et al. |
| 4,318,982 A | 3/1982 | Hornby et al. |
| 4,340,668 A | 7/1982 | Hornby et al. |
| 4,376,165 A | 3/1983 | Hornby et al. |
| 4,440,740 A | 4/1984 | Fix et al. |
| 4,447,529 A | 5/1984 | Greenquist et al. |
| 4,537,772 A | 8/1985 | Alexander et al. |
| 4,621,077 A | 11/1986 | Rosini et al. |
| 4,659,825 A | 4/1987 | Holy et al. |
| 4,692,441 A | 9/1987 | Alexander et al. |
| 4,705,651 A | 11/1987 | Staibano |
| 4,724,232 A | 2/1988 | Rideout et al. |
| 4,724,233 A | 2/1988 | DeClercq et al. |
| 4,729,989 A | 3/1988 | Alexander et al. |
| 4,731,360 A | 3/1988 | Alexander et al. |
| 4,749,694 A | 6/1988 | Fix et al. |
| 4,757,141 A | 7/1988 | Fung et al. |
| 4,777,163 A | 10/1988 | Bosies et al. |
| 4,804,655 A | 2/1989 | Müeller et al. |
| 4,808,716 A | 2/1989 | Holy et al. |
| 4,822,773 A | 4/1989 | Alexander et al. |
| 4,835,138 A | 5/1989 | Alexander et al. |
| 4,839,466 A | 6/1989 | Saltiel |
| 4,847,298 A | 7/1989 | Alexander et al. |
| 4,861,759 A | 8/1989 | Mitsuya et al. |
| 4,879,277 A | 11/1989 | Mitsuya et al. |
| 4,882,142 A | 11/1989 | Simon et al. |
| 4,898,724 A | 2/1990 | Simon et al. |

(Continued)

FOREIGN PATENT DOCUMENTS

| | | |
|---|---|---|
| CH | 492 738 | 6/1970 |
| DE | 1693219 A | 9/1970 |

(Continued)

OTHER PUBLICATIONS

Das, U. N. "Biological significance of essential fatty acids." Journal-Association of Physicians of India 54, No. R (2006): 309.*

(Continued)

*Primary Examiner* — Patrick T Lewis
(74) *Attorney, Agent, or Firm* — Knobbe, Martens, Olson & Bear LLP

(57) ABSTRACT

Provided herein are prodrug compounds, their preparation and their uses, such as treating liver diseases or nonliver diseases via intervening in molecular pathways in the liver. Novel prodrug compounds of acid/alcohol derivatives such as phosphates, phosphonates, phosphonamidates, phosphoramidates, carboxylates, phenolates, and alkoxylates, their preparation and their uses are described. Some of the novel prodrug compounds described herein do not generate a vinyl keto reactive intermediate in the activation process. Another aspect includes the use of prodrugs to treat diseases that benefit from enhanced drug distribution to the liver and like tissues and cells.

12 Claims, No Drawings

(56) References Cited

U.S. PATENT DOCUMENTS

| | | |
|---|---|---|
| 4,939,130 A | 7/1990 | Jaeggi et al. |
| 4,952,575 A | 8/1990 | Sauerbier et al. |
| 4,952,740 A | 8/1990 | Juge et al. |
| 4,963,525 A | 10/1990 | Alexander et al. |
| 4,963,556 A | 10/1990 | Alexander et al. |
| 4,973,579 A | 11/1990 | Alexander et al. |
| 5,034,394 A | 7/1991 | Daluge |
| 5,047,533 A | 9/1991 | Reist et al. |
| 5,077,280 A | 12/1991 | Sommadossi et al. |
| 5,089,500 A | 2/1992 | Daluge |
| 5,118,672 A | 6/1992 | Schinazi et al. |
| 5,130,303 A | 7/1992 | Akiyama et al. |
| 5,130,427 A | 7/1992 | Alexander et al. |
| 5,142,051 A | 8/1992 | Holy et al. |
| 5,153,183 A | 10/1992 | Kawabe et al. |
| 5,157,027 A | 10/1992 | Biller et al. |
| 5,159,067 A | 10/1992 | Schinazi et al. |
| 5,204,355 A | 4/1993 | Zsadon et al. |
| 5,210,085 A | 5/1993 | Liotta et al. |
| 5,212,304 A | 5/1993 | Fung et al. |
| 5,240,946 A | 8/1993 | Kinney et al. |
| 5,246,937 A | 9/1993 | Hamden et al. |
| 5,258,538 A | 11/1993 | Fung et al. |
| 5,366,965 A | 11/1994 | Strein |
| 5,437,772 A | 8/1995 | De Castro et al. |
| 5,464,748 A | 11/1995 | Sommadossi et al. |
| 5,466,841 A | 11/1995 | Horrobin et al. |
| 5,480,875 A | 1/1996 | Isomura et al. |
| 5,514,798 A | 5/1996 | Bischofberger et al. |
| 5,532,225 A | 7/1996 | Reist et al. |
| 5,567,689 A | 10/1996 | Sommadossi et al. |
| 5,583,122 A | 12/1996 | Benedict et al. |
| 5,599,686 A | 2/1997 | DeFeo-Jones et al. |
| 5,627,164 A | 5/1997 | Glazier |
| 5,658,889 A | 8/1997 | Gruber et al. |
| 5,663,159 A | 9/1997 | Starrett, Jr. et al. |
| 5,665,386 A | 9/1997 | Benet et al. |
| 5,681,590 A | 10/1997 | Bechard et al. |
| 5,686,629 A | 11/1997 | Bischofberger et al. |
| 5,716,928 A | 2/1998 | Benet et al. |
| 5,719,303 A | 2/1998 | Yoshida et al. |
| 5,721,219 A | 2/1998 | Ingall et al. |
| 5,723,449 A | 3/1998 | Sommadossi et al. |
| 5,750,493 A | 5/1998 | Sommadossi et al. |
| 5,767,097 A | 6/1998 | Tam |
| 5,789,608 A | 8/1998 | Glazier |
| 5,814,639 A | 9/1998 | Liotta et al. |
| 5,840,716 A | 11/1998 | Ubasawa et al. |
| 5,854,231 A | 12/1998 | Camden |
| 5,866,679 A | 2/1999 | DeFeo-Jones et al. |
| 5,866,684 A | 2/1999 | Attwood et al. |
| 5,869,467 A | 2/1999 | Holy et al. |
| 5,914,331 A | 6/1999 | Liotta et al. |
| 5,948,750 A | 9/1999 | Garsky et al. |
| 5,962,440 A | 10/1999 | Sulsky |
| 5,962,522 A | 10/1999 | Wacher et al. |
| 5,990,093 A | 11/1999 | Schinazi et al. |
| 6,004,927 A | 12/1999 | Benet et al. |
| 6,028,054 A | 2/2000 | Benet et al. |
| 6,037,335 A | 3/2000 | Takashima et al. |
| 6,045,638 A | 4/2000 | Lundstrom |
| 6,054,587 A | 4/2000 | Reddy et al. |
| 6,110,903 A | 8/2000 | Kasibhatla et al. |
| 6,117,873 A | 9/2000 | Acklin et al. |
| 6,121,234 A | 9/2000 | Benet et al. |
| 6,128,582 A | 10/2000 | Wilson et al. |
| 6,130,326 A | 10/2000 | Ramasamy et al. |
| 6,130,504 A | 10/2000 | Nakayama et al. |
| 6,143,715 A | 11/2000 | Llinas-Brunet et al. |
| 6,143,864 A | 11/2000 | DeFeo-Jones et al. |
| 6,177,404 B1 | 1/2001 | DeFeo-Jones et al. |
| 6,180,666 B1 | 1/2001 | Wacher et al. |
| 6,194,390 B1 | 2/2001 | Lori et al. |
| 6,194,391 B1 | 2/2001 | Schinazi et al. |
| 6,211,201 B1 | 4/2001 | Granger et al. |
| 6,245,749 B1 | 6/2001 | Schinazi et al. |
| 6,284,748 B1 | 9/2001 | Dang et al. |
| 6,294,672 B1 | 9/2001 | Reddy et al. |
| 6,312,662 B1 | 11/2001 | Erion et al. |
| 6,348,587 B1 | 2/2002 | Schinazi et al. |
| 6,372,883 B1 | 4/2002 | Attwood et al. |
| 6,391,305 B1 | 5/2002 | Feng et al. |
| 6,395,716 B1 | 5/2002 | Gosselin et al. |
| 6,395,763 B1 | 5/2002 | Stamos et al. |
| 6,399,773 B1 | 6/2002 | Liu et al. |
| 6,399,782 B1 | 6/2002 | Kasibhatla et al. |
| 6,403,566 B1 | 6/2002 | Wang |
| 6,407,077 B1 | 6/2002 | Gosselin et al. |
| 6,423,695 B1 | 7/2002 | Tam et al. |
| 6,444,652 B1 | 9/2002 | Gosselin et al. |
| 6,448,281 B1 | 9/2002 | Beaulieu et al. |
| 6,455,508 B1 | 9/2002 | Ramasamy et al. |
| 6,458,773 B1 | 10/2002 | Gosselin et al. |
| 6,486,204 B2 | 11/2002 | Waldstreicher et al. |
| 6,489,476 B1 | 12/2002 | Dang et al. |
| 6,495,677 B1 | 12/2002 | Ramasamy et al. |
| 6,518,253 B1 | 2/2003 | Tam |
| 6,525,033 B1 | 2/2003 | Schinazi et al. |
| 6,545,007 B2 | 4/2003 | Sommadossi et al. |
| 6,566,344 B1 | 5/2003 | Gosselin et al. |
| 6,569,837 B1 | 5/2003 | Gosselin et al. |
| 6,596,700 B2 | 7/2003 | Sommadossi et al. |
| 6,602,664 B2 | 8/2003 | Schinazi et al. |
| 6,608,027 B1 | 8/2003 | Tsantrizos et al. |
| 6,608,067 B1 | 8/2003 | Tung et al. |
| 6,613,896 B1 | 9/2003 | Ramasamy et al. |
| 6,635,636 B1 | 10/2003 | Artico et al. |
| 6,653,295 B2 | 11/2003 | Glunz et al. |
| 6,727,267 B2 | 4/2004 | Jaen et al. |
| 6,752,981 B1 | 6/2004 | Erion et al. |
| 6,756,360 B1 | 6/2004 | Erion et al. |
| 6,767,991 B1 | 7/2004 | Llinas-Brunet et al. |
| 6,777,395 B2 | 8/2004 | Bhat et al. |
| 6,784,166 B2 | 8/2004 | Devos et al. |
| 6,809,101 B2 | 10/2004 | Fujishita et al. |
| 6,846,810 B2 | 1/2005 | Armstrong et al. |
| 6,864,244 B2 | 3/2005 | Connolly et al. |
| 6,867,284 B1 | 3/2005 | Matassa et al. |
| 6,911,428 B2 | 6/2005 | Zhu et al. |
| 6,914,054 B2 | 7/2005 | Sommadossi et al. |
| 6,946,115 B2 | 9/2005 | Erion et al. |
| 6,994,959 B1 | 2/2006 | Tam |
| 7,081,449 B2 | 7/2006 | Pietrzkowski et al. |
| 7,091,209 B2 | 8/2006 | Gardelli et al. |
| 7,094,768 B2 | 8/2006 | Roberts et al. |
| 7,094,770 B2 | 8/2006 | Watanabe et al. |
| 7,105,493 B2 | 9/2006 | Sommadossi et al. |
| 7,148,349 B2 | 12/2006 | Reddy et al. |
| 7,151,092 B2 | 12/2006 | Boyer et al. |
| 7,169,766 B2 | 1/2007 | Sommadossi et al. |
| 7,193,081 B2 | 3/2007 | Kopcho et al. |
| 7,205,404 B1 | 4/2007 | Erion et al. |
| 7,214,668 B2 | 5/2007 | Erion et al. |
| 7,261,704 B2 | 8/2007 | Tachikawa et al. |
| 7,303,739 B2 | 12/2007 | Erion et al. |
| 7,351,399 B2 | 4/2008 | Erion et al. |
| 7,429,572 B2 | 9/2008 | Clark |
| 7,491,794 B2 | 2/2009 | Blatt et al. |
| 7,498,320 B2 | 3/2009 | Reddy et al. |
| 7,553,826 B2 | 6/2009 | Boyer et al. |
| 7,582,758 B2 | 9/2009 | Martin |
| 7,608,600 B2 | 10/2009 | Storer et al. |
| 7,666,855 B2 | 2/2010 | Reddy et al. |
| 7,816,345 B2 | 10/2010 | Erion et al. |
| 8,003,625 B2 | 8/2011 | Matteucci et al. |
| 8,063,025 B2 | 11/2011 | Hecker et al. |
| 8,080,536 B2 | 12/2011 | Erion et al. |
| 8,236,820 B2 | 8/2012 | Rigas |
| 8,664,195 B2 | 3/2014 | Erion et al. |
| 9,326,991 B2 | 5/2016 | Zhi et al. |
| 2001/0041713 A1 | 11/2001 | Waldstreicher et al. |
| 2002/0115596 A1 | 8/2002 | Garsky et al. |
| 2002/0120130 A1 | 8/2002 | Gosselin et al. |
| 2002/0147160 A1 | 10/2002 | Bhat et al. |

(56) References Cited

U.S. PATENT DOCUMENTS

| | | |
|---|---|---|
| 2002/0187945 A1 | 12/2002 | Tam |
| 2002/0193415 A1 | 12/2002 | LaColla et al. |
| 2003/0008841 A1 | 1/2003 | Devos et al. |
| 2003/0050229 A1 | 3/2003 | Sommadossi et al. |
| 2003/0050320 A1 | 3/2003 | Hashimoto et al. |
| 2003/0060400 A1 | 3/2003 | LaColla et al. |
| 2003/0083306 A1 | 5/2003 | Imbach et al. |
| 2003/0087873 A1 | 5/2003 | Stuyver et al. |
| 2003/0229225 A1 | 12/2003 | Reddy et al. |
| 2003/0232760 A1 | 12/2003 | Garsky et al. |
| 2004/0006002 A1 | 1/2004 | Sommadossi et al. |
| 2004/0006007 A1 | 1/2004 | Grosselin et al. |
| 2004/0014696 A1 | 1/2004 | Lau et al. |
| 2004/0019232 A1 | 1/2004 | Hostetler et al. |
| 2004/0063651 A1 | 4/2004 | Morioka et al. |
| 2004/0063658 A1 | 4/2004 | Roberts et al. |
| 2004/0067877 A1 | 4/2004 | Schinazi et al. |
| 2004/0077563 A1 | 4/2004 | Lau et al. |
| 2004/0147464 A1 | 7/2004 | Roberts et al. |
| 2004/0266723 A1 | 12/2004 | Otto et al. |
| 2005/0031588 A1 | 2/2005 | Sommadossi et al. |
| 2005/0054645 A1 | 3/2005 | Miyazaki et al. |
| 2005/0075309 A1 | 4/2005 | Storer et al. |
| 2005/0090463 A1 | 4/2005 | Roberts et al. |
| 2005/0101775 A1 | 5/2005 | Erion et al. |
| 2005/0101776 A1 | 5/2005 | Gosselin et al. |
| 2005/0107312 A1 | 5/2005 | Keicher et al. |
| 2005/0182252 A1 | 8/2005 | Reddy et al. |
| 2005/0282782 A1 | 12/2005 | Martin |
| 2006/0030545 A1 | 2/2006 | Cheng et al. |
| 2006/0046981 A1 | 3/2006 | Shibata |
| 2006/0234962 A1 | 10/2006 | Olsen et al. |
| 2007/0213588 A1 | 1/2007 | Reddy et al. |
| 2007/0032448 A1 | 2/2007 | Hong et al. |
| 2007/0060498 A1 | 3/2007 | Gosselin et al. |
| 2007/0179114 A1 | 8/2007 | Erion et al. |
| 2007/0183706 A1 | 8/2007 | Huang |
| 2007/0203339 A1 | 8/2007 | Kopcho et al. |
| 2008/0009533 A1 | 1/2008 | Tino et al. |
| 2008/0125605 A1 | 5/2008 | Erion et al. |
| 2009/0209481 A1 | 8/2009 | Hecker et al. |
| 2010/0305060 A1 | 12/2010 | Hecker et al. |
| 2011/0009356 A1 | 1/2011 | Erion et al. |
| 2011/0098251 A1 | 4/2011 | Ebetino et al. |
| 2012/0039845 A1 | 2/2012 | Hecker et al. |
| 2012/0093729 A1 | 4/2012 | Erion et al. |
| 2013/0310395 A1 | 11/2013 | Dodd et al. |
| 2014/0142052 A1 | 5/2014 | Lehn et al. |
| 2017/0158725 A1 | 6/2017 | Zhi |
| 2018/0291050 A1 | 10/2018 | Zhi |

FOREIGN PATENT DOCUMENTS

| | | | |
|---|---|---|---|
| EP | 0002062 A | 5/1979 | |
| EP | 0072531 A | 2/1983 | |
| EP | 0072987 | 3/1983 | |
| EP | 0158057 A | 10/1985 | |
| EP | 0161955 | 11/1985 | |
| EP | 0180276 A1 | 5/1986 | |
| EP | 0261283 A | 3/1988 | |
| EP | 0338372 A2 | 10/1989 | |
| EP | 0353692 B1 | 2/1990 | |
| EP | 0481214 A | 4/1992 | |
| EP | 0632048 | 1/1995 | |
| GB | 987378 | 3/1965 | |
| GB | 2266525 A | 11/1993 | |
| GB | 2266527 A | 11/1993 | |
| JP | 62-195392 A2 | 8/1987 | |
| JP | 62-249996 A2 | 10/1987 | |
| JP | S63-60929 | 3/1988 | |
| JP | H06-293785 | 10/1994 | |
| JP | H08-508245 A | 9/1996 | |
| JP | H09241284 A | 9/1997 | |
| JP | 2004-504326 | 2/2004 | |
| JP | 2009-502743 | 1/2009 | |
| JP | 2010-535817 | 11/2010 | |
| JP | 2013-508459 | 3/2013 | |
| WO | WO 1990/008155 | 7/1990 | |
| WO | WO 1990/010636 | 9/1990 | |
| WO | WO 1993/019075 | 9/1993 | |
| WO | WO 1995/07287 | 3/1995 | |
| WO | WO 1995/007920 | 3/1995 | |
| WO | WO 1996/001267 | 1/1996 | |
| WO | WO 1997/003679 | 2/1997 | |
| WO | WO 1997/022614 | 6/1997 | |
| WO | WO 1997/049717 | 12/1997 | |
| WO | WO 1998/008458 | 3/1998 | |
| WO | WO 1998/009668 | 3/1998 | |
| WO | WO 1998/038888 | 9/1998 | |
| WO | WO 1998/039342 | 9/1998 | |
| WO | WO 1998/039343 | 9/1998 | |
| WO | WO 1998/039344 | 9/1998 | |
| WO | WO 1998/046630 | 10/1998 | |
| WO | WO 1999/004774 | 2/1999 | |
| WO | WO 1999/004908 | 2/1999 | |
| WO | WO 1999/036074 | 7/1999 | |
| WO | WO 1999/045016 | 9/1999 | |
| WO | WO 1999/047549 | 9/1999 | |
| WO | WO 2000/003998 | 1/2000 | |
| WO | WO 2000/009531 | 2/2000 | |
| WO | WO 2000/014095 | 3/2000 | |
| WO | WO 2000/038666 | 7/2000 | |
| WO | WO 2000/052015 | 9/2000 | |
| WO | WO 2001/027114 | 4/2001 | |
| WO | WO 2001/039724 | 6/2001 | |
| WO | WO 2001/045509 | 6/2001 | |
| WO | WO 2001/045642 | 6/2001 | |
| WO | WO 2001/092282 | 12/2001 | |
| WO | WO 2001/093383 | 12/2001 | |
| WO | WO 2002/000673 | 1/2002 | |
| WO | WO 2002/008241 | 1/2002 | |
| WO | WO 2002/015904 | 2/2002 | |
| WO | WO 2002/083126 | 10/2002 | |
| WO | WO 2003/014821 | 2/2003 | |
| WO | WO 2003/014822 | 2/2003 | |
| WO | WO 2003/026589 | 4/2003 | |
| WO | WO 2003/026675 | 4/2003 | |
| WO | WO 2003/034690 | 4/2003 | |
| WO | WO 2003/034709 | 4/2003 | |
| WO | WO 2003/037908 | 5/2003 | |
| WO | WO 2003/051881 | 6/2003 | |
| WO | WO 2003/051896 | 6/2003 | |
| WO | WO 2003/051897 | 6/2003 | |
| WO | WO 2003/051898 | 6/2003 | |
| WO | WO 2003/051899 | 6/2003 | |
| WO | WO 2003/052053 | 6/2003 | |
| WO | WO 2003/068244 | 8/2003 | |
| WO | WO 2004/002422 | 1/2004 | |
| WO | WO 2004/002999 | 1/2004 | |
| WO | WO 2004/003000 | 1/2004 | |
| WO | WO 2006/033709 | 3/2006 | |
| WO | WO 2007/020193 | 2/2007 | |
| WO | WO 2010/065760 | 6/2010 | |
| WO | WO 2010/105048 | 9/2010 | |
| WO | WO-2012158811 A2 * | 11/2012 | ............ C07H 19/20 |
| WO | WO 2015/123352 | 8/2015 | |

OTHER PUBLICATIONS

Ali et al. Anticancer Research (2012), vol. 32, pp. 2999-3006.*
Jordheim et al. Nature Reviews. Drug Discovery (2013), vol. 12, pp. 447-464.*
Vaccaro et al. Chem. Commun. (2009), pp. 1404-1406.*
Szymanska-Michalak et al. European Journal of Medicinal Chemistry (2016), vol. 115, pp. 41-52.*
International Search Report and Written Opinion dated Jul. 9, 2015, in corresponding PCT/US2015/015496.
Alarcon R.A., "Studies on the In Vivo Formation of Acrolein: 3-Hydroxy-propylmercapturic Acid as an Index of Cyclophosphamide (NSC-26271) Activation," Cancer Treat Rep. (1976) 60(4): 327-335.

(56) References Cited

OTHER PUBLICATIONS

Aleksiuk et al., "Proximal Intraannular Modifictions of Calix[4]arene via its Spirodienone Derivative", J Chem Soc Chem Commun. (1993) 1: 11-13.
Alexakis et al., "Reactivity and Diasteroselectivity of Grignard Reagents toward the Hydrazone Functionality in Toluene Solvent," J Org Chem. (1992) 57(17): 4563-4565.
Alexander et al., "Preparation of 9-(2-Phosphonomethoxyethyl) Adenine Esters as Potential Prodrugs," Collect. Czech. Chem. Commun., (1994) 59: 1853-1869.
Allison et al., "Immunosuppressive and other anti-rheumatic activities of mycophenolate mofetil", Agents Actions Suppl. (1993) 44: 165-188.
Amin et al., "1-Hydroxy-3-(methylpentylamino)-propylidene-1, 1-bisphosphonic Acid as a Potent Inhibitor of Squalene Synthase," Arznemittelforschung. (1996) 46(8): 759-762.
Anderson et al., "2-Chloro-4(R),5(R)-dimethyl-2-oxo-1,3,2-dioxphospholane, a new chiral derivatizing agent," J Org Chem (1984) 49(7): 1304-1305.
Anderson et al., "Cyclophosphamide and 4-Hydroxycyclophosphamide/ Aldophosphamide Kinetics in Patients Receiving High-Dose Cyclophosphamide Chemotherapy," Clin Cancer Res. (1996) 2: 1481-1487.
Annaert et al., "Transport, Uptake, and Metabolism of the Bis(pivaloyloxymethyl)-Ester Prodrug of 9-(2-Phosphonylmethoxyethyl) Adenine in an In Vitro Cell Culture System of the Intestinal Mucosa (Caco-2)," Pharm Res. (1997) 14(4): 492-496.
Anzenbacherová, et al., "In Vivo Study of the Effect of Antiviral Acyclic Nucleotide Phosphonate(R)-9-[2(phosphonomethoxy)propyl]adenine (PMPA, tenofovir) and Its Prodrug Tenofovir Disoproxil Fumarate on Rat Microsomal Cytochrome P450," Physiol Res. (2008) 57: 761-767.
Arnér et al., "Mammalian Deoxyribonucleoside Kinases," PharmaC Ther. (1995) 67(2): 155-186.
Arnold et al., "Über Beziehungen zwischen chemischer Konstitution und cancerotoxischer Wirkung in der Reihe der Phosphamidester des Bis -(γ-chloräthyl)-amins," Konstitution und Wirkung, (1961) 11(2a): 143-158.
Aso et al., "Synthesis of a new class of spin-labeled purine ribonucleosides and development of novel nucleophilic reaction to form 2,6,8-trifunctionalized purine derivatives," J Chem Soc Perkins Trans. (2000) 2: 1637-1638.
Atiq et al., "Treatment of Unresectable Primary Liver cancer with Intrahepatic Fluorodeoxyuridine and Mitomycin C Through an Implantable Pump," Cancer (1992) 69: 920-924.
Attanasi et al., "Syntheis of some phosphorus derivatives of cardanol", Phosphor Sulfur (1988) 35(1-2): 63-65.
Auberson et al., "N-Phosphoalkyl-5-Aminomethylquinoxaline-2,3-Diones: In Vivo Active Ampa and NMDA(Glycine) Antagonists," Bioorg Med Chem Lttr. (1999) 9(2): 249-254.
Ayral-Kaloustian et al., "Synthesis of Partially-Protected D-Frutofuranoses and D-Fructose-6-Phosphates", Carbohydrate Res. (1991) 214: 187-192.
Baker et al., "Microtiter Plate Assay for the Measurement of Glutathione and Gluthione Disulfide in Large Numbers of Biological Samples," Anal Biochem. (1990) 190: 360-365.
Ballatore et al., "Carboxylic Acid (Bio)Isosteres in Drug Design", Chem Med Chem (2013) 8: 385-395.
Balthazor et al. "Nickel-Catalyzed Arbuzov Reaction: Mechanistic Observation," J Org Chem. (1980) 45: 5425-5426.
Balzarini et al., "5-Phosphoribosyl 1-Pyrophossphate Synthetase converts the acyclic nucleoside Phosphonates 9-(3-Hydroxy-2-phosphonylmethoxypropyl)adenine and 9-(2-Phosphonyl-methoxyethyl)adenine directly to their antivirally active Diposphate derivatives", J Biol Chem. (1991) 266(14): 8686-8689.
Balzarini et al., "Activity of the (R)-enantiomers of 9-(2-phosphonylmethoxypropyl)-Adenine and 9-(2-phosphonylmethoxypropyl)-2,6-diamiopurine against Human Immunodeficiency Virus in Different Human Cell Systems" Biochem Biophys Res Commun. (1996) 219: 337-341.

Banker, G.S. et al, "Modern Pharmaceutics, 3ed.", Marcel Dekker, New York, 1996, pp. 451 and 596.
Barluenga et al., "β-Substituted Organolithium Compounds. New Reagents for Synthesis," J Org Chem. (1979) 44(26): 4798-4801.
Barluenga et al., "Reduction of 1,3-Diimines. A New and General Method of Synthesis of gamma-Diamines, beta-Amino Ketones, and Derivatives with Two and Three Chiral Centers," J Org Chem. (1983) 48(13): 2255-2259.
Barluenga et al., "Stereoselective Synthesis of 1,3-Amino Alcohols and 1,3-Amino Ketones," J Org Chem. (1992) 57(4): 1219-1223.
Beaucage et al.,"The Synthesis of Modified Oligonucleotides by the Phosphoramidite Approach and Their Applications,"Tetrahed. (1993) 49(28): 6123-6194.
Bedford et al., "Synthesis of Water-Soluble Prodrugs of the Cytotoxic Agent Combretastatin A4," Bioorg Med Chem Lett. (1996) 6(2): 157-160.
Beigelman et al., "New Syntheses of 2'-C-Methylnucleosides Starting from $D$-Glucose and $D$-Ribose," Carbohydrate Res. (1987) 166: 219-232.
Beilstein Registry 1028505, "2-phenoxy-6,6-diphenyl-[1,3,2]oxazaphosphinane 2-oxide", Beilstein Institute for Organic Chemistry, Frankfurt, Germany; Nov. 28, 1988, 2 pages.
Beilstein Registry 1083232, "2-phenoxy-4-phenyl-<1,3,2>diazaphosphinane", Beilstein Institute for Organic Chemistry, Frankfurt, Germany, Nov. 29, 1988; 1 page.
Beilstein Registry 1085700, "3-mehtyl-2-phenoxy-6-phenyl-[1,3,2]diazaphosphinane 2-oxide", Beilstein Institute for Organic Chemistry, Frankfurt, Germany, entry date Nov. 29, 1988, in 1 page.
Beilstein Registry 6530655, "2-phenoxy-6,6-diphenyl-[1,3,2]oxazaphosphinane 2-oxide", Beilstein Institute for Organic Chemistry, Frankfurt, Germany, Apr. 18, 1994, 2 pages.
Beilstein Registry No. 3635189, "carboxy-phosphonic acid; sodium salt", Beilstein Institute for Organic Chemistry, Frankfurt, Germany, Feb. 26, 1991, 31 pages.
Benhamou et al., "Safety and efficacy of adefovir dipivoxil in patients co-infected with HIV-1 and lamivudine-resistant hepatitis B virus: an open-label pilot study," Lancet. (2001) 358(9283): 718-23.
Bentrude et al., "Stereo- and Regiochemistries of the Oxidations of 2-Methoxy-5-tert-butyl-1,3,2-dioxaphosphorinanes and the Cyclis Methyl 3'5'-Phosphite of Thymidine by $H_2O$/ $I_2$ and $O_2$/AIBN to P-Chiral Phosphates. $^{17}O$ NMR Assignment of Phosphorus Configuration in the Diasteromeric Thymidine Cyclic Methyl 3'5'-Monophosphates," J Am Chem Soc. (1989) 111: 3981-3987.
Bentrude et al. "Conformation of Saturated Six-Membered-Ring Phosphorus Heterocycles. 2-Aryl-1,3,2lambda$^5$-oxazapphosphorinanes" J Am Chem Soc. (1988) 110: 7119-7127.
Bentrude et al. "Conformations of Saturated Six-Membered-Ring Phosphorus Heterocycles Related to Cyclophosphamide. NMR, X-ray, and Infrared Studies of 2-Methoxy-2-oxo-1,3,2-oxazaphosphorinane and 2-Thio-1,3,2-oxazaphosphorinane" J Am Chem Soc. (1986) 108: 6696-6675.
Benzaria et al., "Synthesis, in Vitro Antiviral Evaluation, and Stability Studies of Bis(S-acyl-2-thioethyl) Ester Derivatives of 9-[2-(Phosphonomethoxy)ethyl]adenine (PMEA) as Potential PMEA Prodrugs with Improved Oral Bioavailability," J Med Chem. (1996) 39(25): 4958-4965.
Berry et al., "High-Yield Preparation of Isolated Rat Liver Parenchyman Cells," J Cell Biol. (1969) 43: 506-520.
Bertocchio et al., "Additions nucléophiles des cétones sur les fonctions éthyléiques activés," Bull. Soc. Chim. Fr, 1962, fasciclue 7, 307: 1809-1813.
Bespalov et al., "Prologation of morphine analgesia by competitive NMDA receptor antagonist D-CPPene (SDZ EAA 494) in rats," Euro J Pharmacol. (1998) 351: 299-305.
Bhatia et al., A new approach to the Synthesis of Ether Phospolipids. Etc. Tetra Lttrs. (1987) 28(3): 271-274.
Bhongle et al., "Expedient and High-Yield Synthesis of Alkylphosphonyl Dichlorides Under Mild, Neutral Conditions: Reaction of Bis(Trimethylsilyl) Alkyl Phosphonates with Oxalyl Chloride/ Dimethylformamide," Synth Commun. (1987) 17(9-16): 1071-1076.

(56) References Cited

OTHER PUBLICATIONS

Bijsterbosch et al., "Disposition of the Acyclic Nucleoside Phosphonate (S)-9-(3-Hydroxy-2-Phosphonylmethoxypropyl) Adenine," Antimic Agt Chemother. (1998) 42(5): 1146-1150.
Bird et al., "Synthesis of Novel N-Phosphonoalkyl Dipeptide Inhibitors of Human Collagenase," J Med Chem. (1994) 73: 158-169.
Boddy et al., "Individual Variation in the Activation and Inactivation of Metabolic Pathways of Cyclophosphamide," J Nat Cancer Inst. (1992) 84(22): 744-748.
Borch et al.: "The Mechanism of Activation of 4-Hydroxgyclophosphamide," J Med Chem. (1987) 30: 427-431.
Borch et al., "Synthesis and Antitumor Properties of Activated Cyclophosphamide Analogues," J Med Chem. (1991) 34(10): 3044-3052.
Borch et al., "Synthesis, Activation and Cytotoxicity of Aldophosphamide Analogues," J Med Chem. (1991) 34(10): 3052-3058.
Boyd et al., "Synthesis and Antitumor Activity of Cyclophosphamide Analogues. 3. Preparation, Molecular Structure Determination, and Anticancer Screening of Racemic cis- and trans-4-Phenylcyclophosphamide," J Med Chem. (1980) 23(4): 372-375.
Boyer et al., "The Discovery of MB07133: A HepDirect® Prodrug of Cytarabine Monophosphate for the Treatment of Hepatocellular Carcinoma", Poster; Prospective, Boston, MA (May 2006); 1 page.
Boyer et al., "Synthesis and Characterization off a Novel Liver-Targeted Prodrug of Cytosine-1-beta-D-arabinofuranoside Monophosphate for the Treatment of Hepatocellular Carcinoma," J Med Chem (2006) 49: 7711-7720.
Braess et al. "Oral Cytarabine Ocfostate in Acute Myeloid Leukemia and non-Hodgkins's Lymphoma—Phase I/II Studies and Pharmacokinetics", Leukemia (1998) 12: 1618-1626.
Brain et al., "Modulation of P450-Dependent Ifosfamide Pharmacokinetics: a Better Understanding of Drug Activation In Vivo," British J Cancer 77(11): 1768-1776.
Brechbühler et al., "Die Reaktion von Carbonsäuren mit Acetalen des N,N-Dimethylformamids: eine Veresterungsmethode," Helvetica Chimica Acta (1965) 48(7): 1746-1771.
Brenna et al, "Affinity-Chromatography Purification of Alkaline Phosphatase from Calf Intestine," Biochem J., (1975) 151: 291-296.
Brill et al., "Arbuzov-like Dealkylation Reactions of Transition-Metal-Phosphite Complexes," Chem Rev (1984) 84(6): 577-585.
Brock et al., "Acrolein, the Causative Factor of Urotoxic Side-effects of Cyclophosphamide, Ifosfamide, Trofosfamide and Sufosfamide," Drug Res. (1979) 29(4): 659-661.
Bronson et al., "Synthesis and Antiviral Activity of Nucleotide Analogs Bearing the (S)-(3-hydroxy-2-phosphonylmethoxy)propyl Moiety Attached to Adenine, Guanine, and Cytosine," in *Nucleotide Analogues as Antiviral Agents*; (1989) Chapter 6, pp. 88-102.
Bronson et al., "Synthesis and Antiviral Activity of Phosphonylmethoxyethyl Derivatives of Purine and Pyrimidine Bases," in *Nucleotide Analogues as Antiviral Agents* (1989), ACS Symposium Series 401, American Chemical Society; Chapter 5, pp. 72-87.
Brown et al., "The Nucleophilic Displacement Route to Homochiral Arylphosphine Oxides," Tetrahedron, (1990) 46(13/14): 4877-4886.
Burrows et al., "Synthesis, Characterization, and Electrochemistry of a Series of Iron(II) Complexes Containing Self-Assembled 1,5-Diaza-3,7-diphosphabicyclo[3.3.1]nonane Ligands", Inorg Chem. (2009) 48(20): 9924-9935.
Campagne et al. "Synthesis of Mixed Phosphonate Diester Analogues of Dipeptides using BOP or PyBOP Reagents," Tetra Lttrs., (1993) 34(42): 6743-6744.
Campbell D.A., "The Synthesis of Phosphonate Esthers; An Extension of the Mitsunobu Reation," J Org Chem. (1992) 57(23): 6331-6335.
Canas et al., "Regioselective Ring Opening of Chiral Epoxyalcohols by Primary Amines," Tetrahedron Ltts. (1991) 32(47): 6931-6934.
Casara et al., "Synthesis of Acid Stable 5'-o-Fluorometer Phosphonates of Nucleosides," Bioorg Med Chem Lett. (1992) 2(2): 145-148.

Casteel et al., "Steric and Electronic Effects in the Aryl Phosphate to Arylphoshonate Rearrangement," Synthesis, (1991) 1999(9): 691-693.
Chabner et al., "Purification and Properties of Cytidine Deaminase from Normal and Leukemia Granulocytes", J Clin Invest. (1974) 53: 922-931.
Chabner B.A., "Cytidine Analogues", in *Cancer Chemotherapy. Principles and Practice*, Lippincott Williams & Wilkins (1990); Chapter 6; 154-179.
Chang et al., "Enhanced Cycophosphamide and Ifosfamide Activation in Primary Human Hepatocyte Cultures: Response to Cytochrome P-450 Inducers and Autoinduction by Oxazaphosphorines," Cancer Res. (1997) 57: 1946-1954.
Chen et al., "Intratumoral Activation and Enhanced Chemotheraputic Effect of Oxazaphosphorines following Cytochrome P-450 Gene Transfer: Development of a Combined chemptherapy/Cancer Gene Therapy Strategy," Cancer Res. (1995) 55: 581-589.
Chen et al. "Sensitization of Human Breast Cancer Cells to Cyclophosphamide and Ifosfamide by Transfer of al Liver Cytochrome P450 Gene," Cancer Res.(1996) 56: 1331-1340.
Chu et al., "A Regiospecific Synthesis of 1-Methylamino-6-fluoro-7-(4-methylpiperazin-1-yl)-1,4-dihydro-4-oxoquinoline-3-carboxylic Acid," J Het Chem. (1985) 22: 1033-1034.
Chu et al., "Chemistry and Antiviral Activities of Acyclonucleosides," J Het Chem. (1986) 23(2): 289-319.
Clarke et al., "Oxidative Metabolism of Cyclophosphamide: Identification of the Hepatic Monooxygenase Catalysts of Drug Activation," Cancer Res. (1989) 49: 2344-2350.
Coates et al., "Annelative Ring Expansion via Intramolecular [2+2] Photocycloaddition of α,β-Unsaturated γ-Lactones and Reductive Cleavage: Synthesis of Hydrocyclopentacyclooctene-5-carbontlates," J Org Chem. (1982) 47(19): 4005.
Cohen, S.S. "The Mechanisms of Lethal Action of Arabinosyl Cytosine (araC) and Arabinosyl Adenine (araA)", Cancer (1977) 40(1): 509-518.
Commercon et al., "Diastereoselective Chlorocyclofunctionalization of N-Allylic Trichloroacetamides : Synthesis of an Analogue and Potential Precursor of RP49532," Tetrahed Ltts. (1990) 31(27): 3871-3874.
Cooper et al., "Use of Carbohydrate Derivatives for Studies of Phosphorus Stereo-chemistry. Part II. Synthesis and Configurational Assignments of 1,-3,2-Oxathiaphosphrinan-2-ones and 1,3,2-Dioxaphosphorinan-2-thiones," J.C.S. Perkin I, (1974) 3/2422:1049-1052.
Coppi, et al., "Lewis Acid Mediated Condensation of Alkenols and Aldehydes. A Selective Synthesis of Tetrahydropyrans and Oxepanes," J Org Chem., (1988) 53(4): 911-913.
Corey et al., "Enantioselective and Practical Syntheses of R- and S-Fluoxetines," Tetra Lttrs. (1989) 30(39): 5207-5210.
Cullis, P.M., "The Stereochemical Course of Iodine-Water Oxidation of Dinucleoside Phosphite Triesters," J Chem Soc. Chem. Commun., No. 1, 1984, pp. 1510-1512.
Cundy K.C., "Clinical pharmacokinetics of the antiviral nucleotide analogues cidofovir and adefovir," Clin Pharmacokinet. (1999) 36(2): 127-143.
Cundy et al., "Oral formulations of adefovir dipivoxil: in vitro dissolution and in vivo bioavailability in dogs," J Pharm Sci. (1997) 86(12): 1334-1338.
Curran et al., "Thermolysis of Bis[2-[(trimethylsilyl)oxy]prop-2-yl]furoXan (TOP—furoxan). The First Practical Method for Intermolecular Cycloaddition of an in Situ Generated Nitrile Oxide with 1,2-Di- and Trisubstituted Olefins," J Am Chem Soc. (1985) 107(21): 6023-6028.
Dang et al., "A New Regio-Defined Synthesis of PMEA," Nucleosides & Nucleotides (1998) 17(8): 1445-1451.
Davis et al., "Effect of *Withania somnifera* on cyclophosphamide-induced urotoxicity," Cancer Lett. (2000) 148: 9-17.
Dearfield et al., "Analysis of the Genotoxicity of Nine Acrylate/Methacrylate Coumpounds in L5178Y Mouse Lymphoma Cells," Mutagen. (1989) 4: 381-393 (1989).
Dechant et al., "Ifosfamide/Mesna—A Review of its Antineoplastic Activity, Pharmacokinetic Properties and Therapeutic Efficacy in Cancer," Drugs (1991) 42(3), 428-467.

(56) References Cited

OTHER PUBLICATIONS

De Clercq et al., "A novel selective broad-spectrum anti-DNA virus agent," Nature (1986) 323: 464-467.
De Clercq et al., "Antiviral activity of phosphonylmethoxyalkyl derivatives of purine and pyrimidines.," Antiviral Res. (1987) 8(5-6): 261-272.
Deeks et al., "The Safety and Efficacy of Adefovir Diplvoxil, a Novel Anti-Human Immunodeficiency Virus (HIV) Therapy, in HIV-Infected Adults: A, Randomized, Double-Blind, Placebo-Controlled Trial," J Infect Dis. (1997) 176(6): 1517-1523.
DeLeve et al., "Cellular Target of Cyclophosphamide Toxicity in the Murine Liver: Role of Glutathione and Site of Metabolic Activation," Hepatol. (1996) 24(4): 830-837.
De Lombaert et al., "N-Phosphomomethyl Dipeptides and Their Phosphonate Prodrugs, a New Generation of Neutral Endopeptidase (NEP, EC 3.4.24.11) Inhibitors", J Med Chem. (1994) 37(4): 498-511.
De Lombaert et al., "Pharmacological profile of a Non-Peptidic Dual Inhibitor of Neutral Endopeptidase 24.11 and Endothelin-converting enzyme," Biochem Biophys Res Commun. (1994) 204(1): 407-412.
Denmark et al., "Asymmetric Electrophilic Amination of Chiral Phosphorus-Stabilized Anions" Tetrahedron (1992) 48(11): 2191-2208.
Desos et al., "Structure-Activity Relationships in a Series of 2(1H)-Quinolones Bearing Different Acidic Function in the 3-Position: 6,7-Dichloro-2(1H)-oxoquinoline-3-phosphonic Acid, a New Potent and Selective AMPA/Kainate Antagonist with Neuroprotective Properties," J Med Chem. (1996) 39(1): 197-206.
Desta et al., "Stereoselective Metabolism of Cisapride and Enantiomer-Enantiomer Interaction in Human Cytochrome P450 Enzymes: Major Role of CYP3A," J Pharmacol Exp Ther. (2001) 298(2): 508-520.
De Waziers et al., "Cytochrome P450 Isoenzymes, Epoxide Hydrolase and Glutathlone Transferases in Rat and Human Hepatic and Extrahepatic Tissues1," J Pharm Exp Ther., (1990) 253(1): 387-394.
Dickson et al., "Orally Active Squalene Synthase Inhibitors: Bis((acyloxy)alkyl) Prodrugs of the alpha-Phosphonosulfonic Acid Moiety," J Med Chem. (1996) 39: 661-664.
Dornow et al., "Über einige Derivate der Benzoylessigsäure," in Chemische Berichte by C. Schöpf [Ed.], (1949) 82: 254-257.
Dyatkina et al., "Synthesis of the Four Possible Stereoisomeric 5'-Nor Carbocyclic Nucleosides from One Common Enantiomerically Pure Starting Material," Tetrahed Lttr. (1994) 35(13): 1961-1994.
Dymock, B.W., "Emerging Therapies for Hepatitis C Virus Infection," Expert Opin Emerg Drugs (2001) 6(1): 13-42.
Echizen et al., "Identifcation of CYP3A4 as the Enzyme Involved in the Mono-N-Dealkylation of Disopyramide Enantiomers in Humans," Drug Metab Dispos. (2000) 28(8): 937-944.
Edmunson et al., "Cyclic Organophosphorus Compounds, Part 23, Configurational Assignments in the 4-Phenyl-1.3,2lambd5-dioxaphosphorinane Series. X-Ray Molecular Structure of cis-2-Benzylamino-4-phenyl-1.3.2-dioxaphosphorinane 2-Oxide," J Chem Res Synop.(1989) 5: 122-123.
Eliel et al., "Oxygen-17 NMR Spectra of Cyclic Phosphites, Phosphates, and Tiophosphates", J Am Chem Soc. (1986) 108(21): 6651-6661.
Elliot et al., "Synthesis and Biological Evaluation of Phosphonamidate Peptide Inhibitors of Enkephalinas and Angiotensin-Converting Erwme," J Med Chem. (1985) 28(9): 1208-1216.
Enriquez et al., "Conjugation of Aadenine Arabinoside 5'-Monophosphate to Arabinogalactan: Cynthesis, Characterization, and Antiviral Activity," Bioconj Chem. (1995) 6(2): 195-202.
Erion et al. "HepDirectTM Prodrugs for Targeting Nucleotide-Based Antiviral Drugs to the Liver" Curr Opin Invest Drugs (2006) 7(2): 109-117.
Erion et al., "Design, Synthesis, and Characterization of a Series of Cytochrome P450 3A-Activated Prodrugs (HepDirect Prodrugs) Useful for Targeting Phosph(on)ate-Based Drugs to the Liver," J Am Chem Soc. (2004) 126(16): 5154-5163.

Erion et al., "Liver-Targeted Drug Delivery Using HepDirect Prodrugs" J Pharmacol Exper Ther. (2005) 312(2): 554-560.
Erion et al., "Liver-Targeted Nucleoside Prodrugs," presented at the Gordon Research Conference: Purines, Pyrimidines and Related Substances, Newport, RI (Jun.-Jul. 2003), 38 pages.
Erion et al., "HepDirect(TM) Prodrugs: A Novel Strategy for Targeting Drugs to the Liver," Hepatology (2002) 36(4-2): Abstract No. 551, p. 301A.
Erion et al., "Prodrugs phosphorus-containing compounds and pharmacodynamic action", retrieved from STN Database accession No. 2001:808252; 1 pages.
Erion et al., "Preparation of cyclic nucleotides as FBPase inhibitor prodrugs" retrieved from STN Database accession No. 1999:576934; 4 pages.
Evans "Chemistry 206 Advanced Organic Chemistry", Harvard University, [online] Sep. 11, 2003, [retrieved on Jan. 19, 2005]. Retrieved from the internet, <http://www.courses.fas.harvard.edu/~chem206/Fall-2003/Lectures-and-Handouts/>.
Evans et al., "New Procedure for the Direct Generation of Titanium Enolates. Diastereoselective Bond Constructions with Representative Electrophiles," J Am Chem Soc. (1998) 112(22): 8215-8216.
Evans et al., "Stereoselective Aldol Reactions of Chlorotitanium Enolates. An Efficient Method of the Assemblage of Polypropionate-Related Synthons," J Am Chem Soc. (1991) 113(3): 1047-1049.
Fang, C., et al. "Liver-Targeting Prodrug of PMEA Induces a Much More Favorable Kidney and Liver Toxicological Gene Expression-in Rats Compared to BisPOM-PMEA" Abstract #1274, 42nd Annual Meeting of the Society of Toxicology, Salt Lake City, UT (Mar. 9-13, 2003).
Fang, C., et al., "Renal Toxicological Gene Response to Anti-Hepatitis B Prodrugs Hepavir B and Hepsera in Rats" Abstract #1472, 43rd Annual Meeting of the Society of Toxicology, Baltimore, MD (Mar. 21-25, 2004).
Farquhar et al., "Synthesis and Antitumor Evaluation of Bis[(pivaloyloxy)methyl] 2'-Deoxy-5-fluorouridine 5'-Monophosphate (FdUMP): A Strategy to Introduce Nucleotides into Cells," J Med Chem. (1994) 37(23): 3902-3909.
Farquhar et al. "Biologically-Cleavable Phosphate Protective Groups: 4-Aclioxt-1,3,2-Dioxaphosphorinanes as Neutral Latent Precursors of Dianionic Phosphates," Tetra Lttrs. (1995) 36(5): 655-658.
Farquhar et al., "5'-[4-(Pivaloyloxy)-1,3,2-dioxaphosphorinan-2-yl]-2'-deoxy-5-fluorouridine: A membrane-permeating Prodrug of 5-fluoro-2'-damuridylic acid (FdUMP)", J Med Chem. (1995) 38(3): 488-495.
Farquhar et al., "Biologically Reversible Phosphate-Protective Groups," J Pharm Sci. (1983) 72(3): 324-325.
Farquhar et al., "Synthesis and Biological Evaluation of Neutral Derivatives of 5-Fluoro-2'deoxyuridine 5'-Phosphate," J Med Chem. (1983) 26(8): 1153-1158.
Farquhar et al., "Synthesis and Biological Evaluation of 9-[5'-(2-Oxo-1,3,2-oxazaphosphorinan-2-yl)-beta-D-arabinosyl]adenine and 9-[5'-(Oxo-1,3,2-dioxazaphosphorinan-2-yl)-beta-D-arabinosyl]adenine: Potential Neutral Precursors of 9-[-62 -D-Arabinofuranosyl]adenine 5'-Monophosphate," J Med Chem. (1985) 28(9): 1358-1361.
Ferroni et al., "A Three-step Preparation of Dihydroxyacetone Phosphate Dimethyl Acetal", J Org Chem. (1999) 64(13): 4943-4945.
Fiume et al., "Inhibition of Hepatitis B Virus replication by Vidarbine Monophosphate Conjugated with Lactosaminated Serum Albumin," The Lancet (1988) 2: 13-15.
Fraiser et al., "Murine strain differences in metabolism and bladder toxicity of cyclophosphamide," Toxicol. (1992)75: 257-272.
Freed et al., "Evidence for Acyloxymethyyl Esters of Pyridmidenc, 5'-Deoxyribonucleotides as extracellular sources of active 5'-deoxyribonucleotides in cultured cells," Biochem Pharmcol. (1989) 38(19): 3193-3198.
Freeman et al., "Prodrug Design for Phosphates and Phosphonates", Chapter 3; Prog Med Chem. (1997) 34: 111-147.
Freer et al., "A new route to famiciclovir via palladium catalysed allylation", Tetrahedron (2000) 56(26): 4589-4595.

(56) References Cited

OTHER PUBLICATIONS

Friis et al., "Prodrugs of Phosphates and Phosphonates: Novel Lipophilic alpha-acyloxyalkyl Ester Derivatives of Phosphate- or Phosphonate Containing Drugs Masking the Negative Charges of these Groups," Euro J Pharm Sci., (1996) 4: 49-59.
Fujii et al., "Ruthenium(II)-Catalyzed Asymmetric Transfer Hydrogenation of Ketones Using a Formic Acid-Triethylamine Mixture," J Am Chem Soc.(1996) 118: 2521-2522.
Furegati et al., "Stereochemistry of the Inhibition of alpha-Chymotrypsin with Optically Active cis-Decaline-Type Organophosphates: $^{31}$P-NMR Studies," Helvetica Chimica Acta (1998) 81: 1127-1138.
Gao et al., "Asymmetric Synthesis of Both Enantiomers of Tomoxetine and Fluoxetine. Seletive Reduction of 2,3-Epoxycinnamyl Alcohol with Red-Al," J Org Chem. (1988) 53(17): 4081-4084.
Gilard et al., "Chemical Stability and Fate of the Cytostatic Drug Ifosfamide and its N-Dechloroethylated Metabolites in Acidic Aqueous Solutions," J Med Chem. (1999) 42(14): 2542-2560.
Gilead Press Release, "Gilead Achieves Primary Endpoint in Phase III Study of Adefovir Dipivoxil for Chronic Hepatitis B Virus Infection," (2001); 3 pages.
Gish et al., "Nucleic Acids. 11. Synthesis of 5'-Esters of 1-beta-D-Arabinofuranosylcytosine Possessing Antileukemic and Immunosuppressive Activity", J Med Chem. (1971) 14(12): 1159-1162.
Gorenstein et al., "Stereoelectronic Effects in the Reactions of Epimeric 2-Aryloxy-2-oxy-1,3,2-dioxaphosphorinanes and Oxazaphosphorinanes," J Am Chem Soc. (1980) 102(15): 5077-5081.
Grant, S., "Biochemical Modulation of Cytosine Arabinoside", Pharmac Ther. (1990) 48: 29-44.
Greene et al., *Protective Groups in Organic Synthesis*, John Wiley, New York, 1999; (Toc only) 4 pages.
Groen et al., "Intracellular Compartmentation and Control of Alanine Metabolism in Rat Liver Parenchymal Cells," Eur J Biochem. (1982) 122: 87-93.
Guida et al., "Structure-Based Design of Inhibitors of Purine Nucleoside Phosphorylase. 4. A Study of Phosphate Mimics," J Med Chem. (1994) 37(8): 1109-1114.
Gurtoo et al., "Role of Glutathione in the Metabolism-dependent Toxicity and Chemotherapy of Cyclophosphamide," Cancer Res. (1981) 41: 3584-3591.
Gustin et al., "A Rapid, Sensitive Assay for Adenosine Deaminase," Anal Biochem. (1976) 71: 527-532.
Haddad et al., "Stereocontrolled Reductive Amination of 3-Hydroxy Ketones," Tetrahedron Ltts. (1997) 38(34): 5981-5984.
Hadváry et al., "Conformationally Restricted Analogs of Platelet-Activating Factor (PAF)", Helv Chim Acta 69(8): 1862-1871.
Hales et al., "Embryotoxicity of Phenyl Ketone Analogs of Cyclophosphamide," Teratology (1989) 39(1): 31-37.
Hammer et al., "Phosphorylation of the Nucelear Receptor SF-1 Modulates Cofactor Recruitment: Integration of Hormone Signaling in Reproduction and Stress", Mol Cell (1999) 3: 521-526.
Hanaoka et al., "Transformation of 2,3,9,10—tetraoxygenated protoberberine alkaloids into 2,3,10,11-tetracmgenated protoberberine alkaloids", Heterocycles (1985) 23(11): 2927-2930.
Hanson et al., "Regioselective enzymatic aminoacylation of Lobucavir to give an intermediate for Lobucavir prodrug," Biorg Med Chem. (2000) 8(12): 2681-2687.
Harada et al., "Resolution of 1,3-alkanediols Via Chiral Spiroketals Derivatives from iota-Menthone," Tetra Lttr. (1987) 28(41): 4843-4846.
Harry-O'Kuru et al., "A short, flexible route toward 2'-C-branchedribonucleosides", J Org Chem. (1997) 62(6): 1754-1759.
Hartung et al., "1,5-Diphosphabicyclo[3.3.1]nonane 1,5-Disulfide", Acta Cryst. (1988) C44: 1438-1440.
Hatse S., "Mechanistic study on the cytostatic and tumor cell differentiation-inducing properties of 9-(2-phosphonylmethoxyethyl)adenine (PMEA, adefovir)-collected publications," Verh K Acad Geneeskd Belg. (2000) 62(5): 373-384.

Hayakawa et al., "A General Approach to Nucleoside 3'- and 5'-Monophospates", Tetra Lttrs. (1987) 28(20): 2259-2262.
Hayakawa et al., "Benzimidazolium Triflate as an Efficient Promoter for Nucleotide Synthesis via the Phosphoramidite Method," J Org Chem. (1996) 61(23): 7996-7997.
He et al., "Inactivation of Cytochrome P450 3A4 by Bergamottin, a Component of Grapefruit Juice," Chem Res Toxicol. (1998) 11(4): 252-259.
Hecker et al., "Prodrugs of Phosphates and Phosphonates", J Med Chem. (2008) 51(8): 2328-2345; publ online Feb. 1, 2008.
Hessler E.J., "An Efficient Synthesis of 1-beta-D-Arabinofuranosylcytosine," J Org Chem. 41(10):1828-1831 (1976).
Hillers et al., "Analogs of pyrimidinemono- and polynucleotides. VI. Phosphates of 1-(1,4-dihydroxy-2-pentyl) thymine and 1-(1,3-dihydroxy-2-propyl)uracil", Chemical Abstracts by the American Chemical Society (1978) 89 (17): 607-608; Chemical Abstr. 146864u.
Hilton J., "Role of Aldehyde Dehydrogenase in Cyclophosphamide-resistant L1210 Leukemia," Cancer Res. (1984) 44: 5156-5160.
Hirayama et al., "Structure and conformation of a novel inhibitor of angiotensin I converting enzyme-a tripeptide containing phosphonic acid," Int J Pept Protein Res. (1991) 38: 20-24.
Ho et al., "Cytotoxicity of cytotoxicity of antiviral nucleotides adefovir and cidofovir is induced by the expression of human renal organic anion transporter 1", J Am Soc Nephrol. (2000) 11(3): 383-393.
Hoeffler et al., "Chemical Synthesis of Enantiopure 2-C-Methyl-D-Erythritol 4-Phosphate, the Key Intermediate in the Mevalonate-Independent Pathway for Isoprenoid Biosynthesis", Tetrahed. (2000) 56(11): 1485-1489.
Hoffman M., "A Simple, Efficient Synthesis of Dibenzyl and Di-p-nitrobenzyl 1-Hydroxyalkanephosphonates," Synthesis, J Synth Org Chem. (1988) 1: 62-64.
Holy et al., "Acyclic nucleotide analogues: synthesis, antiviral activity and inhibitory effects on some cellular and virus-encoded enzymes in vitro," Antiviral Res. (1990) 13(6):295-311.
Hong Z., "Hepavir B: a Safer and Liver-Targeting Prodrug of PMEA," Presented at the SRI-Antiviral Drug Discovery & Development Summit, Ribopharm Inc., Mar. 27, 2003; 19 pages.
Hong et al., "Clinical Update of Remofovir (Hepavir B): a Liver-targeting Prodrug of PMEA for the Treatment of Hepatitis B," Presented at the SRI-Antiviral Drug Discovery & Development Summit, Mar. 30, 2004; 23 pages.
Hori et al., "Palladium(II)-Catalyzed Asymmetric 1,3-Dipolar Cycloaddition of Nitrones to 3-Alkenoyl-1,3-oxazolidin-2-ones," J Org Chem. (1999) 64(14): 5017-5023.
Hughes D.L., "The Mitsunobu Reaction," Org React. (1992) vol. 42, Chapt. 2, pp. 335-656.
Hulst et al.: "A New $^{31}$P NMR Method for the Enantiomeric Excess Determination of Alcohols, Amines and Amino Acid Esters," Tetra Lttrs. (1993) 34(8): 1339-1342.
Hunston et al., "Synthesis and Biological Properties of Some Cyclic Phosphotriesters Derived from 2'Deoxy-5-fluorouride," J Med Chem. (1984) 27: 440-444.
Inanaga et al., "A Rapid Esterification by Means of Mixed Anhydride and its Application to Large-Ring Lactonization," Bull Chem Soc Jpn., (1979) 52(7): 1989-1993.
Iwata et al., "Asymmetric Functionalization at a Prochiral Carbon Center by the Aid of Sulfinyl Chirality: A Selective Formation of 6-Substituted (3R,Ss)—and (3S,Ss)-3-Hydroxymethyl-3,4-Dihydro-5-(p-Tolyl)Sulfinyl-2H-Pyrans," Tetra Lttrs. (1987) 28(27): 3131-3134.
Jacobsen et al., [Eds.] Comprehensive Asymmetric Catalysis—Catalysis I-III; Publisher: Springer (1999). (TOC only).
Jain et al., "Sulfonyl-Containing Aldophosphamide Analogues as Novel Anticancer Prodrugs Targeted against Cyclophosphamide-Resistant Tumor Cell Lines," J Med Chem. (2004) 47(15): 3843-3852.
Jones et al., "Minireview: nucleotide prodrugs", Antiviral Res. (1995) 27(1-2): 1-17.
Jones et al., "A Simple and Effective Method for Phosphoryl Transfer Using TiCl$_4$ Catalysis" Org. Lett. (2002) 4(21): 3671-3673.

(56) References Cited

OTHER PUBLICATIONS

Jounaidi et al., "Retroviral Transfer of Human Cytochrome P450 Genes for Oxazaphosphorine-based Cancer Gene Therapy," Cancer Res. (1998) 58(19): 4391-4401.

Jounaidi et al., "Frequent, Moderate-Dose Cyclophosphamide Administration Improves the Efficacy of Cytochrome P-450/Cytochrome P-450 Reductase-based Cancer Gene Therapy," Cancer Res. (2001) 61: 4437-4444.

Jung et al., "Hybridization of Alternating Cationic/Anionic Oligonucleotides to RNA Segments," Nucleosides and Nucleotides (1994) 13(6 & 7): 1597-1605.

Kachel et al., "Cyclophosphamide-Induced Lung Toxicity: Mechanism of Endothelial Cell Injury," J Pharmacol Exper Thera. (1994) 268(1): 42-46.

Keenan et al "Pathology Reevaluation of the Kociba et al. (1978) Bioassay of 2,3,7,8-TCDD: Implications for Risk Assessment," J Tox Envir Health (1991) 34: 279-296.

Kelley et al., "[[(Guaninylalkl) phosphinico]methyl]phosphonic Acids. Multisubstrate Analogue Inhibitors of Human Erythrocyte Purine Nucleoside Phosphorylase," J Med Chem. (1995) 38(6): 1005-1014.

Khamnei et al., "Neighboring Group Catalysis in the Design of Nucleotide Prodrugs," J Med Chem. (1996) 39(20): 4109-4115.

Khorana et al "Cyclic Phosphates. III. Some General Observations on the Formation and Properties of Five-, Six- and Seven-membered Cyclic Phosphate Esters," J Am Chem Soc. (1957) 79(2): 430-436.

Kim et al., "Synthesis and Biological Activities of Phosphonylalkylpurine Derivatives," Pharm. Res. Dev. (1989) 8(5-6): 927-931.

Kimura et al., "Studies on Nucleosides and Nucleotides. VII. 1) Preparation of Pyrimidine Nucleoside 5'-Phosphates and N3,5'-Purine Cyclonucleosides by Selective Activation of the 5'-Hydroxyl Group," Bull Chem Soc Jpn., (1979) 52(4): 1191-1196.

Kirschbaum, J., "Amantadine", Anal Prof Drug Subs. (1983) 12: 1-36.

Kirsten et al., "A General Strategy to Enantiomerically Pure Aliphatic and Olefinic Ketone Cyanohydrins by Stereoselective Alkylation of Umpoled Aldehyde Derivatives," J Org Chem. (1997) 62(20): 6882-6887.

Kobayashi et al., "Acylation of Active Methylene Compounds via Palladium Complex-Catalyzed Carbonylative Cross-Coupling of Organic Halides," Tetra Lttr., (1986) 27(39): 4745-4748.

Koh et al., "Design, Synthesis, and Antiviral Activity of Adenosine 5'-Phosphonate Analogues as Chain Terminators against Hepatitis C Virus", J Med Chem. (2005) 48(8): 2867-2875.

Korba et al., "Liver-targeted Antiviral Nucleosides: Enhanced Antiviral Activity of Phosphatidyl-dideoxyguanosine in Woodchuck Hepatitis Virus Infection in Vivo," Hepatol. (1996) 25(5): 958-963.

Kramata et al., "9-(2-Phosphonylmethoxyethyl) derivatives of purine nucleotide analogs: A comparison of their metabolism and interaction with cellular DNA synthesis", Mol Pharmacol. (1999) 56(6): 1262-1270.

Krise et al., "Prodrugs of phosphates, phosphonates, and phosphinates," Adv Drug Del Rev. (1996) 19(2): 287-310.

Kryuchkov et al., "Influence of Solvent on the Strength of Cyclic Oxygen-Containing Phosphorus Acids," Bull Acad Sci USSR, A translation of Izvestiya Akademii Nauk SSSR, Ser. Khim. (1987) 36(6) Part 1: 1145-1148.

Kuriyama et al., "Transient Cyclophosphamide Treatment Before Intraportal Readministration of an Adenoviral Vector can Induce Re-expression of the Original Gene Construct in Rat Liver," Gene Thera. (1999) 6: 749-757.

Kwon et al., "Effects of N-Substitution on the Activation Mechanisms of 4-Hydroxycyclophosphamide Analogues," J Med Chem. (1989) 32(7): 1491-1496.

Latour et al., "Simple Synthesis of 2-hydroxymethyl-1, 3-propanediol and related compounds", Synthesis, 1987, 8: 742-745.

Lau et al., "Safety, Tolerability, Pharmacokinetics and Pharmacodynamics of Remofovir in Chronic HBV Patients in USA and Canada Following Daily Dosing for 28 Days," Presented at the 40th Annual Meeting of EASL, Paris, France, J Hepatology 42(Suppl. 2)132, Abstract No. 74, Elsevier Ireland Ltd. (Apr. 2005).

Leach et al. "Toxicity Studies in Mice Treated with 1-β-D-Arabinofuranosyl-cytosine (ara-C)", Cancer Res. (1969) 29: 529-535.

Lefebvre et al., "Mononucleoside Phosphotriester Derivatives with S-acyl-2-thioethyl Bioreversible Phosphate-protecting Groups: Intracellular Delivery of 3'azido-2',3'dideoxythymidine 5'-monophosphate," J Med Chem. (1995) 38(20): 3941-3950.

Li et al., "Enantiomer/Enantiomer Interactions between the S-and R-Isomers of Omeprazole in Human Cytochrome P450 Enzymes: Major Role of CYP2C19 and CYP3A44," J Pharmacol Exp Ther. (2005) 315(2): 777-787.

Li et al., "Synthesis of D-arabinofuranosides Using Propane-1,3-diyl Phosphate as the Anomeric Leaving Group," Tetrahed Ltts. (2001) 42: 6615-6618.

Lilo et al., "Synthesis and Configurational Assignment of Bicyclic "Preactivated" Analogues of Cyclophosphamide," Tetra Lett. (1990) 31(6): 887-890.

Lin et al., "Comparative Disposition and Metabolic Profiles of [$^{14}$C]Remofovir and [$^{14}$C]Adefovir Dipivoxil in Rat Liver and Kidney," Abstracts of the 40th Annual Meeting of the European Association for the Study of the Liver, Paris, France, J Hepatology (2005) 42/2 Abstract #405.

Lin et al., "Development of Hepavir B, A Prodrug of PMEA with Excellent Liver-Targeting Properties," Abstracts of the 39th Annual Meeting of the EASL, Berlin, Germany, J Hapatology (2004) 40: Abs No. 374; p. 112.

Lin et al. "Single-Dose Pharmacokinetics and Metabolism of [$^{14}$C]Remofovir in Rats and Cynomolgus Monkeys" Antimicrobial Agents Chemother. (2005) 49(3): 925-930.

Lin et al., "Pradefovir is a Substrate, but Neither an Inhibitor nor an Inducer for Cytochrome P450," AASLD Abstracts, Hepatology (2005) 514A: Abstract No. 811; 1 page.

Lin et al., "Remofovir Mesylate: a Prodrug of PMEA with Improved Liver-Targeting and Safety in Rats and Monkeys," Antiviral Chem Chemother. (2004) 15: 307-316.

Lin et al., "Safety, Tolerance, Pharmacokinetics and Pharmacodynamics of Remofovir, A Liver-Targeting Prodrug of PMEA in HBV Patients Following Daily Dosing for 28 Days," AASLD Abstracts No. 1141, Hepatology(2004) 40(4 Suppl.): 659A; 2 pages.

Löhr et al., "Targeted chemotherapy by intratumor injection of encapsulated cells engineered to produce CYP2B1, and ifosfamide activating cytochrome P450," Gene Thera. (1998) 5: 1070-1078.

Lok et al., "Neurotoxicity associated with adenine arabinoside monophosphate in the treatment of chronic hepatitis B virus infection," J Antimicrob Chemother. (1984) 14: 93-99.

Lorey et al., "A New Cyclic Phosphoramidate D4T Prodrug Approach CycloAmb-D4T-Phosphoramidates," Nucleo Nucleo. (1999) 18(4 &5): 947-948.

Low et al., Conversion of 4-Hydroperoxycyclophosphamide and 4-Hydroxycyclophosphamide to Phosphoramide Mustard and Acrolein Mediated by Bifunctional Catalysts, Cancer Res. (1982) 42: 830-837.

Lown et al., "Grapefruit Juice Increases Felodipine Oral Availability in Humans by Decreasing Intestinal CYP3A Protein Expression," J Clin. Invest. (1997) 99: 2545-2553.

Lu et al., "Palladium-Catalyzed Reaction of Aryl Polyfluoroalkanesulfonates with O,O-Dialkyl Phosphonates", Synthesis (1987) 8: 726-727.

Ludeman et al., "Synthesis and Antitumor Activity of Cyclophosphamide Analogues. 1. Benzo Annulated Cyclophosphamide and Related Systems," J Med Chem. (1975) 18(12): 1251-1253.

Ludeman et al., "Synthesis and Antitumor Activity of Cyclophosphamide Analogues. 2. Preparation, Hydrolytic Studies, and Anticancer Screening of 5-Bromocyclophosphamide, 3,5-Dehydrocyclophosphamide, and Related Systems," J Med Chem. (1979) 22(2): 151-158.

Ludeman et al., "Synthesis and Antitumor Activity of Cyclophosphamide Analogues. 4. Preparation, Kinetic Studies, and Anticancer Screening of "Phenylketophosphamide" and Similar Compounds Related to the Cyclophosphamide Metabolite Aldophosphamide," J Med Chem. (1986) 29(5): 716-727.

(56) References Cited

OTHER PUBLICATIONS

Ludeman et al., "Synthesis of Reactive Metabolite-Analogues of Cyclophosphamide for Comparisons of NMR Kinetic Parameters and Anticancer Screening Data," Drugs Exptl Clin Res. (1986) XII(6/7): 527-532.

Ma et al., "A Phase I/II Study to Assess the Safety, Tolerability and Pharmacokinetics (PK) of Intravenous (IV) Infusion of MB07133 in Subjects with Unresectable Hepatocellular Carcinoma (HCC) (Poster ID 2054, No. 19)", Poster Presentation; American Society of Clinical Oncology (ASCO) Conference, Atlanta, Georgia (Jun. 2006); 1 page.

MacKenna et al., "MB07133: A HepDirect(TM) Prodrug of Cytarabine Monophosphate for Use in Hepatocellular Carcinoma," Hepatol. (2003) 38(Suppl. 1):411A, AASLD Abstract No. 524, 1 page.

March, J. [Ed], "Effects of Structure on Reactivity" in *Advanced Organic Chemistry*, McGraw Hill Book Company, New York, (1977 2nd Ed.); Chapter 9, pp. 251-259.

Martin et al., "Synthesis and Antiviral Activity of Various Esters of 9-[1,3-Dihydroxyl-2-proposy)methyl]guanine," J Pharma Scie. (1987) 76(2): 180-184.

Matsushima et al., "The nucleotide and deduced amino acid sequences of porcine liver proline-β- naphthylamidase," FEBS. (1991) 293(1-2): 37-41.

May-Manke et al., "Investigation of the Major Human Hepatic Cytochrome P450 Involved in 4-Hydroxylation and N-dechlorethylation of Trofosfamide," Cancer Chemother Pharmacol. (1999) 44: 327-334.

Maynard-Faure et al., "New Strategy for the Diastereoselective Synthesis of Bicyclic 'Pre-activiated' Analogues of Cyclophosphamide," Tetrahedron Lett. (1998) 39: 2315-2318.

McGuigan et al., "Intracellular Delivery of Bioactive AZT Nucleotides by Aryl Phosphate Derivatives of AZT," J Med Chem. (1993) 36(8): 1048-1052.

McGuigan et al., "Kinase Bypass: A new strategy for Anti-Hiv Drug Design," Bioorg Med Chem Lttrs. (1993) 3(6): 1207-1210.

Meek et al., "Synthesis of Inositol Phosphates", J Am Chem Soc. (1988) 110(7): 2317-2318.

Meier et al., "Cyclic Saligenyl Phosphotriesters of 2',3'-Dideoxy-2',3'-didehydrothymidine (d4T)—A New Pro-Nucleotide Approach," Bioorg Med Chem Lttrs. (1997) 7(2): 99-104.

Meier et al. "ADA-Bypass by Lipophilic cycloSal-ddAMP Pro-Nucleotides. A Second Example of the Efficiency of the cycloSal-Concept", Bioorg Med Chem Lett. (1997) 7(12): 1577-1582.

Meijer et al., "Covalent and Noncovalent Protein Binding of Drugs: Implications for Hepatic Clearance, Storage, and Cell-Specific Drug Delivery," Pharm Res. (1989) 6(2): 105-118.

Melvin, "An Efficient Synthesis of 2-Hydroxyphenylphosphonates," Tetra Lttrs. (1981) 22(35): 3375-3376.

Merckling et al., "Diastereoselectivity in Nucleophilic Displacement Reactions at Phosphorus; Isolation and Characterization of a Pentacoordinated Intermediate," Tetrahed Ltts. (1996) 37(13): 2217-2220.

Meyer et al., "2-O-Acyl-6-thioinosine Cyclic 3', 5'-Phosphates as Prodrugs of Thioinosinic Acid" , J Med Chem. (1979) 22(7): 811-815.

Mikolajczyk et al., "Dimethyl Selenoxide Oxidation of Trivalent Phosphorus Compounds, Thio- and Selenophosphoryl Compounds, and Thiocarbonyl Compounds. Stereochemical Studies and Selective Modification of the Thiocarbonyl-Containing Nucleic Acid Components," J Org Chem., (1978) 43(11): 2132-2138.

Misiura et al., "Synthesis and Antitumor Activity of Analogues of Ifosfamide Modified in the N-(2-Chloroethyl) Group," J Med Chem. (1987) 31(1): 226-230.

Mitchell et al., "Acetaminophen-Induced Hepatic Necrosis. IV. Protective Role of Glutathione," J Pharm Exp Thera. (1973) 187(1): 211-217.

Mitchell et al., "Bioreversible Protection for the Phospho Group: Bioactivation of the Di(4-acyloxybenzyl) and Mono(4-acyloxybenzyl) Phosphoesters of Methylphosphonate and Phosphonoacetate," J Chem Soc Perkin Trans. I. (1992) 2345-2353.

Mitsunobu, "The Use of Diethyl Azodicarboxylate and Triphenylphosphine in Synthesis and Transformation of Natural Products," Synthesis. (1981) 1981(1): 1-28.

Montag et al., "The Effect of Dexamethasone Treatment on CYP3A Activity Distribution, the Liver Targeting of MB07133 and CYP3A Activity in a Highly Proliferating State in Rats, " Hepatol. (2004) 40(Suppl. 1): 649A, AASLD Abstract No. 1123, 1 page.

Moore et al., "Comparison of Mutagenicity results for Nine Compounds evaluated at the hgprt Locus in the Standard and Suspension CHO Assays," Mutagenisis (1991) 6(1): 77-85.

Moriarty et al., "Diphenyl Methylphosphonate as a Phosphonylation Reagent with High Diastereoselectivity at Phosphorus," Tetrahedron Lett. (1997) 38(15): 2597-2600.

Mosbo et al. "Dipole Moment, Nuclear Magnetic Resonance, and Infrared Studies of Phosphorus Configurations and Equilibria in 2-R-2-Oxo-1,3,2-dioxaphosphorinanes," J Org Chem. (1977) 42(9): 1549-1555.

Mukaiyama, "The Directed Aldol Reaction", Org. React., (1982) 28: Chapter 3, pp. 203-251.

Mulato et al., "Nonsteroidal Anti-Inflammatory Drugs Effeciently Reduce the Transport and Cytotoxicity of Adefovir Mediated by the Human Renal Organic Anion Transporter 1," J Pharm Exp Ther. (2000) 295(1): 10-15.

Murono et al., "Prevention and inhibition of nasopharyngeal carcinoma growth by antiviral phosphonated nucleoside analogs," Cancer Res. (2001) 61(21): 7875-7877.

Murray et al., "Cytochrome P450 Expression is a common Molecular Event in Soft Tissue Sarcomas," J Phatol. (1993) 171: 49-52.

Murray et al., "Cytochrome P450 CYP3A in human renal cell cancer," Brit J Cancer (1999) 79(11/12): 1836-1842.

Naesens et al., "HPMPC (cidofovir), PMEA (adefovir) and Related Acyclic Nucleoside Phosphonate Analogues: A Review of Their Pharmacology and Clinical Potential in the Treatment of Viral Infections," Antiviral Chem Chemother., (1997) 8(1): 1-23.

Naesens et al., "Therapeutic Potential of HPMPC (Cidofovir), PMEA (Adefovir) and Related Acyclic Nucleoside Phosphonate Analogues as Broad-Spectrum Antiviral Agents," Nucleosides Nucleotides. (1997) 16(7-9): 983-992.

Nagamatsu et al., "New Phosphorylating Agents for General Synthesis of Mixed Phosphate Esters," Tetrahedron Lett. (1987) 28(21): 2375-2378.

Nakayama et al., "A Highly Enantioselective Synthesis of Phosphate Triesters," J Am Chem Soc. (1990) 112(19): 6936-6942.

Neidlein et al., "Mild Preparation of 1-Benzyloxyiminoalkylphosphonic Dichlorides: Application to the Synthesis of Cyclic Phosphonic Diesters and Cyclic Monoester Amides," Heterocycles (1993) 35(2): 1185-1203.

Nifant'Ev et al., et al., "Hexahydro-1,3,2,-Diazaphosphorines—II. Synthesis and Stereochemistry of Hexahydro-1,3-Dimethyl-1,3,4-Diazaphosphorines", J General Chemistry—USSR/Zh Obshch Khim., (1979) 49(1) Part 1: 53-61.

Nifantyev et al., "Synthesis and Structure of Some Stable Phospholane-Phospholanes," Phosphorus, Sulfur Silicon and Related Elements (1996) 113: 1-13.

Noble et al., "Adefovir Dipivoxil," Drugs. (1999) 58(3): 479-487.

Noyori et al., *Asymmetric Catalysis on Organic Synthesis*, (1994) John Wiley & Sons, Inc. (TOC only).

Ogg et al., "A reporter gene assay to assess the molecular mechanisms of xenobiotic-dependent induction of the human CYP3A4 gene in vitro," Xenobiotica (1999) 29(3): 269-279.

Ogilvie et al., A General Transesterification Method for the Synthesis of Mixed Trialkyl Phosphates, J Am Chem Soc. (1977) 99(1): 1277-1278.

Ohashi et al., "Synthesis of Phosphonosphingoglycolipid found in Marine Snail *Turbo Cornutus*," Tetra Lttrs. (1988) 29(10): 1189-1192.

Oliyai et al., "Kinetic Studies of the Degradation of Oxycarbonyloxymethyl Prodrugs of Adefovir and Tenofovir in Solution," Nucleosides, Nucleotides & Nucleic Acids, 20(4-7):1295-1298 (2001).

Ozaki et al, "Synthesis, Isolation and Characterization of Diastereochemically Pure Dithymidine Phosphormorpholidate Derivatives," Tetrahed Letts. (1989) 30(43): 5899-5902.

(56) References Cited

OTHER PUBLICATIONS

Ozaki et al., "Synthesis of Bis(deoxyribonucleoside) Phosphoromorpholidate Derivatives for Oligodeoxyribonucleotide Preparation by Use of a Selective Phosphitylating Reagent," Bull Chem Soc Jpn. (1989) 62(12): 3869-3876.
Ozoe et al., "Actions of cyclic esters, S-esters, and amides of phenyl-and phenylthiophosphonic acids on mammalia and insect GABA-gated chloride channels," Bioorg Med Chem. (1998) 6(1): 73-83.
Paine et al., "The Human Intestinal Cytochrome P450 'Pie'," Drug Metab Dispos. (2006) 34(5): 880-886.
Pankiewicz et al., "Nucleosides", J Org Chem. (1985) 50(18): 3319-3322.
Patois et al., "2-alkyl-5,5-dimethyl-1,3,2-dioxaphosphorinan-2-ones alpha-lithiated carbanions", J Chem Soc Perkin Trans. 1; (1990) 6: 1577-1581.
Patois et al., "Easy preparation of alkylphosphonyl dichlorides," Bull Soc Chim Fr. (1993) 130: 485-487.
Perich et al., "Di-tert-butyl N,N-Diethylphosphoramidite. A New Phosphitylating Agent for the Efficient Phosphorylation of Alcohols," Snthesis (1988) 1: 142-144.
Perich et al., "Synthesis of Casein-Related Peptides and Phosphopepties. V* The Efficient Global Phosphorylation of Protected Serine Derivatives and Peptides by Using Dibenzyl or Di-t-butyl N,N-Diethylphosphoramidite," Aust J Chem. (1990) 43(7-12): 1623-1632.
Perrillo et al., "A Multicenter United States—Canadian Trial to Assess Lamivudine Monotherapy before and after Liver Transplantation for Chronic Hepatitis B", Hepatol. (2001) 33(2): 424-432.
Petrakis et al., "Palladium-Catalyzed Substitutions of Triflates Derived from Tyrosine-Containing Peptides and Simpler Hydroxyarenes Forming 4-(Diethoxyphosphinyl) phenylalanines and Diethyl Arylphosphonates", J Am Chem Soc. (1986) 109(9): 2831-2833.
Pettit et al., "Antineoplastic agents 322. Synthesis of combretastatin A-4 prodrugs*," Anti-Cancer Drug Design. (1995) 10: 299-309.
Pilcher, "Built-In bypass," Nature (2004) 429: 39.
Plunkett et al. "Pharmacologically Directed Ara-C Therapy for Refractory Leukemia", Semin Oncol. (1985) 12(2) Supp. 3: 20-30.
Pogatchnik et al., "Enantioselective Synthesis of α-Hydroxy Phosphonates via Oxidation with (Camphorsulfonyl)oxaziridines," Tetrahedron Lett. (1997) 38(20): 3495-3498.
Posner et al., "3-Bromo-2-Pyrone: An Easily Prepared Chameleon Diene and a Synthetic Equivalent of 2-Pyrone in Thermal Diels-Alder Cucloadditions," Tetrahed Letts. (1991) 32(39): 5295-5298.
Postel et al., "Autocleavage of O-Isopropylidene Protected O-Phosphono- and O-Thionophosphono Esters of Sugars", J Carbohyd Chem. (2000) 19(2): 171-192.
Predvoditelev et al., "Glycero-2-hydroxymethylene phosphates" J Org Chem.—USSR (1977) 13(8) Part1: 1489-1492.
Predvoditelev et al., "Synthesis of lipids and their models on the basis of glycerol alkylene phosphites. V. Cyclic phosphatidylglycerol and phosphatidylhydrcwhomocholine" J Org Chem.—USSR (1981) 17(6) Part 2: 1156-1165.
Prisbe et al., "Synthesis and Antiherpes Virus Activity of Phosphate and Phosphonate Deriviates of 9-[(1,3-Dihydorzy-2-propoxy)methyl]guanine", J Med Chem (1986) 29: 671-675.
Pubchem. SID 22395163; online: Feb. 23, 2007; NIH U.S. National Library of Medicine, [retrieved on Aug. 25, 2015]; 9 pages.
Quast et al., "Herstellung von Methylphosphonsäure-dichlorid," Synthesis, International Journal of Methods in Synthetic Organic Chemistry, 1974, p. 490.
Ramachandran et al., "Efficient General Synthesis of 1,2- and 1,3-diols in High Enantiomeric Excess via the Intramolecular Asymmetric Reduction of the Corresponding Ketoalkyl Diisopinocampheylborinate Intermediates," Tetra. Lttr. (1997) 38(5): 761-764.
Ramu et al., "Acrolein Mercapturates: Synthesis, Characterization, and Assessment of Their Role in the Bladder Toxicity of Cyclophosphamide," Chem Res TaxicoL. (1995) 8(4): 515-524.
Rao et al., "Studies Directed Towards the Synthesis of Immunosuppressive Agent FK-506 : Synthesis of the Entire Top-Half," Tetrahedron Letts. (1991) 32(4): 547-550.
Rathore et al., "Synthesis of aryl dichlorophospates using phase transfer catalysts", Indian J Chem B. (1993) 32(10): 1066-1067.
Rautio et al., "Prodrugs: design and clinical applications", Nature Rev Drug Disc. (2008) 7: 255-270.
Reddy et al., "Stereoselective Synthesis of Nucleoside Monophosphate HepDirect™ Prodrugs," Tetra Lttrs. (2005) 46: 4321-4324.
Reddy et al., "Development of a Quantum Mechanics-Based Free-Energy Perturbation Method: Use in the Calculation of Relative Solvation Free Energies", J Am Chem Soc.(2004) 126(20): 6224-6225.
Reddy, K. Raja, et al., "Pradefovir (MB06866Q+): A Novel Hepatitis B Antiviral Therapy Using the HepDirect Prodrug Technology for Targeting Adefovir to the Liver," poster presented at the XVII International Roundtable on Nucleosides, Nucleotides and Nucleic Acids, Bern, Switzerland (Sep. 3-7, 2006).
Reddy, K. Raja, et al., "HepDirect™ Prodrugs of Adefovir: Design, Synthesis and Optimization," Abstract for 227th ACS National Meeting in Anaheim, CA (Mar. 28-Apr. 1, 2004).
Redmore, "Phosphorus Derivatives of Nitrogen Heterocycles. 2. Pyridinephosphonic Acid Derivatives," J Org Chem. (1970) 35(12): 4114-4117.
Ren et al., "Inhibition of Human Aldehyde Dehydrogenase 1 by the 4-Hydroxycyclophosphamide Degradation Product Acrolein," Drug Metabol Disp. (1999) 27(1): 133-137.
Ren et al., "PharmacokinetIcs of cyclophosphamide and its metabolites in bone marrow transplantation patients," Clinical Pharm Thera. (1998) 64(3): 289-301.
Reusch, William, "Virtual Text of Organic Chemistry," Michigan State University, [online] Aug. 1, 2004, [retrieved on Jan. 19, 2005]. Retrieved from the internet, <http://www.cem.msu.edu/%7Ereusch/VirtualText/speciall2.htm#topl>.
Robins et al., Design and synthesis of beta-D -ribofuranosyl nucleosides active against RNA viral infections, Adv Antiviral Drug Design. (1993) 1: 39-85.
Roodsari et al., "A new approach to the stereospecific synthesis of Phospholipids, etc.", J Org Chem. (1999) 64(21): 7727-7737.
Roy et al., "Development of a Substrate-Activity Based Approach to Identify the Major Human Liver P-450 Catalysts of Cyclophosphamide and Ifosfamide Activation Based on cDNA-Expressed Activities and Liver Microsomal P-450 Profiles," Drug Metab Dispos. (Mar. 1999) 27(6): 655-666.
Russell et al., "Determination of 9-[(2-phosphonylmethoxy)ethyl]adenine in rat urine by high-performance liquid chromatography with fluorescence detection," J Chromatogr. (1991) 572(1-2): 321-326.
Rustum et al. "1 β-Arabinofuranosylcytosine in Therapy of Leukemia: Preclinical and Clinincal Overview," Pharmac Ther. (1992) 56: 307-321.
Sakamoto et al., "The Palladium-Catalyzed Arylation of 4H-1,3-Dioxin," Tetra Lttrs. (1992) 33(45): 6845-6848.
Sartillo-Piscil et al., "Fosfato-ésteres ciclicos diastereoisomericos: 5-bromo-4-fenil-2-fenoxi-2-oxo-1,3,2-dioxafosforinanos, precursores de radicales libres alquilo β-fosfatoxi γ generadores de radicales cationicos en medio no oxidativo," Rev. Soc. Quim. Mexico 46(4): 330-334, Journal of the Mexican Chemical Society (Dec. 2002); English translation.
Schlachter et al., "Anti-Inflammatory/Antiarthritic Ketonic Bisphosphonic Acid Esters," Bioorg Med Chem. Lett. (1998) 8(9): 1093-1096.
Schultz, "Prodrugs of Biologically Active Phosphate Esters" Bioorg Med Chem. (2003) 11: 885-898.
Schultze et al., "Practical Synthesis of the anti-HIV Drug, PMPA" Tetrahedron Lett. (1998) 39(14): 1853-1856.
Schwartz et al., "Cyclophosphamide Induces Caspase 9-Dependent Apoptosis in 9L Tumor Cells," Mol Pharmacol. (2001) 60(6): 1268-1279.
Serafinowska et al., "Synthesis and in Vivo Evaluation of Prodrugs of 9-[2-(Phosphonomethoxy)ethoxy]adenine," J Med Chem. (1995) 38: 1372-1379.

(56) References Cited

OTHER PUBLICATIONS

Shan et al., "Prodrug Strategies Based on Intramolecular cyclization Reactions," J Pharm Sci. (1997) 86(7): 765-767.
Shaw et al., "Biological Screens of PMEA Prodrugs," Pharm Res. (1993) 10(10): S294, Contributed Papers Abstract No. PDD 7480.
Shaw et al., "Pharmacokinetics and Metabolism of Selected Prodrugs of PMEA in Rats," Drug Metabolism Dis. (1997) 25(3): 362-366.
Shen et al., "Nucleosides I. A New Synthesis of 1-β-D-Arabinofuranosyl Pyrimidine Nucleosides," J Org Chem. (1965) 30: 835-838.
Shih et al., "Preparation and Structures of 2-Dimethylamino-4-phenyl-1.3.2-dioxaphosphorinane-2-oxides," Bull Inst Chem Acad Sin. (1994) 41: 9-16.
Shih et al., "Synthesis and Structure of 6-Phenylcyclophosphamides," Heterocycles (1986) 24(6): 1599-1603.
Shih et al., "Studies on Potential Antitumor Agents (III). Synthesis of 4-Arylcyclophosphamides", Heterocycles (1978) 9(9): 1277-1285.
Shimada et al., "Interindividual Variations in Human Liver Cytochrome P-450 Enzymes Involved in the Oxidation of Drugs, Carcinogens and Toxic Chemicals: Studies with Liver Microsomes of 30 Japanes and 30 Caucasians," J Pharmacol Exp Ther. (1994) 270: 414-423.
Shimma et. al., "The Design and Sythesis of a New Tumor-Selective Fluoropyrimidine Carbamate, Capecitabine" Bioorg Med Chem. (2000) 8: 1697-1706.
Shirai et al., "Asymmetric Synthesis of Antimitotic CombretadioXolane with Potent Antitumor Activity Against Multi-Drug Resistant Cells," Bioorg Med Chem Lett (1998) 8: 1997-2000.
Shoshani et al., "Enzymatic synthesis of unlabeled and beta-32P-labeled beta-L-2',3'-dideoxyadenosine-5'-triphosphate . . . ", CAS Abstract Accession No. 1999:798820 in 2 pages.
Silverberg et al., "A simple, rapid and efficient protocol for the selective phosphorylation of phenols with dibenzyl phosphite", Tetrahedron Lttrs. (1996) 37(6): 771-774.
Sinicrope et al., "Modulation of P-glycoprotein-mediated Drug Transport by Alterations in Lipid Fluidity of Rat Liver Canalicular Membrane Vescicles", J Biol Chem. (1992) 267(36): 24995-25002.
Sladek et al. "Influence of Diuretics on Urinary General Base Catalytic Activity and Cyclophosphamide-Induced Bladder Toxixity", Canc Treat Repts. (1982) 65(11): 1889-1990.
Sladek et al., "Restoration of Sensitivity to Oxazaphosphorines by Inhibitors of Aldehyde Dehydrogenase Activity in Cultured Oxazaphosphorine-resistant L 1210 and Cross-Linking Agent-resistant P388 Cell Lines[1]," Canc Res. (1985) 45: 1549-1555.
Slowinski et al., "Highly Stereoselective Induction in the Cobald-mediated [2+2+2] Cycloaddition of Chiral Phosphine Oxides Substituted Linear Enediynes", Tetrahedron Ltts. (1999) 40: 5849-5852.
Smolarek et al., "Metabolism and cytotoxicity of acetaminopen in hepatocyte cultures from rat, rabbit, dog, and monkey", Drug Metab Dispos. (1989) 18(5): 659-663.
Springate et al. "Toxicity of Ifosfamide and It's Metaboline Chloroacetaldehyde in Cultured Renal Tubule Cells", In Vitro Cell Dev Biol.—Animal (1999) 35: 314-317.
Starrett et al., "Synthesis, Oral Bioavailability Determination, and in Vitro Evalution of Prodrugs of the Antiviral Agent 9-[2-(Phosphonomethoxy)ethyl]adenine (PMEA)," J Med Chem. (1994) 37(12): 1857-1864.
Stepanov et al., "Total Syntheses of Chiral sn-myo-Inositol-1,4,5-Trisphosphate and its Enantiomer," Tetrahedron Letts. (1989) 30(38): 5125-5128.
Still et al., "Direct Synthesis of Z-Unsaturated Esters. A Useful Modification of The Horner-Emmons Olefination," Tetrahedron LettS. (1983) 24(41): 4405-4408.
Stella V.J., "Prodrugs as Therapeutics", Expert Opin. Ther. Patents (2004) 14(3): 277-280.
Stowell et al., "The Mild Preparation of Synthetically Useful Phosphonic Dichlorides: Application to the Synthesis of Cyclic Phosphonic Diesters and Diamides," Tetrahedron Letts. (1990) 31(23): 3261-3262.

Strömberg et al, "Iodide and Iodine Catalysed Phosphorylation of Nucleosides by Phosphorodiester Derivatives," Nucleo Nucleo. (1987) 6(5): 815-820.
Sullivan-Bolyai et al., "Safety, Tolerability, Antiviral Activity, and Pharmacokinetics of Pradefovir Mesylate in Patients with Chronic Hepatitis B Virus Infection: 24-Week Interim Analysis of a Phase 2 Study," AASLD Program, Hepatol. (2005) 78A: Abstract No. LB 07.
Sumida et al., "Quantitative Analysis of Constitutive and Inducible CYPs mRNA Expression in the HepG2 Cell Line Using Reverse Transcription-Competitive PCR," Biochem Biophys Res Commun. (2000) 267(3): 756-780.
Suto et al. "The Effect of YNK-01 (an Oral Prodrug of Cytarabine) on Hepatocellular Carcinoma" Semin Oncol. (1997) 24(2) Suppl 6: S6-122 to S6-129.
Taapken et al., "Stereoselective Synthesis of Homochrial (E)-Vinyl Phosphonates Derived from (−)Ephedrine," Tetrahedron Letts. (1995) 36(37): 6659-6662.
Takaku et al., "Synthesis of Bis(5-chloro-8-quinolyl) Nucleoside 5'-Phosphates in Oligoribonucleotide Systhesis by the Phosphotriester Approach," J Org Chem. (1982) 47(25): 4937-4940.
Takaku et al., "Synthesis of Deoxyribooligonucleotides Using Cesium Fluoride by the Phosphotriester Approach," Nippon Kagaku Kaisha (1985) 10: 1968-1973, The Chemical Society of Japan, Inc.; English Translation.
Takaku et al., "Use of 2-(2-Pyridyl)Ethyl Group as a new Protecting Group of Internucleotidic Phosphates in Oligonucleotide Synthesis", Chem Lttrs. (1986) 5: 699-702.
Tawfik et al., "1,8-Diazabicyclo[5.4.0]undecene Mediated Transesterification of p-Nitrophenyl Phosphonates: A Novel Route to Phosphono Esters," Synthesis (1993) 10: 968-972.
ten Hoeve et al.: "The Design of Resolving Agents Chiral Cyclic Phosphoric Acids," J Org Chem. (1985) 50(23): 4508-4514.
Thomson et al., "Synthesis, Bioactivation and Anti-HIV Activity of the Bis(4-acyloxybenzyl) and Mono(4-acyloxybenzyl) Esters of the 5'-monophosphate of AZT," J Chem Soc. Perkin Trans. I. (1993) 2/06723D: 1239-1245.
Thuong et al., "Nouvelle méthode de préparation de la phosphorylcholine, de la phosphorylhomocholine et de leurs dérivés," Bull Soc Chim France, (1974) No. 130; 1-2: 667-671; English translation.
Torneiro et al., "A Short, Efficient, Copper-Mediated Synthesis of 1alpha, 25-Dihydroxyvitamin D2 (1alpha, 25-Dihydroxyergocalciferol) and C-24 Analogs", J Org Chem. (1997) 62(18): 6344-6352.
Tullis et al., "Reagent Control of Geometric Selectivity and Enantiotopic Group Preference in Asymmetric Horner-Wadsworth-Emmons Reactions with meso-Dialdehydes," J Org Chem. (1998) 63(23): 8284-8294.
Turner et al., "Acylation of Ester Enolates by N-Methoxy-N-methylamides: An Effective Synthesis of beta-Keto Esters", J Org Chem. (1989) 54(17): 4229-4231.
Turner J. A., "A General Appproach to the Synthesis of 1,6-,1,7-, and 1,8-Naphthyridines," J Org Chem. (1990) 55(15): 4744-4750.
Valentine Jr., "Preparation of the Enantiomers of Compounds Containing Chiral Phosphorus Centers," Asym Synth. (1984) 41: 263-312.
Van Haperen et al., "Induction of Resistance to 2',2'-Difluorodeoxycytidine in the Human Ovarian Cancer Cell Line A2780", Semin Oncol. 22 Suppl. (1995) 11(4): 35-41.
Van Poelje et al., "MB6866 (Hepavir B), A HepDirect™ Prodrug of Adefovir: Mechanism of Activation and Liver Targeting," AASLD Abstracts, Hepatology (2003) 706A:Abstract No. 1143.
Vankayalapati et al., "Stereoselective synthesis of alpha-L-Fucp-(1,2)- and -(1,3)-beta-D-Galp(1)-4-methylumbelliferone using glycosyl donor substituted by propane-1,3-diyl phosphate as leaving group", J Chem Soc Perkin Trans J. (2000) 14: 2187-2193.
Venook, "Treatment of Heptacellular Carcinoma: Too Many Options?" J Clin Oncol. (1994) 12(6): 1323-1334.
Verfürth et al., "Asymmetrische Synthese chiraler Phosphorverbindungen durch destruktiv-selektive Oxidation von P(III)-Verbindungen mittels chiraler Oxaziridine," Chem. Ber. (1991) 124(7): 1627-1634.

(56) References Cited

OTHER PUBLICATIONS

Vitarella et al. "Hepavir B, A CYP3A4-Activated Prodrug of PMEA, Showed Better Safety then Hepsera in Pre-Clinical Studies" Abstract #995 of the 43rd Annual Meeting of the Society of Toxicology, Baltimore, MD (Mar. 2004).
Vo-Quang et al., "(1-Amino-2-propenyl) Phosphonic Acid, and Inhibitor of Alanine Racemase and D-Alanine:D-Alanine Ligase.," J Med Chem. (1986) 29(4): 579-581.
Wacher et al., "Active Secretion and Enterocytic Drug Metabolism Barriers to Drug Absorption," Adv Drug Del Rev. (2001) 46: 89-102.
Wada et al., "Nucleoside 3'-N,N-Dialkyphosphonamidates: Novel Building Blocks for Oligonucleotide Synthesis," Tetrahedron Letts. (1990) 31(44): 6363-6366.
Waga et al., "Synthesis of 4'-C-Methylnucleosides", Biosci Biotech Biochem. (1993) 57(9): 1433-1438.
Wagner et al., "Direct Conversion of Tetrahydropyranylated Alcohols to the Corresponding Bromides," Tetra Lttrs. (1989) 30(5): 557-558.
Wallace et al., "Design and Synthesis of Potent, Selective Inhibitors of Endothelin-Converting Enzyme," J Med Chem (1998) 41(9): 1513-1523.
Walsh et al. "Phenoxymethylphosphonic Acids and Phosphonic Acid Ion-exchange Resins," J Am Chem Soc. (1956) 78: 4455-4458.
Watanabe et al., "Dibenzyl Phosphorofluoridate, A New Phosphorylating Agent," Tetrahedron Letts. (1988) 29(45): 5763-5764.
Watanabe et al, "A Short Step and Practical Synthesis of MYO-Inositol 1,3,4,5-Tetrakisphosphate," Chem Pharm Bull. (1990) 38(2): 562-563.
Watkins et al., "Noninvasive tests of CYP3A enzymes," Pharmacogenetics (1994) 4: 171-184.
Weber et al., "Activation of the Anti-cancer Drug Ifosphamide by Rat Liver Microsomal P450 Enzymes," Biochem Pharm. (1993) 45(8): 1685-1694.
Wechter et al., "Nucleic Acids, 16. Orally Active Derivatives of ara-Cytidine", J Med Chem. (1976) 19(8), 1013-1017.
Weibel et al., "Potentiating Effect of {2-[2-[(2-Amino-1,6-Dihydro-6-oxo-9H-Purin-9-yl)Methyl]-Phenyl]Ethenyl}-Phosphonic Acid (MDL 74,428), A Potent Inhibitor of Purine Nucleoside Phosphorylase, on the Antiretroviral Activities of 2',3''-Dideoxyinosine Combined to Ribavirin in Mice," Biochem Pharmacol. (1994) 48(2): 245-252.
Weinhardt et al., "Synthesis and antidepressant Profiles of Phenyl-Substituted 2-Amino- and 2-[(Alkoxycarbonyl)amino]-1,4,5,6-tetrahydropyrimidines[1]," J Med Chem. (1985) 28: 694-898.
Welch et al., "The Stereochemistry of the Aryl Phosphate/Aryl Phosphonate Rearrangement in 1,3,2-Oxazaphospholidine 2-Oxides," J Org Chem. (1990) 55(24): 5991-5995.
Werle et al., "Synthese der Dimethylolessigsäure," Liebigs. Ann. Chem., 1986, pp. 944-946.
Wileman et al., "Receptor-mediated endocytosis," Biochem J. (1985) 232: 1-14.
Wolfe et al., "A Concise Synthesis of 2'-C-Methylribonucleosides", Tetrahedron Lttrs. (1995) 36(42): 7611-7614.
Wolff M. E. [Ed] "Burger's Medicinal Chemistry and Drug Discovery, 5ed, Part I", John Wiley & Sons, 1995, pp. 975-977.
Woźniak et al., "Oxidation in Organophosphorus Chemistry: Potassium Peroxymonosulphate", Tetrahedron Letts. (1999) 40(13): 2637-2640.
Xu, C.R., et al. "Toxicokinetics of Adefovir Dipivoxil and Remofovir in 28-Day Toxicity Studies" Abstract #PB-P009 of the 64th International Congress FIP World Congress of Pharmacy and Pharmaceutical Science, New Orleans, LA (Sep. 2004).
Xu, C.R., et al., "Toxicokinetics of Remofovir in Mice, Rats and Monkeys After Repeated Oral Administrations" Abstract #PB-P008 of the 64th International Congress FIP World Congress of Pharmacy and Pharmaceutical Science, New Orleans, LA (Sep. 2004).
Yamakage et al., "1,1,1,3,3,3-Hexafluoro-2-Propyl Group as a New Phosphate Protection Group for Oligoribonucleotide Synthesis in the Phosphotriester Approach," Tetrahedron (1989) 45(17): 5459-5468.
Yamamoto et al., "Synthesis of Pyridine N-Oxide-SbC15 Complexes and Their Intramolecular and Oxygen-Transfer Reaction," Tetra Lttrs. (1981) 37: 1871-1873.
Yamanaka et al., "Metabolic Studies on BMS-200475, a New Antiviral Compound Active against Hepatitis B Virus", Antimicrob Agents Chemother. (1999) 43(1): 190-193.
Yip et al. "Use of High-Performance Liquid Chromatography in the Preparation of Flavin Adenine Dinucleotide Analyte Conjugates," J Chromatography (1985) 326: 301-310.
Yoshida et al., "Participation of the Peroxisomal β-Oxidation System in the Chain-Shortening of $PCA_{16}$, A Metabolite of the Cytosine Arabinoside Prodrug, YNKO1, in Rat Liver," Biochem Pharmacol. (1990) 39(10): 1505-1512.
Yu et al., "In Vivo Modulation of Alternative Pathways of P-450-Catalyzed Cyclophosphamide Metabolism: Impact on Pharmacokinetics and Antitumor Activity," J Pharm Exp Ther. (1999) 288(3): 928-937.
Yule et al., "The Effect of Fluconazole on Cyclophosphamide Metabolism in Children," Drug Metabo Disp. (1999) 27(3): 417-421.
Zhou et al., "IDX184, a liver-targeted Nucleotide HCV Polymerase Inhibitor: Results of a First-in-Man Safety and Pharmacokinetic Study", Poster No. 966; 44th Annual Meeting European Association for the Study of the Liver (EASL); Copenhagen, Denmark Apr. 22-26, 2009; 1 page.
Zon G., "Cyclophosphamide Analogues", *Progress Med Chem.* Ellis G.P. et al. [Eds] (1982) 19: 205-246.
Zon et al., "NMR Spectroscopic Studies of Intermediary Metabolites of Cyclophosphamide. A Comprehensive Kinetic Analysis of the Interconversion of cis- and trans-4-Hydroxycyclophosphamide with Aldophosphamide and Concomitant Partitioning of Adophosphamide Between Irreversible Fragmentation and Reversible Conjugation Pathways," J Med Chem. (1984) 27(4): 466-485.
Database Registry. Chemical Abstracts Service, Columbus, Ohio, US; STN Database Accession No. 1982:159892. XP002777344, 2 pages.
Database Registry. Chemical Abstracts Service, Columbus, Ohio, US; STN Database Accession No. 1996:144369, 1 page.
Database Registry. Chemical Abstracts Service, Columbus, Ohio, US; STN Database Accession No. 1996:204511; XP-002777346. 3 pages.
Database Registry, Chemical Abstracts Service, Columbus, Ohio, US; Sep. 28, 2008. XP002777347, retrieved from STN Database Accession No. 1053732-62-9; 1 page.
Database Registry, Chemical Abstracts Service, Columbus, Ohio, US; Sep. 28, 2008. XP002777348, retrieved from STN Database Accession No. 1053654-17-3; 1 page.
Gududuru et al., "Identification of Darmstoff analogs as selective agonists and antagonists of lysophosphatidic acid receptors", Bioorg Med Chem Lett. (Dec. 31, 2006) 16:451-456.
Han et al., "Study of the prodrugs of peptide aldehydes as proteasome inhibitors", J Chin Pharma Sciences, (Dec. 31, 2012) 21:21-27.
Oka et al., An oxazaphospholidine approach for the stereocontrolled synthesis of oligonucleoside phosphorothioates. J Am Chem Soc. (2003) 125(27):8307-8317.
Shao et al., Synthesis of new cyclicphosphates of 3-hydroxyisoxazole and their diastereomers. Chin Chem Ltts (1993) 4(9):767-758.
Yang et al., "Effects of Guanosine Tetraphosphate, Guanosine Pentaphosphate, and β-γ Methylenyl-Guanosine Pentaphosphate on Gene Expression of *Escherichia coli* In Vitro" Proc. Nat. Acad. Sci. USA. vol. 71, No. 1, pp. 63-67, Jan. 1974.
Chinese Office Action dated Jan. 19, 2018, issued in related CN Application No. 201580008367.0.
European Partial Supplemental Search Report dated Jul. 5, 2017 in corresponding Application No. 15748902.2.
European Extended Search Report dated Oct. 11, 2017 in corresponding Application No. 15748902.2.

(56) References Cited

OTHER PUBLICATIONS

Japanese Search Report dated Oct. 4, 2018 in corresponding Application No. 2016-547558.
Chen et al., "Conformation Analysis of Guanosine-5'-Diphospho-Fucose", Chin Chem Ltt. (1996) 7(1):29-32.
Chen et al., "Conformation Analysis of Tunicamycin V and its Natural Substrate", Chin Chem Ltt. (1996) 7(2):153-156.
Cote et al., "D-2 dopamine receptor-mediated inhibition of adenylate cyclase activity in the intermediate lobe of the rat pituitary gland requires guanosine 5'-triphosphate," Endocrinology (1982) 110(3):812-819.
Shoshani et al., "Enzymatic synthesis of unlabeled and beta-32P-labeled beta-L-2',3'dideoxyadenosine-5'-triphosphate . . . ", J Biol Chem. 1999, 274(49):34735-34741.
Yang et al., Accession No. 1974:421578 CAPLUS, "Effects of guanosine tetraphosphate et al.", XP-002777343 in 1 page.
Australian Examination Report dated Feb. 4, 2019 in Application No. 2015217221.
Chinese Office Action dated Nov. 13, 2018 in Application No. 201580008367.0.
Indian Examination Report dated Mar. 28, 2019 in Application No. 201617025365.

\* cited by examiner

PRODRUG COMPOUNDS AND THEIR USES

CROSS-REFERENCE TO RELATED APPLICATIONS

This application is a 371 of international application PCT/US2015/015496 filed Feb. 11, 2015, which claims priority to and the benefit of U.S. Provisional Application No. 61/939,615, filed on Feb. 13, 2014, U.S. Provisional Application No. 61/988,101, filed on May 2, 2014, and U.S. Provisional Application No. 61/988,118, filed on May 2, 2014, the entire contents of all of which are incorporated herein by reference.

FIELD

Compositions and methods in the field of medicine and chemistry are disclosed. Some of the disclosed embodiments are directed to medicinal prodrug compounds, medicinal compositions, as well as processes for their preparation and methods of their use. Some embodiments include prodrug compounds of acid/alcohol derivatives, their preparation and their uses. In some embodiments, such prodrug compounds are useful to selectively deliver the acid/alcohol derivatives to the liver.

BACKGROUND

The following description of the background is provided to aid in understanding the invention, but is not admitted to be, or to describe, prior art, Prodrugs are frequently used to improve certain properties of pharmacological agents for a preferred route of administration, including physicochemical, biopharmaceutical or pharmacokinetic properties. Certain prodrugs (also called soft drugs) are designed by tissue selective activation or deactivation to achieve therapeutic advantages (See J. Rautio, et al. Nature Reviews Drug Discovery 7:255-270 (2008)).

Certain cyclic phosphate, phosphonate, phosphonamidate, and phosphoramidate prodrugs are disclosed in U.S. Pat. Nos. 6,312,662 and 7,205,404 and designed for liver-targeting of pharmacological agents. These prodrugs are activated by liver cytochrome P450 enzymes CYP3As that are predominantly expressed in the target tissue and designed to achieve the selective delivery of pharmacological agents to the liver. Since the prodrugs are not active outside the liver, the liver-targeting strategy reduces any pharmacological or toxicological effects of a biologically active agent outside the targeting tissue. As a result, once used to treat liver diseases or to treat diseases via intervening in molecular pathways in the liver, the liver-targeting strategy significantly improves patient benefit/risk ratio of a pharmacological agent (e.g. see M. D. Erion, et al. J Pharm Exp Ther 312:554-60 (2005)). Example activation of these cyclic phosph(on)ate and phosphoramidate compounds are illustrated below:

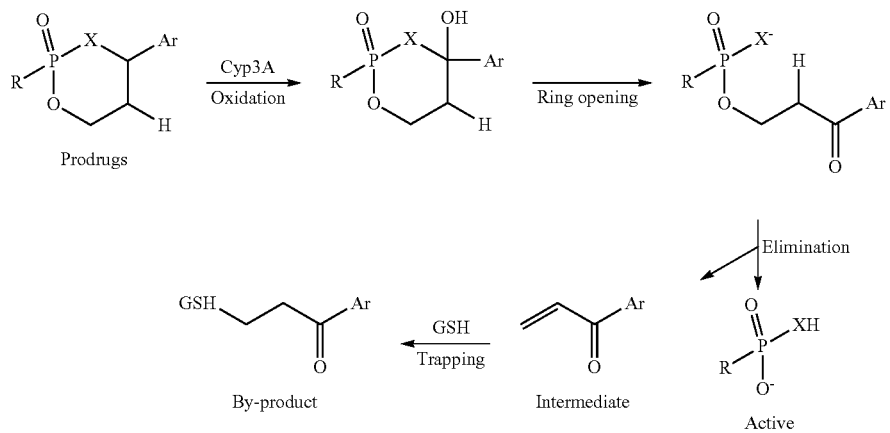

In the above example, the cyclic prodrugs (X=O or N) are oxidized by Cyp3A in the liver and undergo a ring opening and β-elimination sequence to provide the active drugs and an aryl vinyl ketone (Intermediate). The latter is rapidly conjugated with glutathione (GSH) that exists in millimole levels in the liver to yield the conjugate by-product.

Certain oral available pharmaceutical agents have been described to have certain liver-targeted property (e.g. see X. J. Zhou, et al. 2009 EASL, meeting poster #966). The liver-targeting effects of these agents are based on liver first-pass metabolism of an orally administered agent and the liver-targeting efficiency varies widely, depending upon the pharmacokinetic property of the agent, and are not as efficient as the Cyp3A activated prodrugs.

SUMMARY

Novel prodrug compounds of acid/alcohol derivatives such as phosphates, phosphonates, phosphonamidates, phosphoramidates, carboxylates, phenolates, and alkoxylates, their preparation and their uses are described. Some embodiments are related to novel prodrug compounds that do not generate a vinyl keto reactive intermediate in the activation process. Some embodiments are directed to the use of the prodrugs to enhance oral drug delivery. Another aspect includes the use of prodrugs to treat diseases that benefit from enhanced drug distribution to the liver and like tissues and cells, including but not limited to hepatitis, cancer, liver fibrosis, fatty liver, malaria, other viral and parasitic infections, and metabolic, cardiovascular, and/or hormonal diseases where the liver is involved in the production and/or the homeostasis control of the biochemical end products, e.g. glucose, cholesterol, fatty acids, bile acids, triglycerides, lipoproteins, apolipoproteins, and sex hormone-binding globulin (SHBG). Examples of such diseases include diabetes, hyperlipidemia, atherosclerosis, obesity and the like. In another aspect, prodrugs are used to prolong pharmacodynamic half-life of a drug. In some embodiments, the prodrug methodology can be used to achieve sustained delivery of the parent drug. In another aspect, prodrugs are used to increase the therapeutic index of the drug. In some embodiments, the prodrugs are useful in the delivery of diagnostic imaging agents to the liver. Some additional embodiments relate to a method of making prodrugs.

Some embodiments relate to a compound of Formula I:

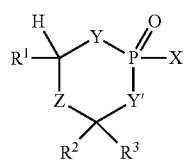

(I)

wherein:

$R^1$ and $R^2$ are each independently selected from the group consisting of H, M, an optionally substituted $C_1$-$C_6$ alkyl, an optionally substituted $C_1$-$C_6$ heteroalkyl, an optionally substituted $C_1$-$C_6$ alkyloxy, an optionally substituted $C_1$-$C_6$ acyloxy, an optionally substituted aryl, and an optionally substituted heteroaryl;

$R^3$ is selected from the group consisting of H and an optionally substituted $C_1$-$C_6$ alkyl; or $R^3$ optionally forms an optionally substituted ring with $R^2$; or $R^3$ together with $R^2$ form a methylene or its derivative; or $R^3$ together with $R^2$ form an oxo (=O) or its derivative; or $R^3$ optionally forms a bond with Z or Y' when Z or Y' is N;

M is a biological agent, or part of a biological agent or a prodrug of a biological agent:

X is selected from the group consisting of Cl, $OR^4$, $NR^4R^5$, an optionally substituted $C_1$-$C_6$ alkyl, and M;

Y and Y' are each independently O or $NR^4$; or Y' is $CH_2$ or null;

Z is selected from the group consisting of O, $NR^5$, $CR^8R^6$, C=O, C=$NR^7$, and null; or Z is a 2-5 atom spacer selected from an optionally substituted $C_1$-$C_6$ alkyl, an optionally substituted $C_1$-$C_6$ alkyloxy, an optionally substituted $C_1$-$C_6$ heteroalkyl, an optionally substituted aryl, and an optionally substituted heteroaryl;

$R^4$ is selected from the group of H, an optionally substituted $C_1$-$C_6$ alkyl, and an optionally substituted $C_1$-$C_6$ heteroalkyl;

$R^5$ is selected from the group consisting of H, M, an optionally substituted $C_1$-$C_6$ alkyl, an optionally substituted $C_1$-$C_6$ heteroalkyl, and an optionally substituted $C_1$-$C_6$ acyl;

$R^6$ is selected from the group consisting of F, Cl, an optionally substituted $C_1$-$C_6$ alkyl, and an optionally substituted $C_1$-$C_6$ heteroalkyl, or $R^6$ is H provided that $R^1$ or $R^2$ or $R^8$ is connected to a cyclic core carbon atom through an oxygen-carbon (O—C) bond;

$R^7$ is selected from the group consisting of H, an optionally substituted $C_1$-$C_6$ alkyl, and an optionally substituted $C_1$-$C_6$ heteroalkyl;

$R^8$ is selected from the group consisting of F, Cl, M, an optionally substituted $C_1$-$C_6$ alkyl, and an optionally substituted $C_1$-$C_6$ heteroalkyl; or $R^8$ is H provided that $R^1$ or $R^2$ is connected to a cyclic core carbon atom through an oxygen-carbon (O—C) bond;

provided that at least one of $R^1$, $R^2$, $R^5$, $R^8$ and X is M;

or a stereoisomer or a pharmaceutically acceptable salt thereof.

In some embodiments, the compound is a compound of Formula Ia:

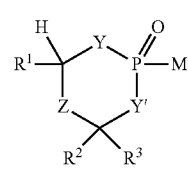

(Ia)

wherein;

$R^1$ is selected from the group consisting of H, an optionally substituted $C_1$-$C_6$ alkyl, an optionally substituted aryl, and an optionally substituted heteroaryl;

$R^2$ and $R^3$ are each independently selected from the group consisting of H and an optionally substituted $C_1$-$C_6$ alkyl; or $R^2$ and $R^3$ optionally form an optionally substituted ring; or $R^2$ and $R^3$ optionally form a methylene or its derivative; or $R^2$ and $R^3$ optionally form an oxo or its derivative;

M is a biological agent, part of a biological agent or a prodrug of a biological agent;

Y and Y' are each independently O or $NR^4$; or Y' is $CH_2$;

Z is selected from the group consisting of O, $NR^5$, $CR^8R^6$, C=O, C=$NR^7$, and null; or Z is a 2-5 atom spacer selected from an optionally substituted $C_1$-$C_6$ alkyl, an optionally substituted $C_1$-$C_6$ alkyloxy, an optionally substituted $C_1$-$C_6$ heteroalkyl, an optionally substituted aryl, and an optionally substituted heteroaryl;

$R^4$ is selected from the group consisting of H, an optionally substituted $C_1$-$C_6$ alkyl, and an optionally substituted $C_1$-$C_6$ heteroalkyl;

$R^5$ is selected from the group consisting of H, an optionally substituted $C_1$-$C_6$ alkyl, an optionally substituted $C_1$-$C_6$ heteroalkyl, and an optionally substituted $C_1$-$C_6$ acyl;

$R^6$ is selected from the group consisting of F, Cl, an optionally substituted $C_1$-$C_6$ alkyl, and an optionally substituted $C_1$-$C_6$ heteroalkyl; or $R^6$ is H provided that $R^1$ or $R^2$ or $R^8$ is connected with the cyclic core carbon atom through an oxygen-carbon (O—C) bond;

$R^7$ is selected from the group consisting of H, an optionally substituted $C_1$-$C_6$ alkyl, and an optionally substituted $C_1$-$C_6$ heteroalkyl;

$R^8$ is selected from the group consisting of F, Cl, M, an optionally substituted $C_1$-$C_6$ alkyl, and an optionally substituted $C_1$-$C_6$ heteroalkyl; or $R^8$ is H provided that $R^1$ or $R^2$ is connected to a cyclic core carbon atom through an oxygen-carbon (O—C) bond;

or a stereoisomer or a pharmaceutically acceptable salt thereof.

In some embodiments, the compound is a compound of Formula Ib:

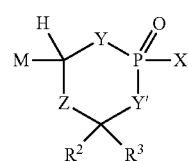

(Ib)

wherein:

$R^2$ and $R^3$ are independently selected from the group consisting of H and an optionally substituted $C_1$-$C_6$ alkyl; or $R^2$ and $R^3$ optionally form an optionally substituted ring; or $R^2$ and $R^3$ optionally form a methylene or its derivative; or $R^2$ and $R^3$ optionally form an oxo (=O) or its derivative;

M is a biological agent, part of a biological agent or a prodrug of a biological agent;

X is selected from the group consisting of Cl, an optionally substituted $C_1$-$C_6$ alkyl, $NR^4R^5$, and $OR^4$;

Y and Y' are each independently O or $NR^4$; or Y' is $CH_2$ or null;

Z is selected from the group consisting of O, $NR^5$, $C(R^6)_2$, C=O, C=$NR^7$, and null; or Z is a 2-5 atom spacer selected from an optionally substituted $C_1$-$C_6$ alkyl, an optionally substituted $C_1$-$C_6$ alkyloxy, an optionally substituted $C_1$-$C_6$ heteroalkyl, an optionally substituted aryl, and an optionally substituted heteroaryl;

$R^4$ is selected from the group consisting of H, an optionally substituted $C_1$-$C_6$ alkyl, and an optionally substituted $C_1$-$C_6$ heteroalkyl;

$R^5$ is selected from the group consisting of H, an optionally substituted $C_1$-$C_6$ alkyl, an optionally substituted $C_1$-$C_6$ heteroalkyl, and an optionally substituted $C_1$-$C_6$ acyl;

$R^6$ is selected from the group consisting of F, Cl, an optionally substituted $C_1$-$C_6$ alkyl, and an optionally substituted $C_1$-$C_6$ heteroalkyl; or $R^6$ is H provided that M or $R^2$ is connected with the cyclic core carbon atom through an oxygen-carbon (O—C) bond;

$R^7$ is selected from the group consisting of H, an optionally substituted $C_1$-$C_6$ alkyl, and an optionally substituted $C_1$-$C_6$ heteroalkyl;

or a stereoisomer or a pharmaceutically acceptable salt thereof.

In some embodiments, the compound is a compound of Formula Ic:

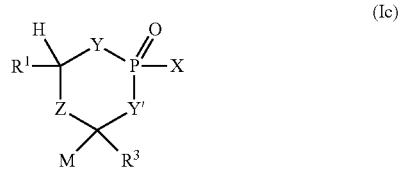

(Ic)

wherein:

$R^1$ is selected from the group consisting of H, an optionally substituted $C_1$-$C_6$ alkyl, an optionally substituted $C_1$-$C_6$ heteroalkyl, an optionally substituted aryl, and an optionally substituted heteroaryl;

$R^3$ is selected from the group consisting of H and an optionally substituted $C_1$-$C_6$ alkyl; or $R^3$ together with M form a methnylene derivative; or $R^3$ optionally forms a bond with Z or Y' when Z or Y' is N;

M is a biological agent, part of a biological agent or a prodrug of a biological agent;

X is selected from the group consisting of Cl, $OR^4$, $NR^4R^5$, and an optionally substituted $C_1$-$C_6$ alkyl;

Y and Y' are each independently O or $NR^4$;

Z is selected from the group consisting of O, $NR^5$, $C(R^6)_2$, C=O, C=$NR^7$, and null; or Z is a 2-5 atom spacer selected from an optionally substituted $C_1$-$C_6$ alkyl, an optionally substituted $C_1$-$C_6$ alkyloxy, an optionally substituted $C_1$-$C_6$ heteroalkyl, an optionally substituted aryl, and an optionally substituted heteroaryl;

$R^4$ is selected from the group consisting of H, an optionally substituted $C_1$-$C_6$ alkyl, and an optionally substituted $C_1$-$C_6$ heteroalkyl;

$R^5$ is selected from the group consisting of H, an optionally substituted $C_1$-$C_6$ alkyl, an optionally substituted $C_1$-$C_6$ heteroalkyl, and an optionally substituted $C_1$-$C_6$ acyl;

$R^6$ is selected from the group consisting of F, Cl, an optionally substituted $C_1$-$C_6$ alkyl, and an optionally substituted $C_1$-$C_6$ heteroalkyl; or $R^6$ is H provided that $R^1$ or M is connected with the cyclic core carbon atom through an oxygen-carbon (O—C) bond;

$R^7$ is selected from the group consisting of H, an optionally substituted $C_1$-$C_6$ alkyl, and an optionally substituted $C_1$-$C_6$ heteroalkyl;

or a stereoisomer or a pharmaceutically acceptable salt thereof.

In some embodiments, the compound is a compound of Formula Id or Ie:

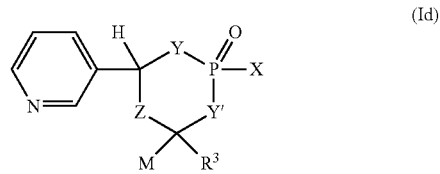

(Id)

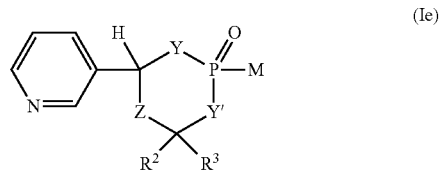

(Ie)

wherein:

$R^2$ and $R^3$ are independently selected from the group consisting of H and an optionally substituted $C_1$-$C_6$ alkyl; or $R^3$ together with M or $R^2$ form a methylene derivative; or $R^3$ together with M or $R^2$ form an optionally substituted ring; or $R^3$ together with $R^2$ form an oxo (=O) or its derivative; or $R^3$ optionally forms a bond with Z or Y' when Z or Y' is N;

M is a biological agent, part of a biological agent or a prodrug of a biological agent;

X is selected from the group consisting of Cl, $OR^4$, and an optionally substituted $C_2$-$C_6$ alkyl;

Y and Y' are each independently O or N; or Y' is $CH_2$;

Z is selected from the group consisting of O and NR;

$R^4$ is selected from the group consisting of H, an optionally substituted $C_1$-$C_6$ alkyl, and an optionally substituted $C_1$-$C_6$ heteroalkyl;

$R^5$ is selected from the group consisting of H, an optionally substituted $C_1$-$C_6$ alkyl, an optionally substituted $C_1$-$C_6$ heteroalkyl, and an optionally substituted $C_1$-$C_6$ acyl;

or a stereoisomer or a pharmaceutically acceptable salt thereof.

Some embodiments relate to a compound of Formula II:

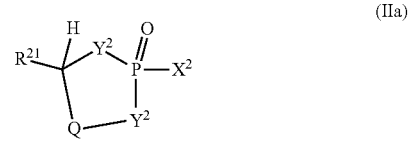

(IIa)

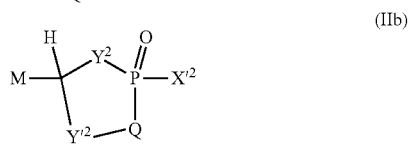

(IIb)

wherein:

R²¹ is selected from the group consisting of H, M, an optionally substituted $C_1$-$C_6$ alkyl, an optionally substituted $C_1$-$C_6$ heteroalkyl, an optionally substituted $C_1$-$C_6$ alkyloxy, an optionally substituted $C_1$-$C_6$ acyloxy, an optionally substituted aryl, and an optionally substituted heteroaryl;

M is a biological agent, or part of a biological agent or a prodrug of a biological agent;

Q is an optionally substituted aryl or an optionally substituted heteroaryl;

$X^2$ is selected from the group consisting of Cl, $OR^{24}$, $N(R^{24})_2$ an optionally substituted $C_2$-$C_6$ alkyl, and M;

$X'^2$ is selected from the group consisting of Cl, $N(R,^{24})_2$, and $OR^{24}$;

$Y^2$ and $Y'^2$ are each independently O or $NR^{24}$;

$R^{24}$ is selected from the group of H, an optionally substituted $C_1$-$C_6$ alkyl, and an optionally substituted $C_1$-$C_6$ heteroalkyl;

provided that at least one of $R^{21}$ and $X^2$ is M;

or a stereoisomer or a pharmaceutically acceptable salt thereof.

Some embodiments relate to a compound of Formula III:

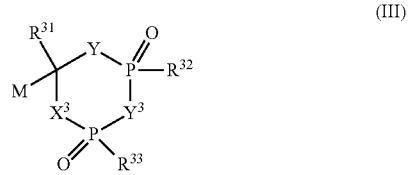

(III)

wherein:

$R^{31}$ is H; or $R^{31}$ optionally forms a bond with M or $X^3$ when $X^3$ is N:

$R^{32}$ and $R^{33}$ are each independently selected from the group consisting of Cl, OH, $NH_2$, an optionally substituted $C_1$-$C_6$ alkyl, an optionally substituted $C_1$-$C_6$ alkyloxy, and an optionally substituted $C_1$-$C_6$ alkylamino;

M is a biological agent or part of a biological agent or a prodrug of a biological agent;

$X^3$ is O or $NR^{34}$;

$Y^3$ is selected from the group consisting of O, $N^{34}$, and an optionally substituted $C_1$-$C_6$ alkyl;

$R^{34}$ is selected from the group consisting of H, an optionally substituted $C_1$-$C_6$ alkyl, and an optionally substituted $C_1$-$C_6$ heteroalkyl;

or a stereoisomer or a pharmaceutically acceptable salt thereof.

Some embodiments relate to a compound of Formula IV:

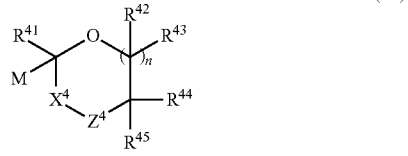

(IV)

wherein:

$R^{41}$ is H; or $R^{41}$ optionally forms a bond with M or $X^4$ when $X^4$ is N:

$Z^4$ is selected from the group consisting of $CR^{46}R^{47}$, C(O), C(O)O, $C(O)NR^{48}$, $SO_2$, an optionally substituted aryl, and an optionally substituted heteroaryl;

$R^{42}$, $R^{43}$, $R^{44}$, $R^{45}$, $R^{46}$, and $R^{47}$ are each independently selected from the group consisting of H, OH, amino, an optionally substituted $C_1$-$C_6$ alkyl, an optionally substituted $C_1$-$C_6$ alkyloxy, an optionally substituted $C_1$-$C_6$ acyloxy, an optionally substituted $C_1$-$C_6$ hereroalkyl, an optionally substituted phosphate, an optionally substituted phosphonate, an optionally substituted aryl, and an optionally substituted heterocycle; or $R^{44}$ and $R^{45}$ are independently or together optionally linked with $R^{42}$, $R^{43}$, $R^{46}$, or $R^{47}$ to form an optionally substituted ring; or $R^{44}$ is optionally M; or $R^{44}$ and $R^{45}$ are together optionally to form an oxo (=O) or its derivative;

M is a biological agent or part o: a biological agent or a prodrug of a biological agent;

$X^4$ is selected from the group consisting of O, $NR^{48}$, $NC(O)R^{48}$, $NS(O)_2R^{49}$, and $NP(O)(R^{50})_2$;

$R^{48}$ is selected from the group consisting of H, an optionally substituted $C_1$-$C_6$ alkyl, and an optionally substituted $C_1$-$C_6$ heteroalkyl;

$R^{49}$ is selected from the group consisting of $NH_2$, an optionally substituted $C_1$-$C_6$ alkyl, an optionally substituted aryl, and an optionally substituted heteroaryl;

$R^{50}$ is selected from the group consisting of OH, $NH_2$, an optionally substituted $C_1$-$C_6$ alkyl, an optionally substituted $C_1$-$C_6$ alkyloxy, and an optionally substituted $C_1$-$C_6$ alkylamino;

n is 0, 1, 2, or 3;

or a stereoisomer or a pharmaceutically acceptable salt thereof.

Some embodiments relate to a compound of Formula V:

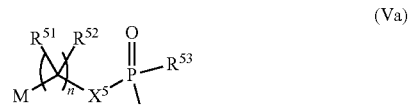

(Va)

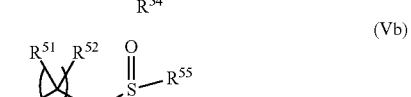

(Vb)

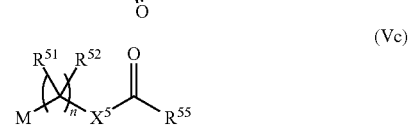

(Vc)

wherein:

$R^{51}$ and $R^{52}$ are each independently selected from the group consisting of H, an optionally substituted $C_1$-$C_6$ alkyl, an optionally substituted $C_1$-$C_6$ heteroalkyl, an optionally substituted $C_1$-$C_6$ alkyloxy, an optionally substituted $C_1$-$C_6$ acyloxy, an optionally substituted $C_1$-$C_6$ acylamino, an optionally substituted phosphate, an optionally substituted phosphonate, an optionally substituted phosphoramidate, an optionally substituted $C_1$-$C_6$ aryl, and an optionally substituted heteroaryl; or $R^{51}$ and $R^{52}$ are together optionally to form an oxo (=O) or its derivative;

$R^{53}$ and $R^{54}$ are each independently selected from the group consisting of Cl, OH, $NH_2$, an optionally substituted $C_1$-$C_6$ alkyl, an optionally substituted $C_1$-$C_6$ alkyloxy, an optionally substituted $C_1$-$C_6$ alkylamino, an optionally substituted $C_1$-$C_6$ acylamino, an optionally substituted aryloxy, an optionally substituted phosphate, an optionally substituted phosphonate, and an optionally substituted heteroaryloxy; or $R^{53}$ is optionally linked with $R^{51}$, $R^{54}$, or $R^{56}$ to form an optionally substituted 5-, 6-, or 7-membered heterocycle;

$R^{55}$ is selected from the group consisting of OH, $NH_2$, an optionally substituted $C_1$-$C_6$ alkyl, an optionally substituted $C_1$-$C_6$ alkyloxy, an optionally substituted $C_1$-$C_6$ alkylamino, an optionally substituted aryl, and an optionally substituted heteroaryl; or $R^{55}$ is optionally linked to $R^{51}$ or $R^{56}$ to form an optionally substituted ring;

$R^{56}$ is selected from the group consisting of H, a $C_1$-$C_6$ alkyl, and a $C_1$-$C_6$ heteroalkyl;

M is a biological agent or part of a biological agent or a prodrug of a biological agent:

$X^5$ is O or $NR^{56}$;

n is 0, 1, 2, or 3;

or a stereoisomer or a pharmaceutically acceptable salt thereof.

Some embodiments relate to a compound of Formula VI:

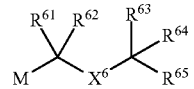
(VIa)

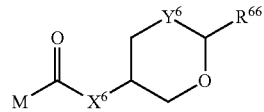
(VIb)

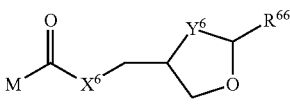
(VIc)

wherein:

$R^{61}$ and $R^{62}$ are each independently selected from the group consisting of H, an optionally substituted $C_1$-$C_6$ alkyloxy, an optionally substituted $C_1$-$C_6$ alkylamino, an optionally substituted $C_1$-$C_6$ acyloxy, —$OCH_2P(O)(R^{69})_2$, and an optionally substituted $C_1$-$C_6$ acylamino; or $R^{61}$ and $R^{62}$ together optionally form an oxo (=O) or its derivative;

$R^{63}$, $R^{64}$, and $R^{65}$ are each independently selected from the group consisting of H, $CO_2R^{67}$, $C(O)N(R^{67})_2$, $P(O)(R^{69})_2$, an optionally substituted $C_1$-$C_6$ alkyl, an optionally substituted $C_1$-$C_6$ alkyloxy, an optionally substituted $C_1$-$C_6$ acyloxy, and an optionally substituted $C_1$-$C_6$ hereroalkyl; or two of $R^{63}$, $R^{64}$, and $R^{65}$ are optionally linked to form an optionally substituted ring; or $R^{63}$ is optionally linked with $R^{68}$ to form an optionally substituted ring; with the proviso that $CR^{63}R^{64}R^{65}$ is not a straight chain $C_1$-$C_4$ alkyl when $R^{61}$ and $R^{62}$ form an oxo (=O);

$R^{66}$ is selected from the group consisting of H, an optionally substituted $C_1$-$C_6$ alkyl, an optionally substituted $C_1$-$C_6$ alkyloxy, an optionally substituted $C_1$-$C_6$ heteroalkyl, an optionally substituted aryl, and an optionally substituted heteroaryl;

$R^{67}$ and $R^{68}$ are each independently selected from the group consisting of H, an optionally substituted $C_1$-$C_6$ alkyl, and an optionally substituted $C_1$-$C_6$ heteroalkyl;

$R^{69}$ is selected from the group consisting of OH, an optionally substituted $C_1$-$C_6$ alkyl, an optionally substituted $C_1$-$C_6$ alkyloxy, and an optionally substituted $C_1$-$C_6$ alkylamino;

M is a biological agent or part of a biological agent or a prodrug of a biological agent;

$X^6$ is O or $NR^{68}$;

$Y^6$ is selected from the group consisting of null, O, $NR^{68}$, and $C(R^{68})_2$;

or a stereoisomer or a pharmaceutically acceptable salt thereof.

Some embodiments relate to a compound of Formula VII:

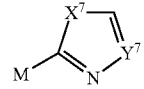
(VII)

wherein:

$R^{71}$ is selected from the group consisting of H, OH, an optionally substituted $C_1$-$C_6$ alkyl, an optionally substituted $C_1$-$C_6$ heteroalkyl, an optionally substituted $C_1$-$C_6$ alkyloxy, an optionally substituted phosphate, and an optionally substituted phosphonate;

$X^7$ is O or S;

$Y^7$ is N or $CR^{71}$;

M is a biological agent or part of a biological agent or a prodrug of a biological agent;

or a stereoisomer or a pharmaceutically acceptable salt thereof.

In some embodiments, the compound is selected from the group consisting of:

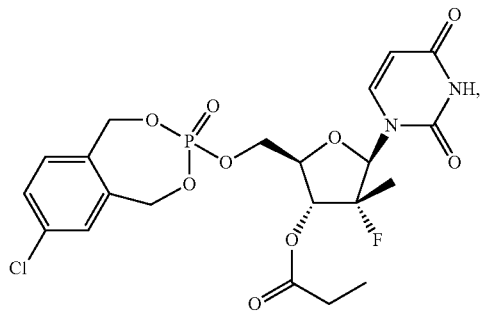

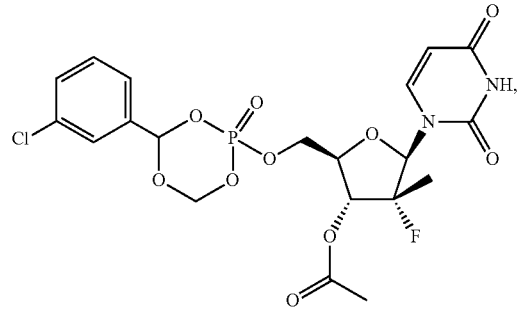

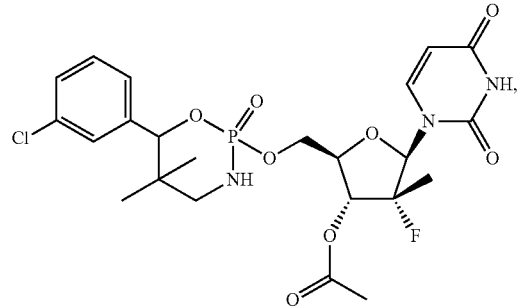

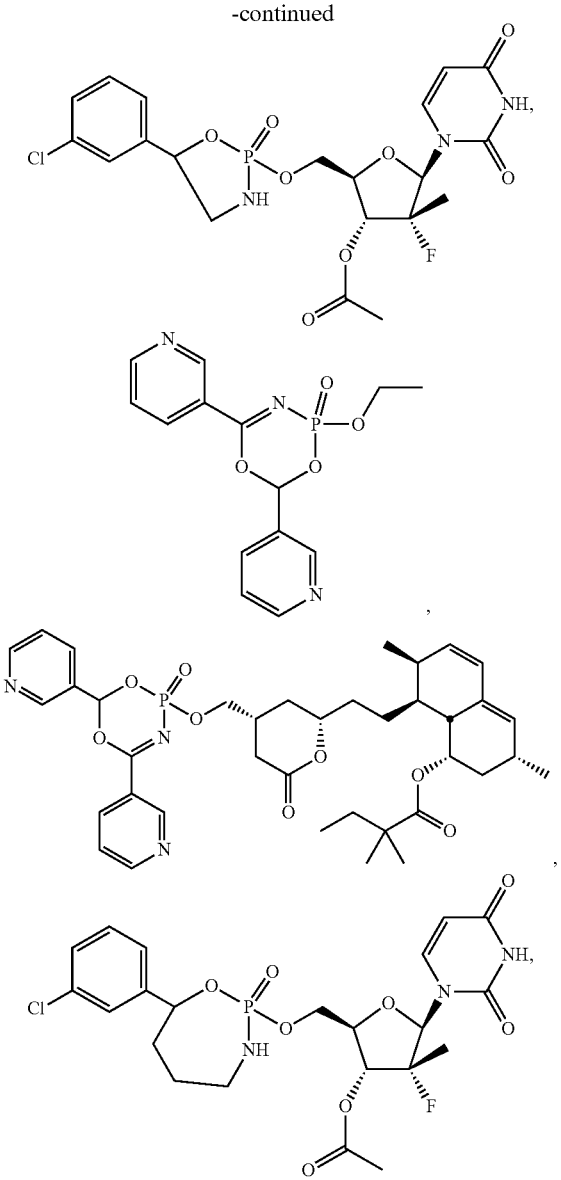

and a stereoisomer or a pharmaceutically acceptable salt thereof.

In some embodiments, M is a nucleoside antiviral or anticancer agent.

In some embodiments, M is a lipid modulator.

In some embodiments, M is selected from the group consisting of HMG-CoA reductase inhibitor, a selective thyroid hormone receptor modulator, a peroxisome proliferator-activated receptor modulator, a fibrate, a nicotinic acid, a bile acid, and a fatty acid.

In some embodiments, M is a glucose modulator.

In some embodiments. M is selected from the group consisting of a peroxisome proliferator-activated receptor modulator, a glucose biosynthesis inhibitor, and a dipeptidyl peptidase 4 inhibitor.

In some embodiments, M is a nuclear hormone receptor modulator.

Some embodiments relate to a pharmaceutical composition comprising any of the above compounds and a pharmaceutically acceptable excipient.

Some embodiments relate to a method of treating a disease, disorder or condition comprising administering an effective amount of any of the above compounds to a subject in need thereof.

In some embodiments, the disease, disorder or condition is a disease, disorder or condition of the liver.

In some embodiments, the disease, disorder or condition is a metabolic, cardiovascular or hormonal disease in which the liver is involved in the production and/or the homeostasis control of the biochemical end products of the disease, disorder or condition.

In some embodiments, the disease, disorder or condition is selected from the group consisting of hepatitis, liver cancer, liver fibrosis, fatty liver, malaria, viral infection, parasitic infection, diabetes, hyperlipidemia, atherosclerosis, obesity, dyslipidemia, hyperglycemia and a hormonal condition.

Some embodiments relate to a method of treating a liver disease comprising administering an effective amount of any of the above compounds to a subject in need thereof, wherein M is a nucleoside antiviral or anticancer agent.

Some embodiments relate to a method of treating dyslipidemia comprising administering to a subject in need thereof an effective amount of any of the above compounds, wherein M is a lipid modulator.

In some embodiments, M is selected from the group consisting of HMG-CoA reductase inhibitor, a selective thyroid hormone receptor modulator, peroxisome proliferator-activated receptor modulator, a fibrate, nicotinic acid, a bile acid, and a fatty acid.

Some embodiments relate to method of treating hyperglycemia comprising administering to a subject in need thereof, an effective amount of any of the above compounds, wherein M is a glucose modulator.

In some embodiments, M is selected from the group consisting of peroxisome proliferator-activated receptor modulator, glucose biosynthesis inhibitor, and dipeptidyl peptidase 4 inhibitor.

Some embodiments relate to a method of treating a hormonal condition comprising administering to a subject in need thereof, an effective amount of any of the above compounds, wherein M is a nuclear hormone receptor modulator.

Some embodiments further comprise administering an effective amount of at least one additional therapeutic agent to the subject in need thereof.

Some embodiments relate to a method of delivering a diagnostic imaging agent to the liver of a subject in need thereof, comprising administering to the subject an effective amount of any of the above compounds.

In some embodiments, the subject is a mammal.

In some embodiments, the subject is human.

Some embodiments relate to a method of inhibiting viral replication in a cell comprising contacting the cell with any of the above compounds.

Some embodiments relate to a method of intervening in a molecular pathway or modulating a target in a cell comprising contacting the cell with any of the above compounds.

In some embodiments, the cell is in vivo.
In some embodiments, the cell is ex vivo.
In some embodiments, the cell is a hepatocyte.
In some embodiments, the cell is mammalian.
In some embodiments, the cell is human.

DETAILED DESCRIPTION

The present embodiments are directed to compositions and methods related to novel prodrug compounds of biologically active acid/alcohol derivatives such as phosphates, phosphonates, phosphonamidates, phosphoramidates, carboxylates, phenolates, and alkoxylates, their preparation and their uses. These prodrug compounds and their stereoisomers and pharmaceutically acceptable salts are represented by the formulae discussed below.

Some embodiments relate to a compound of Formula I:

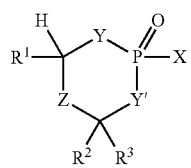

(I)

wherein:

$R^1$ and $R^2$ are each independently selected from the group consisting of H, M, an optionally substituted $C_1$-$C_6$ alkyl, an optionally substituted $C_1$-$C_6$ heteroalkyl, an optionally substituted $C_1$-$C_6$ alkyloxy, an optionally substituted $C_1$-$C_6$ acyloxy, an optionally substituted aryl, and an optionally substituted heteroaryl;

$R^3$ is selected from the group consisting of H and an optionally substituted $C_1$-$C_6$ alkyl; or $R^3$ optionally forms an optionally substituted ring with $R^2$; or $R^3$ together with $R^2$ form a methylene or its derivative; or $R^3$ together with $R^2$ form an oxo (=O) or its derivative; or $R^3$ optionally forms a bond with Z or Y' when Z or Y' is N;

M is a biological agent, or part of a biological agent or a prodrug of a biological agent;

X is selected from the group consisting of Cl, $OR^4$, $NR^4R^5$, an optionally substituted $C_1$-$C_6$ alkyl, and M;

Y and Y' are each independently O or $NR^4$; or Y' is $CH_2$ or null;

Z is selected from the group consisting of O, $NR^5$, $CR^8R^6$, C=O, C=$NR^7$, and null; or Z is a 2-5 atom spacer selected from an optionally substituted $C_1$-$C_6$ alkyl, an optionally substituted $C_1$-$C_6$ alkyloxy, an optionally substituted $C_1$-$C_6$ heteroalkyl, an optionally substituted aryl, and an optionally substituted heteroaryl;

$R^4$ is selected from the group of H, an optionally substituted $C_1$-$C_6$ alkyl, and an optionally substituted $C_1$-$C_6$ heteroalkyl;

$R^5$ is selected from the group consisting of H, M, an optionally substituted $C_1$-$C_6$ alkyl, an optionally substituted $C_1$-$C_6$ heteroalkyl, and an optionally substituted $C_1$-$C_6$ acyl;

$R^6$ is selected from the group consisting of F, Cl, an optionally substituted $C_1$-$C_6$ alkyl, and an optionally substituted $C_1$-$C_6$ heteroalkyl; or $R^6$ is H provided that $R^1$ or $R^2$ or $R^8$ is connected to a cyclic core carbon atom through an oxygen-carbon (O—C) bond;

$R^7$ is selected from the group consisting of H, an optionally substituted $C_1$-$C_6$ alkyl, and an optionally substituted $C_1$-$C_6$ heteroalkyl;

$R^8$ is selected from the group consisting of F, Cl, M, an optionally substituted $C_1$-$C_6$ alkyl, and an optionally substituted $C_1$-$C_6$ heteroalkyl; or $R^8$ is H provided that $R^1$ or $R^2$ is connected to a cyclic core carbon atom through an oxygen-carbon (O—C) bond;

provided that at least one of $R^1$, $R^2$, $R^5$, $R^8$, and X is M; or a stereoisomer or a pharmaceutically acceptable salt thereof.

In some embodiments, the compound is a compound of Formula Ia:

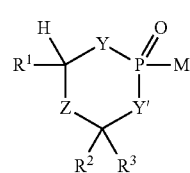

(Ia)

wherein:

$R^1$ is selected from the group consisting of H, an optionally substituted $C_1$-$C_6$ alkyl, an optionally substituted aryl, and an optionally substituted heteroaryl;

$R^2$ and $R^3$ are each independently selected from the group consisting of H and an optionally substituted $C_1$-$C_6$ alkyl; or $R^2$ and $R^3$ optionally form an optionally substituted ring; or $R^2$ and $R^3$ optionally form a methylene or its derivative; or $R^2$ and $R^3$ optionally form an oxo or its derivative;

M is a biological agent, part of a biological agent or a prodrug of a biological agent;

Y and Y' are each independently O or $NR^4$; or Y' is $CH_2$;

Z is selected from the group consisting of O, $NR^5$, $CR^8R^6$, C=O, C=$NR^7$, and null; or Z is a 2-5 atom spacer selected from an optionally substituted $C_1$-$C_6$ alkyl, an optionally substituted $C_1$-$C_6$ alkyloxy, an optionally substituted $C_1$-$C_6$ heteroalkyl, an optionally substituted aryl, and an optionally substituted heteroaryl;

$R^4$ is selected from the group consisting of H, an optionally substituted $C_1$-$C_6$ alkyl, and an optionally substituted $C_1$-$C_6$ heteroalkyl;

$R^5$ is selected from the group consisting of H, an optionally substituted $C_1$-$C_6$ alkyl, an optionally substituted $C_1$-$C_6$ heteroalkyl, and an optionally substituted $C_1$-$C_6$ acyl;

$R^6$ is selected from the group consisting of F, Cl, an optionally substituted $C_1$-$C_6$ alkyl, and an optionally substituted $C_1$-$C_6$ heteroalkyl; or $R^6$ is H provided that $R^1$ or $R^2$ or $R^8$ is connected with the cyclic core carbon atom through an oxygen-carbon (O—C) bond;

$R^7$ is selected from the group consisting of H, an optionally substituted $C_1$-$C_6$ alkyl, and an optionally substituted $C_1$-$C_6$ heteroalkyl;

$R^8$ is selected from the group consisting of F, Cl, M, an optionally substituted $C_1$-$C_6$ alkyl, and an optionally substituted $C_1$-$C_6$ heteroalkyl; or $R^8$ is H provided that $R^1$ or $R^2$ is connected to a cyclic core carbon atom through an oxygen-carbon (O—C) bond;

or a stereoisomer or a pharmaceutically acceptable salt thereof.

In some embodiments, the compound is a compound of Formula Ib:

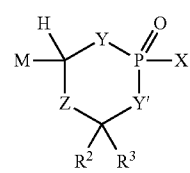

(Ib)

wherein:

$R^2$ and $R^3$ are independently selected from the group consisting of H and an optionally substituted $C_1$-$C_6$ alkyl; or $R^2$ and $R^3$ optionally form an optionally substituted ring; or $R^2$ and $R^3$ optionally form a methylene or its derivative; or $R^2$ and $R^3$ optionally form an oxo (=O) or its derivative;

M is a biological agent, part of a biological agent or a prodrug of a biological agent;

X is selected from the group consisting of Cl, an optionally substituted $C_1$-$C_6$ alkyl, $NR^4R^5$, and $OR^4$;

Y and Y' are each independently O or $NR^4$; or Y' is $CH_2$ or null;

Z is selected from the group consisting of O, $NR^5$, $C(R^6)_2$, C=O, C=$NR^7$, and null; or Z is a 2-5 atom spacer selected from an optionally substituted $C_1$-$C_6$ alkyl, an optionally substituted $C_1$-$C_6$ alkyloxy, an optionally substituted $C_1$-$C_6$ heteroalkyl, an optionally substituted aryl, and an optionally substituted heteroaryl;

$R^4$ is selected from the group consisting of H, an optionally substituted $C_1$-$C_6$ alkyl, and an optionally substituted $C_1$-$C_6$ heteroalkyl;

$R^5$ is selected from the group consisting of H, an optionally substituted $C_1$-$C_6$ alkyl, an optionally substituted $C_1$-$C_6$ heteroalkyl, and an optionally substituted $C_1$-$C_6$ acyl;

$R^6$ is selected from the group consisting of F, Cl, an optionally substituted $C_1$-$C_6$ alkyl, and an optionally substituted $C_1$-$C_6$ heteroalkyl; or $R^6$ is H provided that M or $R^2$ is connected with the cyclic core carbon atom through an oxygen-carbon (O—C) bond;

$R^7$ is selected from the group consisting of H, an optionally substituted $C_1$-$C_6$ alkyl, and an optionally substituted $C_1$-$C_6$ heteroalkyl;

or a stereoisomer or a pharmaceutically acceptable salt thereof.

In some embodiments, the compound is a compound of Formula Ic:

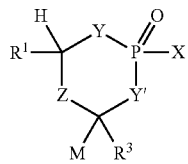

(Ic)

wherein:

$R^1$ is selected from the group consisting of H, an optionally substituted $C_1$-$C_6$ alkyl, an optionally substituted $C_1$-$C_6$ heteroalkyl, an optionally substituted aryl, and an optionally substituted heteroaryl;

$R^3$ is selected from the group consisting of H and an optionally substituted $C_1$-$C_6$ alkyl; or $R^3$ together with M form a methnylene derivative; or $R^3$ optionally forms a bond with Z or Y' when Z or Y' is N;

M is a biological agent, part of a biological agent or a prodrug of a biological agent;

X is selected from the group consisting of Cl, $OR^4$, $NR^4R^5$, and an optionally substituted $C_1$-$C_6$ alkyl;

Y and Y' are each independently O or $NR^4$;

Z is selected from the group consisting of O, $NR^5$, $C(R^6)_2$, C=O, C=$NR^7$, and null; or Z is a 2-5 atom spacer selected from an optionally substituted $C_1$-$C_6$ alkyl, an optionally substituted $C_1$-$C_6$ alkyloxy, an optionally substituted $C_1$-$C_6$ heteroalkyl, an optionally substituted aryl, and an optionally substituted heteroaryl;

$R^4$ is selected from the group consisting of H, an optionally substituted $C_1$-$C_6$ alkyl, and an optionally substituted $C_1$-$C_6$ heteroalkyl;

$R^5$ is selected from the group consisting of H, an optionally substituted $C_1$-$C_6$ alkyl, an optionally substituted $C_1$-$C_6$ heteroalkyl, and an optionally substituted $C_1$-$C_6$ acyl;

$R^6$ is selected from the group consisting of F, Cl, an optionally substituted $C_1$-$C_6$ alkyl, and an optionally substituted $C_1$-$C_6$ heteroalkyl; or $R^6$ is H provided that $R^1$ or M is connected with the cyclic core carbon atom through an oxygen-carbon (O—C) bond;

$R^7$ is selected from the group consisting of H, an optionally substituted $C_1$-$C_6$ alkyl, and an optionally substituted $C_1$-$C_6$ heteroalkyl;

or a stereoisomer or a pharmaceutically acceptable salt thereof.

In sonic embodiments, the compound is a compound of Formula Id or Ie:

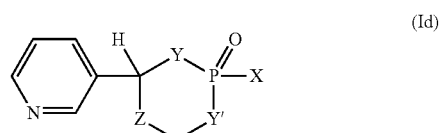

(Id)

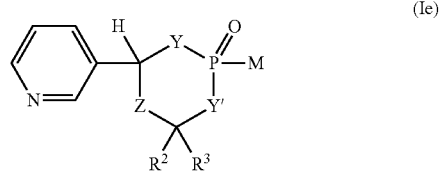

(Ie)

wherein:

$R^2$ and $R^3$ are independently selected from the group consisting of H and an optionally substituted $C_1$-$C_6$ alkyl; or $R^3$ together with M or $R^2$ form a methylene derivative; or $R^3$ together with M or $R^2$ form an optionally substituted ring; or $R^3$ together with $R^2$ form an oxo (=O) or its derivative; or $R^3$ optionally forms a bond with Z or Y' when Z or Y' is N;

M is a biological agent, part of a biological agent or a prodrug of a biological agent;

X is selected from the group consisting of Cl, $OR^4$, and an optionally substituted $C_2$-$C_6$ alkyl;

Y and Y' are each independently O or N; or Y' is $CH_2$;

Z is selected from the group consisting of O and $NR^5$;

$R^4$ is selected from the group consisting of H, an optionally substituted $C_1$-$C_6$ alkyl, and an optionally substituted $C_1$-$C_6$ heteroalkyl;

$R^5$ is selected from the group consisting of H, an optionally substituted $C_1$-$C_6$ alkyl, an optionally substituted $C_1$-$C_6$ heteroalkyl, and an optionally substituted $C_1$-$C_6$ acyl;

or a stereoisomer or a pharmaceutically acceptable salt thereof.

Some embodiments relate to a compound of Formula IIa or IIb:

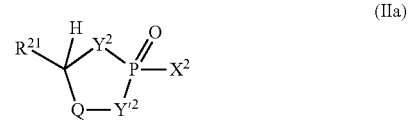

(IIa)

-continued

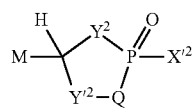

(IIb)

wherein:

$R^{21}$ is selected from the group consisting of H, M, an optionally substituted $C_1$-$C_6$ alkyl, an optionally substituted $C_1$-$C_6$ heteroalkyl, an optionally substituted $C_1$-$C_6$ alkyloxy, an optionally substituted $C_1$-$C_6$ acyloxy, an optionally substituted aryl, and an optionally substituted heteroaryl;

M is a biological agent, or part of a biological agent or a prodrug of a biological agent;

Q is an optionally substituted aryl or an optionally substituted heteroaryl;

$X^2$ is selected from the group consisting of Cl, $OR^{24}$, $N(R^{24})_2$ an optionally substituted $C_2$-$C_6$ alkyl, and M;

$X'^2$ is selected from the group consisting of Cl, $N(R^{24})_2$, and $OR^{24}$; $Y^2$ and $Y'^2$ are each independently O or $NR_{24}$;

$R^{24}$ is selected from the group of H, an optionally substituted $C_1$-$C_6$ alkyl, and an optionally substituted $C_1$-$C_6$ heteroalkyl;

provided that at least one of $R^{21}$ and $X^2$ is M;

or a stereoisomer or a pharmaceutically acceptable salt thereof.

Some embodiments relate to a compound of Formula III:

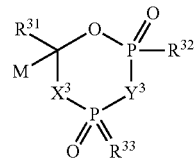

(III)

wherein:

$R^{31}$ is H; or $R^{31}$ optionally forms a bond with M or $X^3$ when $X^3$ is N;

$R^{32}$ and $R^{33}$ are each independently selected from the group consisting of Cl, OH, $NH_2$, an optionally substituted $C_1$-$C_6$ alkyl, an optionally substituted $C_1$-$C_6$ alkyloxy, and an optionally substituted $C_1$-$C_6$ alkylamino;

M is a biological agent or part of a biological agent or a prodrug of a biological agent;

$X^3$ is O or $NR^{34}$;

$Y^3$ is selected from the group consisting of O, $NR^{34}$, and an optionally substituted $C_1$-$C_6$ alkyl;

$R^{34}$ is selected from the group consisting of H, an optionally substituted $C_1$-$C_6$ alkyl, and an optionally substituted $C_1$-$C_6$ heteroalkyl;

or a stereoisomer or a pharmaceutically acceptable salt thereof.

Some embodiments relate to a compound of Formula IV:

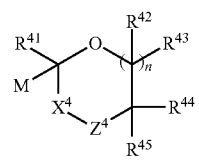

(IV)

wherein:

$R^{41}$ is H; or $R^{41}$ optionally forms a bond with M or $X^4$ when $X^4$ is N;

$Z^4$ is selected from the group consisting of $CR^{46}R^{47}$, C(O), C(O)O, C(O)$NR^{48}$, $SO_2$, an optionally substituted aryl, and an optionally substituted heteroaryl;

$R^{42}$, $R^{43}$, $R^{44}$, $R^{45}$, $R^{46}$, and $R^{47}$ are each independently selected from the group consisting of H, OH, amino, an optionally substituted $C_1$-$C_6$ alkyl, an optionally substituted $C_1$-$C_6$ alkyloxy, an optionally substituted $C_1$-$C_6$ acyloxy, an optionally substituted $C_1$-$C_6$ hereroalkyl, an optionally substituted phosphate, an optionally substituted phosphonate, an optionally substituted aryl, and an optionally substituted heterocycle; or $R^{44}$ and $R^{45}$ are independently or together optionally linked with $R^{42}$, $R^{43}$, $R^{46}$, or $R^{47}$ to form an optionally substituted ring; or $R^{44}$ is optionally M; or $R^{44}$ and $R^{45}$ are together optionally to form an oxo (=O) or its derivative;

M is a biological agent or part of a biological agent or a prodrug of a biological agent;

$X^4$ is selected from the group consisting of O, $NR^{48}$, $NC(O)R^{48}$, $NS(O)_2R^{49}$, and $NP(O)(R_{50})_2$;

$R^{48}$ is selected from the group consisting of H, an optionally substituted $C_1$-$C_6$ alkyl, and an optionally substituted $C_1$-$C_6$ heteroalkyl;

$R^{49}$ is selected from the group consisting of $NH_2$, an optionally substituted $C_1$-$C_6$ alkyl, an optionally substituted aryl, and an optionally substituted heteroaryl;

$R^{50}$ is selected from the group consisting of OH, $NH_2$, an optionally substituted $C_1$-$C_6$ alkyl, an optionally substituted $C_1$-$C_6$ alkyloxy, and an optionally substituted $C_1$-$C_6$ alkylamino;

n is 0, 1, 2, or 3;

or a stereoisomer or a pharmaceutically acceptable salt thereof.

Some embodiments relate to a compound of Formula Va, Vb, or Vc:

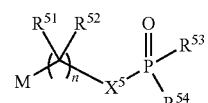

(Va)

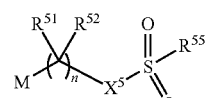

(Vb)

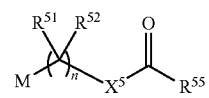

(Vc)

wherein:

$R^{51}$ and $R^{52}$ are each independently selected from the group consisting of H, an optionally substituted $C_1$-$C_6$ alkyl, an optionally substituted $C_1$-$C_6$ heteroalkyl, an optionally substituted $C_1$-$C_6$ alkyloxy, an optionally substituted $C_1$-$C_6$ acyloxy, an optionally substituted $C_1$-$C_6$ acylamino, an optionally substituted phosphate, an optionally substituted phosphonate, an optionally substituted phosphoramidate, an optionally substituted $C_1$-$C_6$ aryl, and an optionally substituted heteroaryl; or $R^{51}$ and $R^{52}$ are together optionally to form an oxo (=O) or its derivative;

$R^{53}$ and $R^{54}$ are each independently selected from the group consisting of Cl, OH, NH$_2$, an optionally substituted $C_1$-$C_6$ alkyl, an optionally substituted $C_1$-$C_6$ alkyloxy, an optionally substituted $C_1$-$C_6$ alkylamino, an optionally substituted $C_1$-$C_6$ acylamino, an optionally substituted aryloxy, an optionally substituted phosphate, an optionally substituted phosphonate, and an optionally substituted heteroaryloxy; or $R^{53}$ is optionally linked with $R^{51}$, $R^{54}$, or $R^{56}$ to form an optionally substituted 5-, 6-, or 7-membered heterocycle;

$R^{55}$ is selected from the group consisting of OH, NH$_2$, an optionally substituted $C_1$-$C_6$ alkyl, an optionally substituted $C_1$-$C_6$ alkyloxy, an optionally substituted $C_1$-$C_6$ alkylamino, an optionally substituted aryl, and an optionally substituted heteroaryl; or $R^{55}$ is optionally linked to $R^{51}$ or $R^{56}$ to form an optionally substituted ring;

$R^{56}$ is selected from the group consisting of H, a $C_1$-$C_6$ alkyl, and a $C_1$-$C_6$ heteroalkyl;

M is a biological agent or part of a biological agent or a prodrug of a biological agent;

$X^5$ is O or $NR^{56}$;

n is 0, 1, 2, or 3;

or a stereoisomer or a pharmaceutically acceptable salt thereof.

Some embodiments relate to a compound of Formula VIa, VIb or VIc:

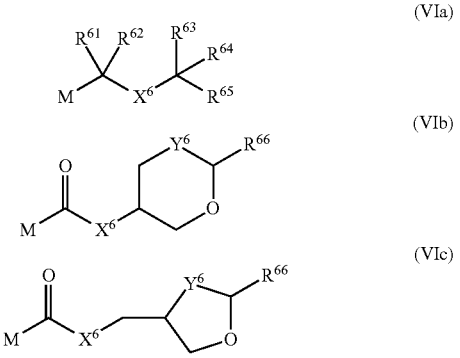

wherein:

$R^{61}$ and $R^{62}$ are each independently selected from the group consisting of H, an optionally substituted $C_1$-$C_6$ alkyloxy, an optionally substituted $C_1$-$C_6$ alkylamino, an optionally substituted $C_1$-$C_6$ acyloxy, —OCH$_2$P(O)(R$^{69}$)$_2$, and an optionally substituted $C_1$-$C_6$ acylamino; or $R^{61}$ and $R^{62}$ together optionally form an oxo (=O) or its derivative;

$R^{63}$, and $R^{64}$, $R^{65}$ are each independently selected from the group consisting of H, CO$_2$R$^{67}$, C(O)N(R$^{67}$)$_2$, P(O)(R$^{69}$)$_2$, an optionally substituted $C_1$-$C_6$ alkyl, an optionally substituted $C_1$-$C_6$ alkyloxy, an optionally substituted $C_1$-$C_6$ acyloxy, and an optionally substituted $C_1$-$C_6$ hereroalkyl; or two of $R^{63}$, $R^{64}$, and $R^{65}$ are optionally linked to form an optionally substituted ring; or $R^{63}$ is optionally linked with $R^{68}$ to form an optionally substituted ring; with the proviso that CR$^{63}$R$^{64}$R$^{65}$ is not a straight chain $C_1$-$C_4$ alkyl when $R^{61}$ and $R^{62}$ form an oxo (=O);

$R^{66}$ is selected from the group consisting of H, an optionally substituted $C_1$-$C_6$ alkyl, an optionally substituted $C_1$-$C_6$ alkyloxy, an optionally substituted $C_1$-$C_6$ heteroalkyl, an optionally substituted aryl, and an optionally substituted heteroaryl;

$R^{67}$ and $R^{68}$ are each independently selected from the group consisting of H, an optionally substituted $C_1$-$C_6$ alkyl, and an optionally substituted $C_1$-$C_6$ heteroalkyl;

$R^{69}$ is selected from the group consisting of OH, an optionally substituted $C_1$-$C_6$ alkyl, an optionally substituted $C_1$-$C_6$ alkyloxy, and an optionally substituted $C_1$-$C_6$ alkylamino;

M is a biological agent or part of a biological agent or a prodrug of a biological agent;

$X^6$ is O or $NR^{68}$;

$Y^6$ is selected from the group consisting of null, O, $NR^{68}$, and $C(R^{68})_2$;

or a stereoisomer or a pharmaceutically acceptable salt thereof.

Some embodiments relate to a compound of Formula VII:

wherein:

$R^{71}$ is selected from the group consisting of H, OH, an optionally substituted $C_1$-$C_6$ alkyl, an optionally substituted $C_1$-$C_6$ heteroalkyl, an optionally substituted $C_1$-$C_6$ alkyloxy, an optionally substituted phosphate, and an optionally substituted phosphonate;

$X^7$ is O or S;

$Y^7$ is N or $CR^{71}$;

M is a biological agent or part of a biological agent or a prodrug of a biological agent;

or a stereoisomer or a pharmaceutically acceptable salt thereof.

CYP3A4 is expressed in the liver in a level much higher than other tissues (DeWaziers et al. J Pharm Exp Ther 253:387 (1990)). Prodrug compounds of Formula I-VII are predominantly activated via CYP3A4 in the liver. In some embodiments, the prodrug compounds of Formulae I-VII have high efficiency in liver-targeting via selective delivery of biologically active agents to the liver. In some embodiments, the prodrugs are used to increase the therapeutic index of the drug, since the prodrug compounds of Formulae I-VII may not be active or may be less active outside the liver.

Certain drugs of phosph(on)ate derivatives are highly charged compounds that have generally poor oral bioavailability due to poor absorption in the gastrointestinal tract. Certain drugs are highly lipophilic compounds that have generally poor oral bioavailability due to poor absorption in the gastrointestinal tract. In some embodiments, the prodrug compounds of Formulae I-VII have oral bioavailability superior to the parent drugs/agents.

In some embodiments, due to the liver-targeting nature of the prodrug compounds of Formulae I-VII, the compounds are used to treat diseases that benefit from enhanced drug distribution to the liver and like tissues and cells, including but not limited to diseases in the liver, such as hepatitis, liver cancer, liver fibrosis, fatty liver, malaria, other viral and parasitic infections, and metabolic, cardiovascular, and/or hormonal diseases where the liver is involved in the production and/or the homeostasis control of the biochemical end products, e.g. glucose (diabetes); cholesterol, fatty acids, bile acids, triglycerides (hyperlipidemia) (atherosclerosis) (obesity), lipoproteins, apolipoproteins, and sex hormone-binding globulin (SHBG).

In some embodiments, the disclosed prodrugs are used to prolong pharmacodynamic half-life of the drug. In addition, the disclosed prodrug methodology can be used to achieve sustained delivery of the parent drug. In some embodiments, a method of making these prodrugs is described. In some embodiments, the prodrugs are also useful in the delivery of diagnostic imaging agents to the liver or other tissues.

Some compounds of Formulae I-VII have asymmetric centers where the stereochemistry is unspecified, and the diastereomeric mixtures of these compounds are included, as well as the individual stereoisomers when referring to a compound of Formulae I-VII generally.

Some embodiments of the compounds, compositions and methods provided herein include a pharmaceutical composition comprising a compound provided herein and a pharmaceutically acceptable carrier.

Some embodiments also include administering an effective amount of a second or multiple therapeutic agents in combination with a compound provided herein to the subject in need thereof.

Some embodiments of the compounds, compositions and methods provided herein include a method of treating a liver disease comprising administering an effective amount of a compound provided herein where M is a nucleoside antiviral or anticancer agent to a subject in need thereof.

Some embodiments of the compounds, compositions and methods provided herein include a method of treating dyslipidemia comprising administering an effective amount of a compound provided herein where M is a lipid modulator such as a HMG-CoA reductase inhibitor, a selective thyroid hormone receptor modulator, peroxisome proliferator-activated receptor modulator, a fibrate, nicotinic acid, and an omega-3 fatty acid to a subject in need thereof.

Some embodiments of the compounds, compositions and methods provided herein include a method of treating hyperglycemia comprising administering an effective amount of a compound provided herein where M is a glucose modulator such as peroxisome proliferator-activated receptor modulator, glucose biosynthesis inhibitor, and dipeptidyl peptidase 4 inhibitor to a subject in need thereof.

Some embodiments of the compounds, compositions and methods provided herein include a method of treating a hormonal condition comprising administering an effective amount of a compound provided herein where M is a nuclear hormone receptor modulator to a subject in need thereof.

In some embodiments, the subject is mammalian.

In some embodiments, the subject is human.

Some embodiments of the compounds, compositions and methods provided herein include a method of testing a compound in a cell comprising contacting the cell with the compound of the claims.

In some embodiments, the cell is in vivo.

In some embodiments, the cell is ex vivo.

In some embodiments, the cell is a hepatocyte.

In some embodiments, the cell is mammalian,

In some embodiments, the cell is human,

Some embodiments of the compounds, compositions and methods provided herein include use of a compound provided herein in the treatment of a disease in the liver.

Some embodiments include the use of a compound provided herein in combination with additional therapeutic agent(s) for the treatment of a disease in the liver.

Some embodiments of the compounds, compositions and methods provided herein include use of a compound provided herein in the treatment of a disease or condition by intervening in a molecular pathway in the liver.

Some embodiments include the use of a compound provided herein in combination with additional therapeutic agent(s) for the treatment of a disease or condition by intervening in a molecular pathway in the liver.

Definitions

In accordance with the present disclosure and as used herein, the following terms are defined with the following meanings, unless explicitly stated otherwise. It is to be understood that both the foregoing general description and the following detailed description are exemplary and explanatory only and are not restrictive of the subject matter claimed. In this application, the use of the singular includes the plural unless specifically stated otherwise. In this application, the use of "or" means "and/or" unless stated otherwise. Furthermore, use of the term "including" as well as other forms, such as "includes," and "included" is not limiting, As used herein, ranges and amounts can be expressed as "about" a particular value or range. "About" also includes the exact amount. Hence "about 10%" means "about 10%" and also "10%."

As used herein, "optional" or "optionally" means that the subsequently described event or circumstance does or does not occur, and that the description includes instances where the event or circumstance occurs and instances where it does not. For example, an optionally substituted group means that the group is unsubstituted or is substituted.

As used herein, the singular forms "a," "an" and "the" include plural referents unless the context clearly dictates otherwise. Thus, for example, reference to a composition comprising "a therapeutic agent" includes compositions with one or a plurality of therapeutic agents.

The term "alkyl" refers to saturated aliphatic groups including straight-chain, branched chain and cyclic groups, up to and including 10 carbon atoms. Suitable alkyl groups include methyl, ethyl, n-propyl, isopropyl, and cyclopropyl. The alkyl group may be optionally substituted with 1-3 substituents.

The term "optionally substituted" or "substituted" includes groups substituted by one to four substituents, independently selected from lower alkyl, lower aryl, lower aralkyl; lower cyclic alkyl, lower heterocycloalkyl; hydroxy, lower alkoxy, lower aryloxy, perhaloalkoxy, aralkoxy, lower heteroaryl, lower heteroaryloxy, lower heteroarylalkyl, lower heteroaralkoxy, azido, amino, halogen, lower alkylthio, oxo, lower acylalkyl, lower carboxy esters, carboxyl, carboxamido, nitro, lower acyloxy, lower aminoalkyl, lower alkylaminoaryl, lower alkylaryl, lower alkylaminoalkyl, lower alkoxyaryl, lower arylamino, lower aralkylamino, lower alkylsulfonyl, lower carboxamidoalkylaryl, lower carboxamidoaryl, lower hydroxyalkyl, lower haloalkyl, lower alkylaminoalkylcarboxy, lower aminocarboxamidoalkyl, cyano, lower alkoxyalkyl, tower perhaloalkyl, phosphate, phosphonate, or phosphoramidate, and lower arylalkyloxyalkyl. "Substituted aryl" and "substituted heteroaryl" refers to aryl and heteroaryl groups substituted with 1-6 substituents. These substituents are selected from the group consisting of lower alkyl., lower alkoxy, lower perhaloalkyl, halogen, hydroxy, cyano, and amino.

The term "heteroalkyl" refer to alkyl groups containing at least one heteroatom, such as 1 to 3 heteroatoms. Suitable heteroatoms include oxygen, sulfur, and nitrogen.

The term "heteroacyl" refer to —C(O)-heteroalkyl groups.

The term "acyloxy" refers to —OC(O)R where R is alkyl, or heteroalkyl.

The term "alkoxy" or "alkyloxy" refers to OR where R is alkyl, or heteroalkyl; all optionally substituted.

The term "carboxyl" refers to C(O)OH.

The term "oxo" refers to an =O group.

The term "oxo derivative" refers to =NR where R is H, lower alkyl, lower alkoxyl, or lower alkylamino.

The term "amino" refers to NRR' where R and R' are each independently selected from hydrogen, alkyl, aryl, aralkyl and heterocycloalkyl, all except H are optionally substituted; and R and R' can form a cyclic ring system.

The term "acylamino" refers to —NRC(O)R' where R and W are each independently selected from H, alkyl, or heteroalkyl.

The term "halogen" or "halo" refers to F, Cl, Br and I.

The term "haloalkyl" refer to alkyl groups containing at least one halogen, in a further aspect are 1 to 3 haloatoms. Suitable haloatoms include F, Cl, and Br.

The term "haloheteroalkyl" refer to alkyl groups containing at least one halogen and one heteroatom.

The term "haloacyl" refer to —C(O)-haloalkyl, groups.

The term "haloheteroacyl" refer to —C(O)-haloheteroalkyl groups.

The term "alkenyl" refers to unsaturated groups which have 2 to 12 atoms and contain at least one carbon carbon double bond and includes straight chain, branched chain and cyclic groups. Alkenyl groups may be optionally substituted. Suitable alkenyl groups include allyl.

The term "alkynyl" refers to unsaturated groups which have 2 to 12 atoms and contain at least one carbon carbon triple bond and includes straight chain, branched chain and cyclic groups. Alkynyl groups may be optionally substituted. Suitable alkynyl groups include ethynyl.

The term "methylene" refers to =CH$_2$.

The term "methylene derivative" refers to =CRR' where R and R' are each independently selected from an optionally substituted alkyl, an optionally substituted alkenyl, and M.

The term "aminoalkyl" refers to the group NR$_2$-alkyl where R is selected from H, alkyl, aryl, aralkyl, and heterocycloalkyl.

The terms "alkylthio" refers to the group alkyl-S—.

The term "amido" refers to NR$_2$ group next to an acyl or sulfonyl group as in NR$_2$C(O)—, RC(O)NR—, NR$_2$S(=O)$_2$— and RS(=O)$_2$—NR—, where R includes H, alkyl, aryl, aralkyl, and heterocycloalkyl.

The term "perhalo" refers to groups wherein every C—H bond has been replaced with a C-halo bond on an aliphatic or aryl group. Suitable perhaloalkyl groups include CF$_3$ and CFCl$_2$.

The term "aryl" refers to an aromatic group wherein each of the atoms forming the ring is a carbon atom. Aryl rings may be formed by five, six, seven, eight, nine, or more than nine carbon atoms. Aryl groups may be optionally substituted. Examples of aryl groups include, but are not limited to phenyl, naphthalenyl, phenanthrenyl, anthracenyl, tetralinyl, fluorenyl, indenyl, and indanyl.

The term "heteroaryl" refers to an aromatic group wherein at least one atom forming the aromatic ring is a heteroatom. Heteroaryl rings may be formed by three, four, five, six, seven, eight, nine, or more than nine atoms. Heteroaryl groups may be optionally substituted. Examples of heteroaryl groups include, but are not limited to, aromatic C$_{3-8}$ heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In some embodiments, heteroaryl groups are optionally substituted with one or more substituents, independently selected from halo, hydroxy, amino, cyano, nitro, alkylamido, acyl, C$_{1-6}$-alkoxy, C$_{1-6}$-alkyl, C$_{1-6}$-hydroxyalkyl, C$_{1-6}$-aminoalkyl, C$_{1-6}$-alkylamino, alkylsulfenyl, alkylsulfinyl, alkylsulfonyl, sulfamoyl, or trifluoromethyl. Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,24-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—C$_{1-6}$-alkyl, C$_{1-6}$-alkyl, hydroxy-C$_{1-6}$-alkyl, and amino-C$_{1-6}$-alkyl.

The term "aryloxy" refers to —O-aryl.

The term "heteroaryloxy" refers to —O-heteroaryl.

The phrase "therapeutically effective amount" means an amount of a compound or a combination of compounds that partially or fully ameliorates, attenuates or eliminates one or more of the symptoms of a particular disease or condition or prevents, modifies, or delays the onset of one or more of the symptoms of a particular disease or condition. Such amount can be administered as a single dosage or can be administered according to a regimen, whereby it is effective. Repeated administration may be needed to achieve a desired result (e.g., treatment of the disease and/or condition).

The term "pharmaceutically acceptable salt" includes salts of compounds of Formulae I-VII and its prodrugs derived from the combination of a compound of the present embodiments and an organic or inorganic acid or base. Suitable acids include acetic acid, adipic acid, benzenesulfonic acid, (+)-7,7-dimethyl-2-oxobicyclo[2.2.1]heptane-1-methanesulfonic acid, citric acid, 1,2-ethanedisulfonic acid, dodecyl sulfonic acid, fumaric acid, glucoheptonic acid, gluconic acid, glucuronic acid, hippuric acid, hydrochloride hemiethanolic acid, HBr, HCl, HI, 2-hydroxyethanesulfonic acid, lactic acid, lactobionic acid, maleic acid, methanesulfonic acid, methylbromide acid, methyl sulfuric acid, 2-naphthalenesulfonic acid, nitric acid, oleic acid, 4,4'-methylenebis-[3-hydroxy-2-naphthalenecarboxylic acid], phosphoric acid, polygalacturonic acid, stearic acid, succinic acid, sulfuric acid, sulfosalicylic acid, tannic acid, tartaric acid, terphthalic acid, and p-toluenesulfonic acid. Suitable bases include NaOH, KOH, Ca(OH)$_2$, Zn(OH)$_2$, Mg(OH)$_2$, diethylamine, ethanolamine, diethanolamine, choline, lysine, meglumine, benzathine, and tromethamine.

The term "spacer" refers to an atom or group of atoms that separate two or more groups from one another by a desired number of atoms. For example, in some embodiments, it may be desirable to separate two or more groups by one, two, three, four, five, six, or more than six atoms. In such embodiments, any atom or group of atoms may be used to separate those groups by the desired number of atoms. Spacers are optionally substituted. In some embodiments, a spacer comprises saturated or unsaturated alkyls, heteroalkyls and/or haloalkyls. In some embodiments, a spacer comprises atoms that are part of a ring, Where the number of any given substituent is not specified (e.g., "haloalkyl"), there may be one or more substituents present. For example, "haloalkyl" can include one or more of the same or different halogens. For example, "haloalkyl" includes each of the substituents $CF_3$, $CHF_2$ and $CH_2F$.

Solely for the purposes of illustration, and without limiting, the above definitions, some examples of spacers are provided. Examples of 2 atom spacers include, but are not limited to, the following:

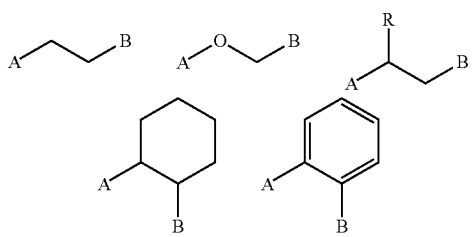

where A and B represent groups which are separated by the desired number of atoms.

Examples of 3 atom spacers include, but are not limited to, the following:

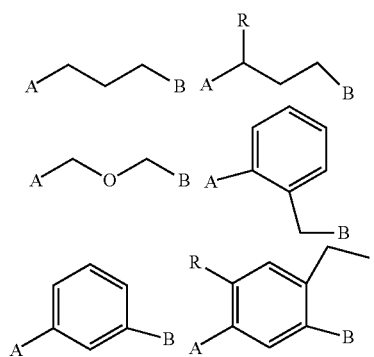

where A and B represent groups which are separated by the desired number of atoms.

The term "patient" refers to an animal being treated including a mammal, such as a dog, a cat, a cow, a horse, a sheep, and a human. In some embodiments the patient is a mammal, either male or female. In some embodiments, the patient is a male or female human.

The term "prodrug" as used herein refers to any compound that when administered to a biological system generates a biologically active compound as a result of spontaneous chemical reaction(s), enzyme catalyzed chemical reaction(s), and/or metabolic chemical reaction(s), or a combination of each. Standard prodrugs are formed using groups attached to functionality, e.g. HO—, HS—, HOOC—, $HOOPR_2$—, associated with the drug, that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are examples, not exhaustive, and one skilled in the art could prepare other known varieties of prodrugs. Such prodrugs of the compounds of Formula I fall within this scope. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, pharmacodynamic half-life, etc. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site specific delivery of the compound.

The term "stereoisomer" refers to the relative or absolute spatial relationship of the R group(s) and the substituent attached to the phosphorus atom via an exocyclic single bond on the 2-oxo-phosphorus prodrug ring, and refers to individual or any combination of the individual isomers such as a racemic mixture and a diastereomeric mixture. When one R group is attached to the carbon atom in the ring, there are four stereoisomers. For example, the structures A, B, C, and D below show four possible individual isomers. Structures A and D (or B and C) are a pair of two enantiomers (or called optical isomers). When two R groups attached to two different carbon atoms in the ring, there are eight possible stereoisomers.

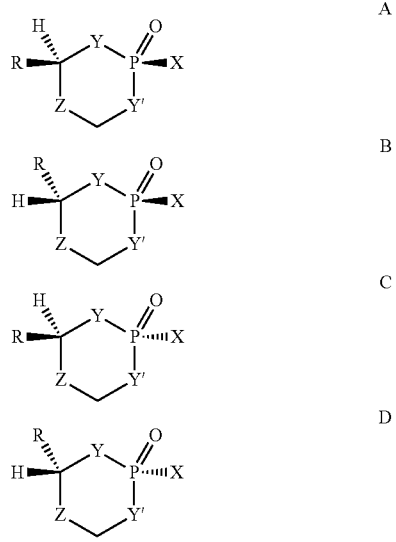

The term "liver" refers to the liver organ.
The term "liver specificity" refers to the ratio:

$$\frac{[\text{drug or drug metabolite in liver tissue}]}{[\text{drug or a drug metabolite in blood or another tissue}]}$$

as measured in animals treated with the drug or a prodrug. The ratio can be determined by measuring tissue levels at a specific time or may represent an AUC (area under a curve) based on values measured at three or more time points.

The term "increased or enhanced liver specificity" refers to an increase in liver specificity ratio in animals treated with the prodrug relative to animals treated with the parent drug.

Compounds disclosed in U.S. Pat. Nos. 8,063,025, 7,666, 85.5, and PCT Pub. No. WO2009/073506, are designed for the liver-specific delivery of nucleosides for the treatment of HCV patients and take advantage of a cytochrome P450 enzyme that is mainly expressed in the liver.

The term "enhanced oral bioavailability" refers to an increase of at least about 50% of the absorption of the dose of the parent drug. In an additional aspect, the increase in oral bioavailability of the prodrug (compared to the parent drug) is at least about 100%, or a doubling of the absorption. Measurement of oral bioavailability usually refers to measurements of the prodrug, drug, or drug metabolite in blood, plasma, tissues, or urine following oral administration compared to measurements following parenteral administration.

The term "therapeutic index" refers to the ratio of the dose of a drug or prodrug that produces a therapeutically beneficial response relative to the dose that produces an undesired response such as death, an elevation of markers that are indicative of toxicity, and/or pharmacological side effects.

The term "sustained delivery" refers to an increase in the period in which there is a prolongation of therapeutically-effective drug levels due to the presence of the prodrug.

The terms "treating" or "treatment" of a disease includes inhibiting the disease (slowing or arresting or partially arresting its development), providing relief from the symptoms or side effects of the disease (including palliative treatment), and/or relieving the disease (causing regression of the disease).

The terms "biological agent" refers to a compound that has biological activity or that has molecular properties that can be used for diagnosis purpose, such as a compound carrying a radioactive isotope or a heavy atom.

The terms "molecular pathway" refers to a series of molecular events in tissues such as a receptor modulating sequence or a biosynthesis sequence that is involved in physiological or pathophysiological functions of a living animal.

The terms "vinyl ketone reactive intermediate" refers to compounds of the structure below that are chemically reactive to generate a covalent bond with a molecular entity in the tissues or cell, where R is H, alkyl, aryl, or heteroaryl.

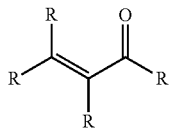

Formulations

The disclosed compounds may be used alone or in combination with other treatments. These compounds, when used in combination with other agents, may be administered as a daily dose or an appropriate fraction of the daily dose (e.g., bid). The compounds may be administered after a course of treatment by another agent, during a course of therapy with another agent, administered as part of a therapeutic regimen, or may be administered prior to therapy by another agent in a treatment program.

Examples of pharmaceutically acceptable salts include acetate, adipate, besylate, bromide, camsylate, chloride, citrate, edisylate, estolate, fumarate, gluceptate, gluconate, glucuronate, hippurate, hyclate, hydro bromide, hydrochloride, iodide, isethionate, lactate, lactobionate, maleate, mesylate, methylbromide, methylsulfate, napsylate, nitrate, oleate, palmoate, phosphate, polygalacturonate, stearate, succinate, sulfate, sulfosalicylate, tannate, tartrate, terphthalate, tosylate, triethiodide, sodium, potassium, calcium, zinc, magnesium, diethylamine, ethanolamine, diethanolamine, cholinate, lysine, meglumine, benzathine, and tromethamine.

Compositions containing the active ingredient may be in any form suitable for the intended method of administration. In some embodiments, the compounds of a method and/or composition described herein can be provided via oral administration, rectal administration, transmucosal administration, intestinal administration, enteral administration, topical administration, transdermal administration, intrathecal administration, intraventricular administration, intraperitoneal administration, intranasal administration, intraocular administration and/or parenteral administration.

When the compounds are administered via oral administration, for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient can be mixed with an inert solid diluent, for example calcium phosphate or kaolin, or as soil gelatin capsules wherein the active ingredient can be mixed with water or an oil medium, such as peanut oil, liquid paraffin or olive oil.

Formulations suitable for parenteral administration include aqueous and non-aqueous isotonic sterile injection solutions which may contain, for example, antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

In some embodiments unit dosage formulations contain a daily dose or unit, daily sub-dose, or an appropriate fraction thereof, of a drug. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Synthesis of compounds

The following procedures for the preparation of the cyclic prodrug compounds illustrate the general procedures used to prepare the compounds which apply to phosphate, phosphonate, phosphoramidate, carboxylic acid, and alcohol containing drugs. Prodrugs can be introduced at different stages of synthesis of a drug. In some embodiments, they are made at a later stage, because of the general sensitivity of these groups to various reaction conditions. Optically pure prodrugs containing a single isomer at the phosphorus center can be made, for example, by separation of the diastereomers by a combination of column chromatography and/or crytallization, or by enantioselective synthesis of chiral activated phosph(on)ate intermediates.

Scheme I describes general strategies of synthesis of the cyclic phosph(on)ate prodrug compounds of Formula I. The first strategy starts with treatment of a dihydroxyl compound of structure 1 where Z is not a heteroatom with phosphorus oxychloride to generate a cyclic phosphate of structure 2. A coupling reaction of a cyclic phosphate chloride of structure 2 with an alcohol derivative compound of structure 3 provides the final compound of structure 4. When Z is a heteroatom, an alternative strategy can be used where the alcohol compound of structure 3 is converted to its monophosphate of structure 5 via a two-step sequence of phosphorylation with phosphorus oxychloride and acid hydrolysis by a resin. The monophosphate of structure 5 is then treated with a dichloro compound of structure 6 in the presence of silver nitrate to give the final product of structure 4.

phosphorus oxychloride provides the cyclic phosphoramidate of structure 8. A biological agent having a hydroxyl group of structure 3 is coupled with a prodrug intermediate of structure 8 to yield the final product of structure 9. Alternatively, a chloroamino compound of structure 10 (where Z is a heteroatom) is treated with phosphorus oxychloride and then an ion-exchange resin sequentially to give the intermediate of structure 11 that undergoes an internal cyclization followed by chlorination to the cyclic phosphoramidate of structure 8.

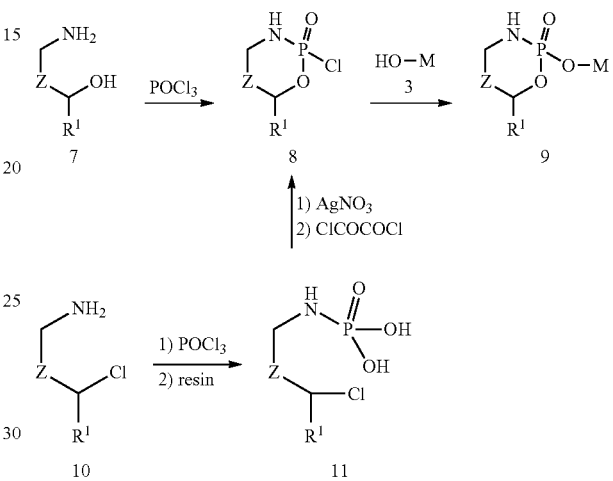

Scheme III describes general synthetic procedures of the 2-oxodioxazaphinine prodrugs of Formula I. A biological

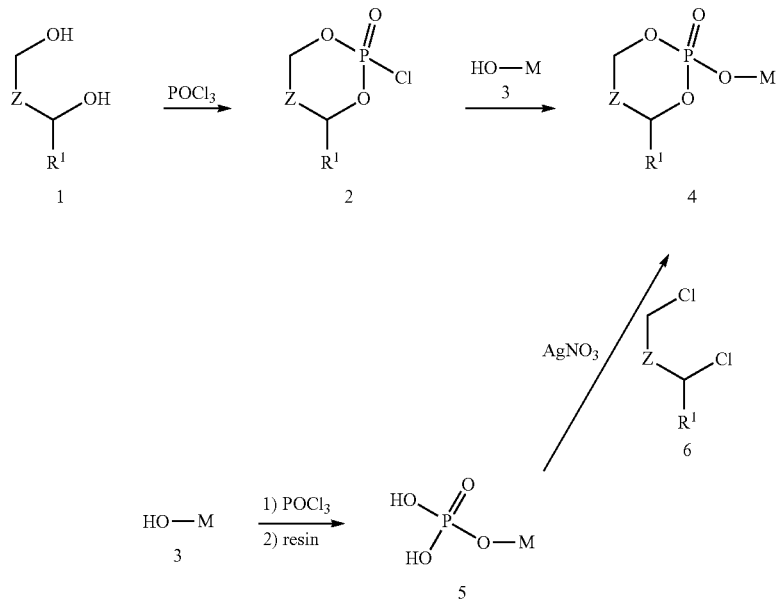

Scheme II describes general strategies of synthesis of cyclic phosphoramidate or phosphonamidate prodrug compounds of Formula I. Treatment of the hydroxylamino compounds of structure 7 (where Z is not a heteroatom) with agent derivative of structure 12 is treated with phosphorus oxychloride to provide an intermediate of structure 13 that is then treated with a base in the presence of an aldehyde of structure 14 to give final product of structure 15. The regioisomers of structure 15 are made from a different route where a compound of structure 16 is treated sequentially with diphenyl phosphate under basic a condition to give an intermediate of structure 17. Base mediated internal cyclization of the intermediate of structure 17 affords the final product of structure 18.

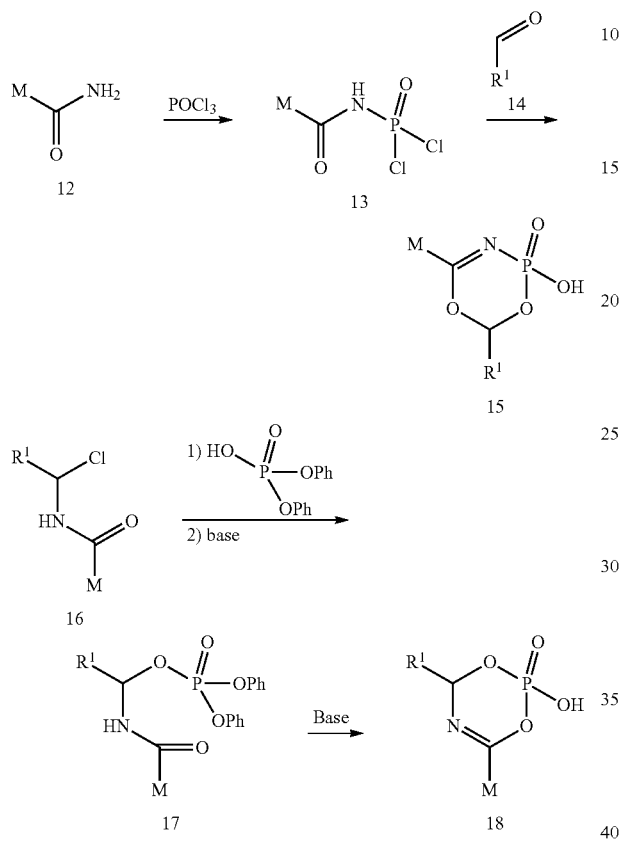

Scheme IV describes general synthetic procedures of the prodrugs of Formula IIa. Benzaldehyde derivative of structure 19 is treated with phosphorus oxychloride to provide an intermediate of structure 20 that is then converted to structure 21 in the presence of a acid chloride derivative of a biologic agent with zinc chloride as the catalyst. Deprotection followed by treatment of a base affords the final product of structure 22.

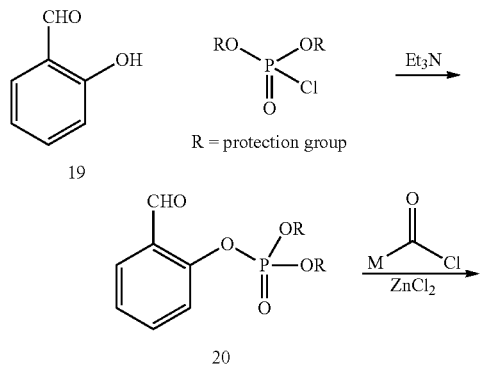

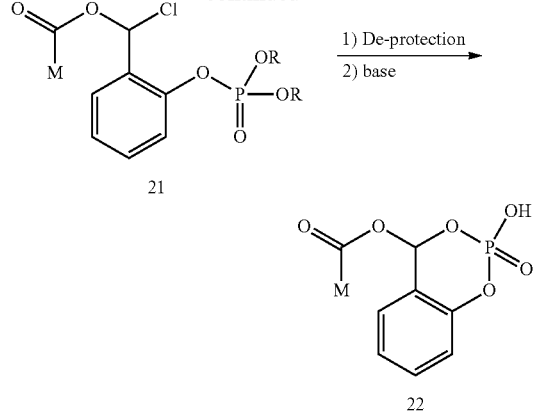

Scheme V describes a procedure for preparing cyclic bisphosphonate prodrug compounds of Formula III via either an acid catalyzed condensation or a base catalyzed alkylation routes. Condensation reaction of a bisphosphonate of structure 23 with an aldehyde of structure 24 in the presence of an acid catalyst affords a product of structure 25. Alternatively, alkylation of a bisphosphonate of structure 23 with a halide compound of structure 26 in the presence of silver nitrate and/or a base provides the same product of structure 25.

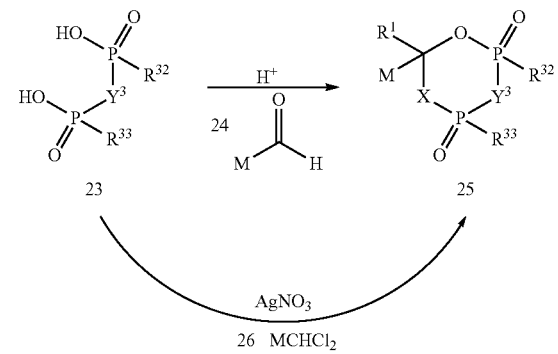

Scheme VI describes general strategies of synthesis of the cyclic acetal prodrug compounds of Formula IV. The dihydroxyl compound of structure 1 is condensed with an aldehyde of structure 2 in the presence of catalytic amount of acid to give a product of structure 3. Aldehyde compound of structure 2 is prepared from the corresponding carboxylic acid by the standard procedure in the literature.

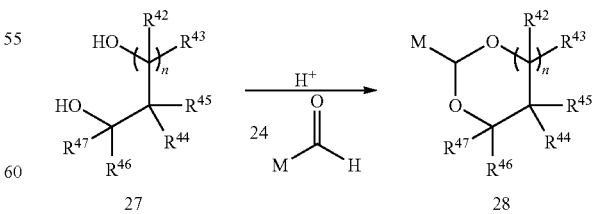

Compounds of Formula V-VII are prepared by using standard conditions in the literature from the corresponding acids and derivatives (e.g., See J. E. Starrett, Jr., et al. J Med Chem 37:1857-1864 (1994) and J. K. Dickson, et al. J Med Chem 39:661-664 (1996)).

EXAMPLES

It will be understood that the following are examples and that the present embodiments are not limited to these examples.

Some biologically active compounds of Formulae I-VII are prepared as outlined below. Some biologically nonactive compounds of Formulae I-VII are also prepared to demonstrate the synthetic methodologies as outlined below.

Example 1

(2R,3R,4R,5R)-2-(((7-Chloro-3-oxido-1,5-dihydrobenzo[e][1,3,2]dioxaphosphepin-3-yl)methyl)-5-(2,4-dioxo-3,4-dihydropyrimidin-1(2H)-yl)-4-fluoro-4-methyltetrahydrofuran-3-yl propionate (Compound 101)

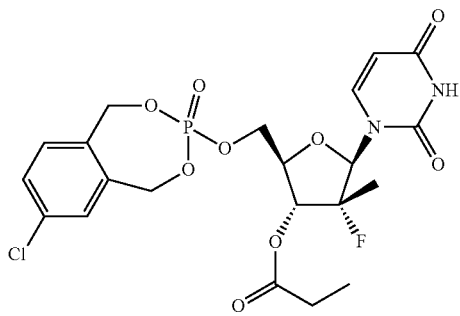 [SMILES: CCC(=O)O[C@@H]1[C@@H](COP2(=O)OCc3ccc(Cl)cc3CO2)O[C@@H](n2ccc(=O)[nH]c2=O)[C@]1(C)F]

Compound 101 was prepared as a mixture of two diastereomers according to synthetic strategy of Scheme I from (4-chloro-1,2-phenylene)dimethanol and the nucleoside derivative. [M+H]$^+$ calcd for $C_{21}H_{23}ClFN_2O_9P$: 533.08; found: 533.1. $^1$H NMR (400 MHz, DMSO-d$_6$) 11.60 (s, 1H), 7.74 (d, J=8.4, 1H), 7.66 (dd, J=4.8 and 1.6, 1H), 7.56-7.52 (m, 2H), 6.08 (bs, 1H), 5.72 (d, J=8.4, 1H), 5.40-5.10 (m, 4H), 4.45-4.31 (m, 3H ), 3.41-3.31 (m, 1H), 2.46 (q, J=7.6, 2H), 1.33 (d, J=22.8, 3H), and 1.06 (t, J=7.6, 3H).

Example 2

(2R,3R,4R,5R)-2-(((4-(3-Chlorophenyl)-2-oxido-1,3,5,2-trioxaphosphinan-2-yl)oxy)methyl)-5-(2,4-dioxo-3,4-dihydropyrimidin-1(2H)-yl)-4-fluoro-4-methyltetrahydrofuran-3-yl acetate (Compound 102)

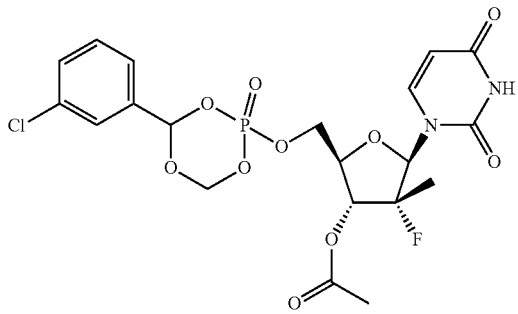 [SMILES: CC(=O)O[C@@H]1[C@@H](COP2(=O)OCOC(c3cccc(Cl)c3)O2)O[C@@H](n2ccc(=O)[nH]c2=O)[C@]1(C)F]

Compound 102 can be prepared according to synthetic strategy of Scheme I from 3-chlorobenzaldehyde and the nucleoside derivative. MH$^+$=534.06 (Calc.).

Example 3

(2R,3R,4R,5R)-2-(((6-(3-Chlorophenyl)-5,5-dimethyl-2-oxido-1,3,2-oxazaphosphinan-12-yl)oxy)methyl)-5-(2,4-dioxo-3,4-dihydropyrimidin-1(2H)-yl)-4-fluoro-4-methyltetrahydrofuran-3-yl acetate (Compound 103)

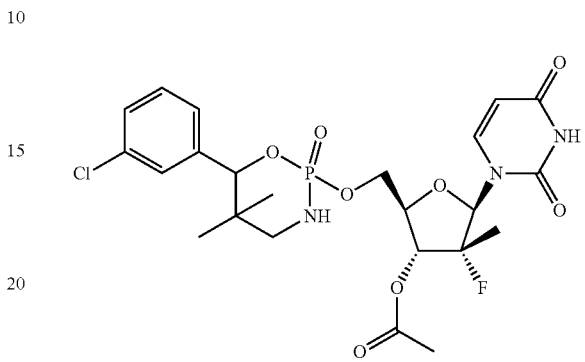

Compound 103 was prepared as a 1:1 mixture of two diastereomers according to synthetic strategy of Scheme II from 3-amino-1-(3-chlorophenyl)-2,2-dimethylpropan-1-ol and the nucleoside derivative. [M+H]$^+$ calcd for $C_{23}H_{28}ClFN_3O_8P$: 561.13; found: 561.2. $^1$H NMR (400 MHz, DMSO-d$_6$) 11.60 (s, 0.5H), 11.50 (s, 0.5H), 7.80-7.20 (m, 5H), 6.02 (bs, 1H), 5.55-5.50 (m, 1H), 5.40 (s, 1H), 4.38-4.02 (m, 5H), 2.13 (s, 3H), 1.34 (d, J=15.5, 1.5H), 1.28 (d, J=15.5, 1.5H), 0.92 (s, 3H, and 0.73 (s, 3H).

Example 4

(2R,3R,4R,5R)-2-(((5-(3-Chlorophenyl)-1-isopropyl-2-oxido-1,3,2-oxazaphospholidin-2-yl)oxy)methyl)-5-(2,4-dioxo-3,4-dihydropyrimidin-1(2H)-yl)-4-fluoro-4-methyltetrahydrofuran-3-yl acetate (Compound 104)

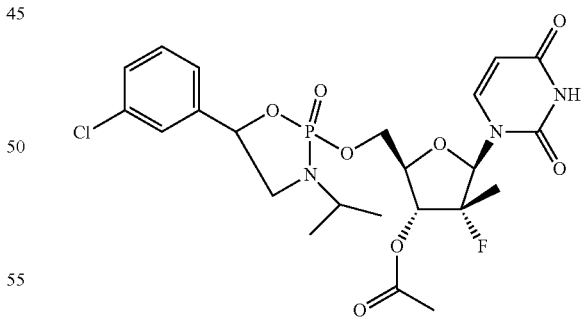

Compound 104 was prepared as a mixture of two diastereomers according to synthetic strategy of Scheme II from 2-isopropylamino-1-(3-chlorophenyl)ethan-1-ol and the nucleoside derivative, [M+11]$^+$calcd for $C_{23}H_{28}ClFN_3O_8P$: 560.13; found: 560,2. $^1$14 NMR (400MHz, DMSO-d$_6$) 11.59 (s, 1H), 7.70-7.60 (m, 1H), 7.50 (d, J=9.6, 1H), 7.44-7.40 (m, 314), 6.10 (bs, 1H), 5.59-5.56 (m, 1H), 5.45 (bs, 1111), 5.22 (bs, 1H), 4.40-4.16 (m, 3H), 3.90-3.72 (m, 1H), 3.40 9bs, 1H), 3.1_4 (bs, 1H), 2.14 (s, 3H), and 1.38-1.12 (m, 9H).

Example 5

2-Ethoxy-4,6-di(pyridine-3-yl)-1,5,3,2-dioxazaphosphinine 2-oxide (Compound 105)

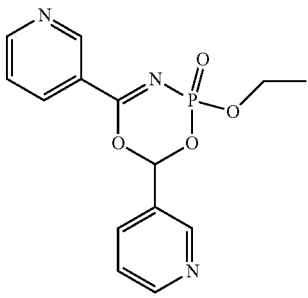 [SMILES: CCOP1(=O)N=C(c2cccnc2)OC(c2cccnc2)O1]

Compound 105 can be prepared according to synthetic strategy of Scheme II from nicotinic acid and pyridine-3-aldehyde. MH$^+$=319.07 (Calc.).

Example 6

(2R,3R,4R,5R)-2-(((7-(3-chlorophenyl)-4-methyl-2-oxido-1,3,4,2-dioxazaphosphepan-2-yl)oxy)methyl)-5-(2,4-dioxo-3,4-dihydropyrimidin-1(2H)-yl)-4-fluoro-4-methyltetrahydrofuran-3-yl acetate (Compound 106)

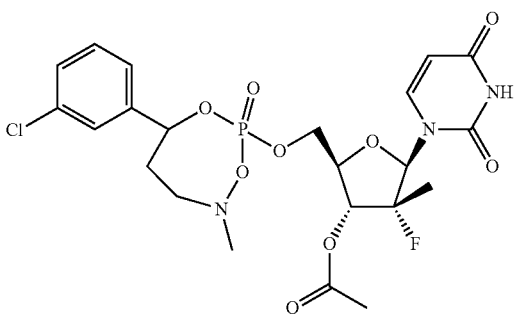 [SMILES: CC(=O)O[C@@H]1[C@@H](COP2(=O)OC(c3cccc(Cl)c3)CCN(C)O2)O[C@@H](n2ccc(=O)[nH]c2=O)[C@]1(C)F]

Compound 106 was prepared as a mixture of two diastereomers according to synthetic strategy of Scheme II from 4-hydroxy-1-(3-chlorophenyl)butan-1-ol and the nucleoside derivative, [M+H]$^+$ calcd for C$_{22}$H$_{25}$ClFN$_2$O$_9$P: 562.11; found: 562.2. $^1$H NMR (400 MHz, DMSO-d$_6$) 11.56 (s, 1H), 7.76 (d, J=8.4, 1H), 7.45-7.35 (m, 4H), 6.15 (m, 1H), 5.66 (t, J=4.4, 1H), 5.38-5.22 (m, 2H), 3.25 (bs, 1H), 2.95-2.88 (m, 1H), 2.81 (s, 1.5H), 2.79 (s, 1.5H), 2.14 (s, 3H), 2.05-1.60 (m, 4H), and 1.33 (d, J=23, 3H).

Example 7

(1S,3R,7S,8S,8aR)-3,7-dimethyl-8-(2-((2S,4R)-4-((2-oxido-4,6-di(pyridin-3-yl)-1,5,3,2-dioxazaphosphinin-2-yl)oxy)-6-oxotetrahydro-2H-pyran-2-yl)ethyl)-1,2,3,7,8,8a-hexahydronaphthalen-1-yl 2,2-dimethylbutanoate (Compound 107)

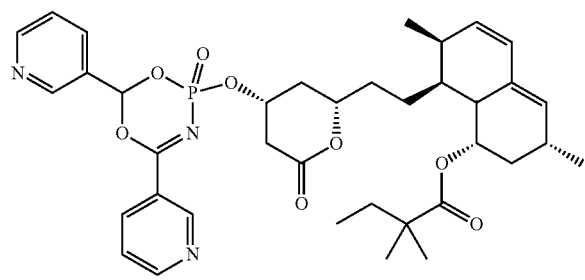

Compound 107 can be prepared according to synthetic strategy of Scheme II from nicotinic acid, pyridine-3-aldehyde, and simvastatin. MH-$^+$=691.30 (Calc.).

Example 8

(2R,3R,4R,5R)-2-(((4-(3-Chlorophenyl)-2-oxido-1,3,2-dioxaphosphepan-2-yl)oxy)methyl)-5-(2,4-dioxo-3,4-dihydropyrimidin-1(2H)-yl)-4-fluoro-4-methyltetrahydrofuran-3-yl acetate (Compound 108)

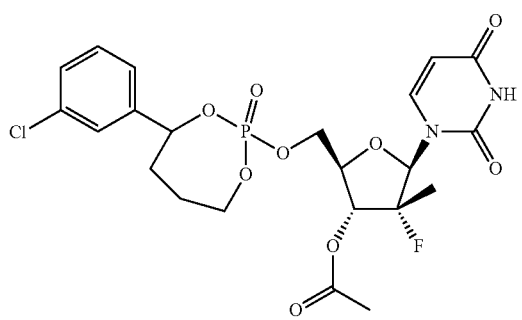 [SMILES: CC(=O)O[C@@H]1[C@@H](COP2(=O)OCCCC(c3cccc(Cl)c3)O2)O[C@@H](n2ccc(=O)[nH]c2=O)[C@]1(C)F]

Compound 108 was prepared as a mixture of two diastereomers according to synthetic strategy of Scheme II from 4-hydroxy-1-(3-chlorophenyl)butan-1-ol and the nucleoside derivative. [M+H]$^+$ calcd for C$_{22}$H$_{25}$ClFN$_2$O$_9$P: 547.1; found: 547.2. $^1$H NMR (400 MHz, DMSO-d$_6$) 11.58 (s, 1H), 7.75-7.38 (m, 5H), 6.05-5.20 (m, 4H), 4.43-4.03 (m, 5H), 2.14 (s, 3H), 2.10-1.90 (m, 3H), 1.34 (d, J=22, 1.5H), and 1.27 (d, J=22, 1.5H).

Example 9

2-Hydroxy-2-oxido-4H-benzo[d][1,3,2]dioxaphosphinin-4-yl acetate (Compound 109)

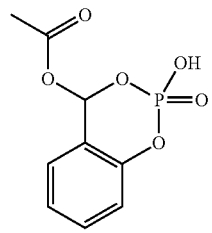 [SMILES: CC(=O)OC1OP(=O)(O)Oc2ccccc21]

Compound 109 was prepared according the general procedure described in Scheme IV as a diisopropylethylamine salt from 2-hydroxybenzaldehyde using benzyl as protection group. [M–H]$^+$ calcd for C$_9$H$_9$O$_6$P: 243.01; found: 243.00.

Example 10

2,4-Dihydroxy-6-phenethyl-1,5,2,4-dioxadiphospinane 2,4-dioxide (Compound 110)

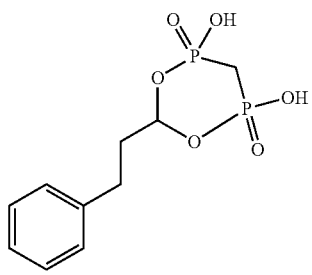 [SMILES: O=P1(O)CP(=O)(O)OC(CCc2ccccc2)O1]

Compound 110 was prepared according to the general procedure of Scheme V as a triethylamine salt from 3-phenylpropanal and methylenebis(phosphonate). [M+H]+ calcd for $C_{10}H_{14}O_6P_2$: 293.03; found: 293.05. $^1$H NMR (300 MHz, CD$_3$OD) 7.28-7.06 (m, 5H), 5.67-5.57 (m, 1H), 3.17 (q, J=7.4, 6H), 2.76 (t, J=8.1, 2H), 2.38 (t, J=28, 2H), 2.07-1.92 (m, 2H), and 1.29 (t, J=7.4, 9H).

Example 11

2,4-Dihydroxy-6-phenethyl-1,3,5,2,4-trioxadiphosphinane 2,4-dioxide (Compound 111)

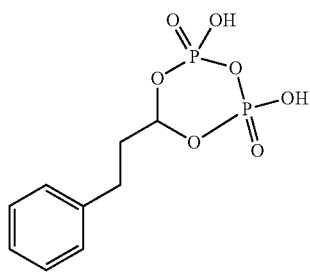 [SMILES: O=P1(O)OC(CCc2ccccc2)OP(=O)(O)O1]

Compound 111 was prepared according to the general procedure of Scheme V as a triethylamine salt from 3-phenylpropanal and pyrophosphate, [M+H]+ calcd for $C_9H_{12}O_7P_2$: 295.01; found: 295.15. $^1$H NMR (400 MHz, CD$_3$OD) 7.30-7.12 (m, 5H), 5.33 (t, J=4.5, 1H), 3.19 (q, J=7.4, 6H), 2.75 (t, J=7.5, 2H), 2.08-1.95 (m, 2H), and 1.30 (t, J=7.4, 9H).

Example 12

1-(Hydroxy(phosphonooxy)phosphoryl)oxy)-3-phenylpropyl acetate (Compound 112)

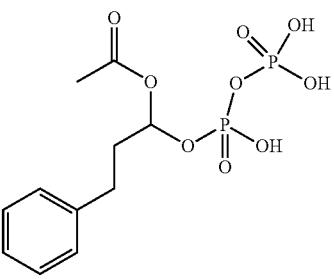 [SMILES: CC(=O)OC(CCc1ccccc1)OP(=O)(O)OP(=O)(O)O]

Compound 112 was prepared according to the general procedure of Scheme V as a triethylamine salt from 1-chloro-3-phenylpropyl acetate and pyrophosphate. [M+H]+ calcd for $C_{11}H_{16}O_7P_2$: 355.03; found: 356.90. $^1$H NMR (400 MHz, CD$_3$OD) 7.28-7.12 (m, 5H), 6.60-6.52 (m, 1H), 3.17 (q, J=7.4, 12H), 2.80-2.72 (m, 2H), 2.16-2.04 (m, 2H), 2.04 (s, 3H), 1.30 (t, J=7.4, 18H).

Example 13

3-Phenylpropane-1,1-diyl bis(trihydrogen diphosphate) (Compound 113)

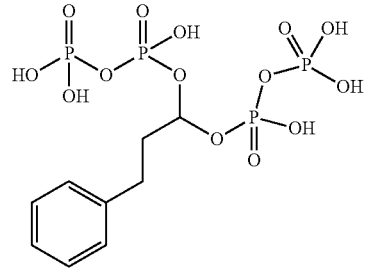 [SMILES: O=P(O)(O)OP(=O)(O)OC(CCc1ccccc1)OP(=O)(O)OP(=O)(O)O]

Compound 11.3 was prepared according to the general procedure of Scheme V as a diisopropylethylamine salt from 1-chloro-3-phenylpropyl acetate and pyrophosphate. [M+H]+ calcd for $C_9H_{16}O_{14}P_4$: 472.95; found: 473.00. $^1$H NMR (400 MHz, CDOD) 7.28-7.12 (m, 5H), 5.75-5.65 (m, 1H), 3.20 (q, J=7.4, 6H), 2.77 (t, J=7.5, 2H), 2.06-1.95 (m, 2H), 1.30 (t, J=7.4, 9H).

Example 14

1-(Di-tert-butoxyphosphoryl)oxy)-3-phenylpropyl acetate) (Compound 114)

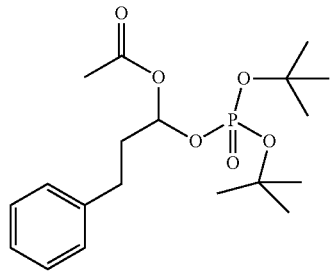 [SMILES: CC(=O)OC(CCc1ccccc1)OP(=O)(OC(C)(C)C)OC(C)(C)C]

Compound 114 was prepared according to the general procedure of Scheme V from 1-chloro-3-phenylpropyl acetate and di-tert-butyl tetrabutylamonium phosphate. [2M+H]+ calcd for $C_{38}H_{62}O_{12}P_2$: 773.37; found: 773.0.

Example 15

Tetraphenyl (3-phenylpropane-1,1-diyl) bis(phosphate) (Compound 115)

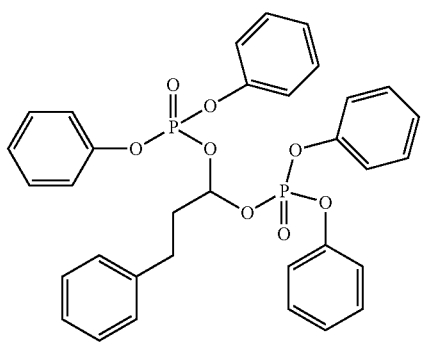 [SMILES: O=P(Oc1ccccc1)(Oc1ccccc1)OC(CCc1ccccc1)OP(=O)(Oc1ccccc1)Oc1ccccc1]

Compound 115 was prepared according to the general procedure of Scheme V from 1,1-diiodo-3-phenylpropane and diphenyl silver phosphate. [M+H]+ calcd for $C_{33}H_{30}O_8P_2$: 617,14; found: 616.90. $^1$H NMR (300 MHz, CDCl$_3$) 7.40-7.03 (m, 25H ), 6.48-6.40 (m, 1H), 2.66-2.60 (m, 2H), and 2.24-2.15 (m, 2H).

Example 16

Tetraethyl (3-phenylpropane-1, 1-diyl) bis(phosphate) (Compound 116)

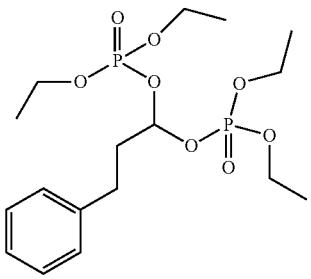 [SMILES: CCOP(=O)(OCC)OC(CCc1ccccc1)OP(=O)(OCC)OCC]

Compound 116 was prepared according to the general procedure of Scheme V from 1,1-diiodo-3-phenylpropane and diethyl silver phosphate, [M+H]$^+$ calcd for $C_{17}H_{30}O_8P_2$: 424,14; found: 424.3. $^1$H NMR (400 MHz, CD$_3$OD) 7.71 (dd, J=6.0 and 3.6, 1H), 7.61 (t, J=3.6, 1H), 7.30-7.21 (m, 3H), 5.95-5.89 (m, 1H), 4.22-4.13 (m, 8H), 2.78 (t, J=7.8, 2H), 1.74-1.67 (m, 2H), and 1.34-1,25 (m, 12H).

Example 17

((4,5-cis)-2-((Z)-Heptadec-8-en-1-yl)-1,3-dioxolane-4,5-diyl)dimethanol (Compound 117)

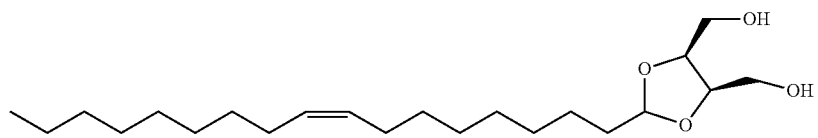 [SMILES: CCCCCCCC/C=C\CCCCCCCC1O[C@@H](CO)[C@@H](CO)O1]

Compound 117 was prepared according to the general procedure of Scheme VI from (Z)-9-octadecenal and meso-erythritol. $^1$H NMR (400 MHz, CDCl$_3$) 5.37 (bs, 2H), 4.55 (t, J=5.2, 1H), 4.18 (dd, J=10.8 and 5.2, 1H), 3.95-3.76 (m, 3H), 3.53-3.38 (m, 2H), 2.08-2.00 (m, 4H), 1.68-1.60 (m, 4H), 1.40-1.25 (m, 20H), and 0.91 (t, J=6.4, 3H).

Example 18

(Z)-(2-(Heptadec-8-en-1-yl)-1,3-dioxolan-4-yl)methanol (Compound 118)

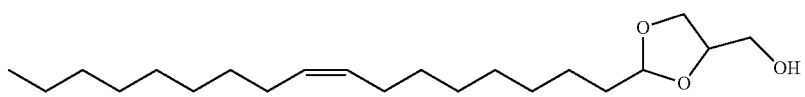 [SMILES: CCCCCCCC/C=C\CCCCCCCC1OCC(CO)O1]

Compound 118 was prepared as a mixture of stereoisomers according to the general procedure of Scheme VI from (Z)-9-octadecenal and glycerol. $^1$H NMR (400 MHz, CDCl$_3$) 3.37 (bs, 2H), 4.18-4.08 (m, 2H), 3.95-3.87 (m, 1H), 3.80-3.55 (m, 4H), 2.10-1.99 (m, 4H), 1.68-1.57 (m, 3H), 1.45-1.28 (m, 21H), and 0.91 (t, J=6.8, 3H).

Example 19

(Z)-(2-(Heptadec-8-en-1-yl)-1,3-dioxolan-4-yl)methyl dimethyl phosphate (Compound 119)

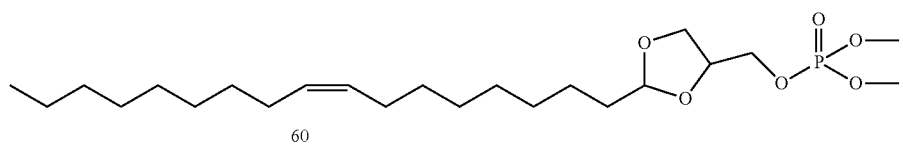

Compound 119 was prepared as a mixture of stereoisomers from Compound 118 and dimethyl chlorophosphate. $^1$H NMR (400 MHz, CDCl$_3$) 5.34-5.27 (m, 2H), 4.92 (t, J=4.2, 0.5H), 4.82 (t, J=4.2, 0.5H), 4.28-3.81 (m, 5H), 3.73 (s, 3H), 3.71 (s, 3H), 1.98-1.90 (m, 3H), 1.62-1.53 (m, 3H), 1.28-1.17 (m, 22H), and 0.81 (t, J=6.0, 3H).

Example 20

2-(Pyridin-3-yl)-1,3-dioxan-5-yl oleate (Compound 120) and (2-(pyridin-3-yl)-1,3-dioxolan-4-yl)methyl oleate (Compound 121)

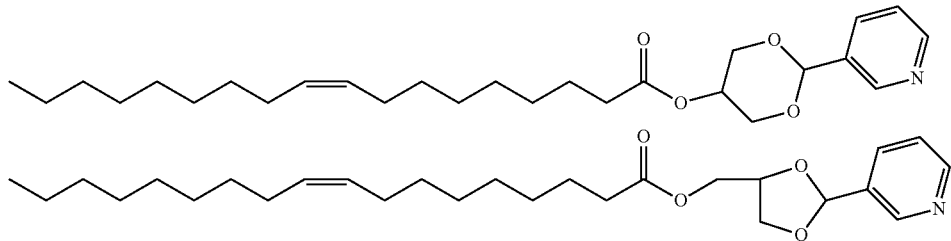

Compounds 120 and 121 were prepared as a mixture of stereoisomers from oleic acid, nicotinaldehyde, and glycerol. Briefly, nicotinaldehyde was condensed with glycerol in the presence of an acid catalyst to afford a mixture of 5-member-ring and 6-member-ring acetals that were treated with oleic chloride to form the corresponding ester Compounds 120 and 121. [M+H]$^+$ calcd for $C_{27}H_{43}NO_4$: 446.32; found: 446.4. $^1$H NMR (400 MHz, CDCl$_3$) 8.66-8.54 (m, 2H), 7.94 (t, J=10, 1H), 7.46 (bs, 1H), 5.99 (s, 0.5H), 5.87 (s, 0.5H), 5.33 (bs, 2H ), 4.55-3.81 (m, 5H), 2.40-2.25 (m, 2H), 2.02 (bs, 4H), 1.70-1.55 (m, 2H), 1.28-1.17 (m, 20H), and 0.88 (t, J=6.0, 3H).

Example 21

N-(5,5-Dimethyl-2-oxido-1,3,2-dioxaphosphinan-2-yl)oleamide (Compound 122)

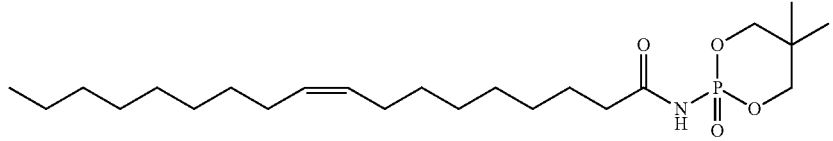 [SMILES: CCCCCCCC/C=C\CCCCCCCC(=O)NP1(=O)OCC(C)(C)CO1]

Compound 122 was prepared from oleic acid, 2,2-dimethylpropane-1,3-diol, diol, and phosphorus oxychloride. Briefly, 2,2-dimethylpropane-1,3-diol was treated with phosphorus oxychloride to form the corresponding cyclic chlorophosphate that was then reacted with oleic amide to provide Compound 122, [M+H]$^+$ calcd for $C_{23}H_{44}NO_4P$: 430.30; found: 430.6. $^1$H NMR (400 MHz, CD$_3$OD) 5.35 (bs, 2H), 4.40 (d, J=10, 2 H), 4.01 (dd, J=20 and 10, 2H), 2.38-2.02 (m, 4H), 1.65-1.56 (m, 2H), 1.38-1.25 (m, 22H), and 0.92 (t, J=7.2, 3H),

Example 22

N-(5,5-Dimethyl-2-oxido-4-phenyl-13,2-dioxaphosphinan-2-yl)oleamide (Compound 123)

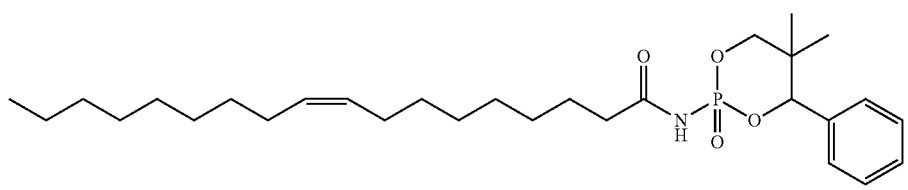 [SMILES: CCCCCCCC/C=C\CCCCCCCC(=O)NP1(=O)OCC(C)(C)C(c2ccccc2)O1]

Compound 123 was prepared as a mixture of stereoisomers from oleic acid, 2,2-dimethyl-1-phenylpropane-1,3-diol, and phosphorus oxychloride in a reaction sequence same as that of Compound 122. [M+H]$^+$ calcd for $C_{29}H_{48}NO_4P$: 506.33; found: 506.4. $^1H$ NMR (400 MHz, CDCl$_3$) 8.52 (d, J=10.4, 1H), 7.35-7.30 (m, 5H), 5.82 (s, 1H), 5.28 (bs, 2H), 4.84 (d, J=10, 1H), 3.92 (dd, J=23 and 10, 1H), 2.32-2.26 (m, 2H), 1.96-1.89 (m, 4H), 1.60-1.53 (m, 2H), 1.30-1.15 (m, 20H), 1.04 (s, 3H), 0.82 (t, J=6.8, 3H), and 0.76 (s, 3H).

Example 23

1-((5,5-Dimethyl-2-oxido-4-phenyl-1,3,2-dioxaphosphinan-2-yl)oxy)ethyl oleate (Compound 124)

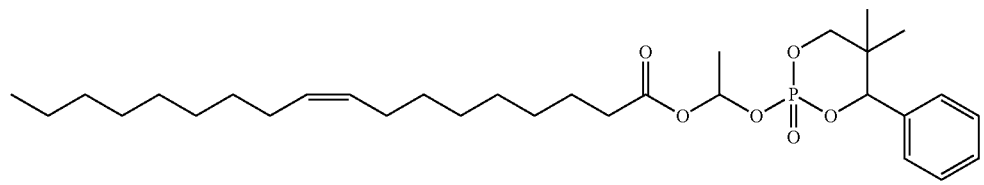 [SMILES: CCCCCCCC/C=C\CCCCCCCC(=O)OC(C)OP1(=O)OCC(C)(C)C(c2ccccc2)O1]

Compound 124 was prepared as a mixture of stereoisomers from oleic acid, 2,2-dimethyl-1-phenylpropane-1,3-diol, and phosphorus oxychloride. Briefly, oleic acid was converted to the acid chloride with treatment of oxalyl chloride in dichloromethane and then the oleic chloride was treated with paraldehyde and zinc chloride in acetonitrile at 60-65° C. to give 1-chloroethyl oleate. The oleate was then reacted with 2-chloro-5,5-dimethyl-4-phenyl-1,3,2-dioxaphosphinane 2-oxide prepared from 2,2-dimethyl-1-phenyl-propane-1,3-diol, and phosphorus oxychloride to afford Compound 124 as the final product after chromatography purification. [M+Na]$^+$ calcd for $C_{31}H_{51}O_6P$: 573.33; found: 573.4. $^1H$ NMR (400 MHz, CDCl$_3$) 7.32-7.17 (m, 5H), 6.67-6.61 (m, 1H), 5.37 (s, 1H), 5.28 (bs, 2H), 4.39 (d, J=10.8, 1H), 3.89 (ddd, J=24, 11.8, and 3.6, 1H), 2.32-2.26 (m, 2H), 1.96-1.89 (m, 3H), 1.60-1.50 (m, 5H), 1.26-1.12 (m, 21H), 0.95 (d, J=8.8, 3H), 0.81 (t, J=6.8, 3H), and 0.73 (s, 314H).

BIOLOGICAL EXAMPLES

Examples of use of the method include the following. It will be understood that the following are examples and that the embodiments are not limited to these examples.

Example A

In Vitro Activation of Prodrug Analogues by Rat Liver Microsomes, Quantification by LC-MS/MS Prodrug compounds are tested for activation to the active drug in reactions catalyzed by the microsomal fraction of rat liver,
Methods:

Prodrug compounds are tested for activation by liver microsomes isolated from rats induced with dexamethasone to enhance CYP3A,4 activity. Reactions are conducted in 0.1 M KH$_2$PO$_4$, pH 7.4, in the presence of 2 mM NADPH and liver microsomes (1 mg/mL). Reaction mixtures are incubated for 5 min, in an Eppendorf Thermomixer 5436 (37°C., speed 6). Reactions are terminated by the addition of 1.5 volumes of methanol. The resulting extracts are clarified by centrifugation at 14,000 rpm in an Eppendorf microfuge (20 min.). The supernatants (200 µL) are evaporated under vacuum and heat to dryness. The dried residue is reconstituted with 200 µL of water and the mixture is centrifuged for 10 min at 14,000 rpm. A mixture of 35 µL aliquot of supernatant and 35 µL of mobile phase A is analyzed by LC-MS/MS. The active compound is detected by using MS/MS mode and quantified based on comparison to a standard active compound.

Example B

Active compound Accumulation in Hepatocytes Following Incubation with Prodrug Compounds Prodrug compounds are evaluated for their ability to generate active compounds in freshly isolated rat hepatocytes.
Methods:

Hepatocytes are prepared from fed Sprague-Dawley rats (250-300 g) according to the procedure of Berry and Friend (Berry, M. N. Friend, D. S., J. Cell Biol. 43:506-520 (1969)) as modified by Groen (Groen, A. K. et al., Eur. J. Biochem 122:87-93 (1982)). Hepatocytes (20 mg/mL wet weight, >85% trypan blue viability) are incubated at 37° C. in 2 mL of Krebs-bicarbonate buffer containing 20 mM glucose, and 1 mg/mL BSA for 2 h in the presence of 1-250 µM a prodrug compound (from 25 mM stock solutions in DMSO). Following the incubation, 1600 µL aliquot of the cell suspension is centrifuged and 300 µL of acetonitrile is added to the pellet, vortexed and sonicated until the pellet broke down. Then 200 µL of water is added to make a 60% acetonitrile solution. After 10 min centrifugation at 14,000 rpm, the resulting supernatant is transferred to a new vial and evaporated to near dryness in a Savant SpeedVac Plus at room temperature. The dried residue is reconstituted with 200 µL of water and the mixture was centrifuged for 10 min at 14,000 rpm. A mixture of 35 µL aliquot of supernatant and 35 µL of mobile phase A (20 mM N—N-dimethylhexylamine and 10 mM propionic acid in 20% methanol) is analyzed by LC-MS/MS. The active compound is detected by using MS/MS mode (M–/78.8) and quantified based on comparison to a standard active compound.

Example C

Tissue Distribution Following Oral Administration of Active Compounds and their Prodrugs The liver specificity of prodrugs is compared relative to their parent active compound in liver and other organs that could be targets of toxicity, Methods:

Nucleoside analogues and their prodrugs are administered at 5-20 mg/kg to fasted rats by oral gavage. Plasma and portal vein concentrations of the active and prodrug are determined by HPLC-UV, and the liver, skeletal muscle, cardiac, kidney, small intestine, and other organ concentrations are measured by LC-MS using the standard chromatography method. The results demonstrate the liver targeting of the prodrug compounds and provide evidence for improved safety of the prodrugs over that of the actives. This can occur solely by the liver targeting provided by the prodrug.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15°, 10°, 5°, 3°, 1°, 0.1°, or otherwise. Similarly, in certain embodiments, the terms "generally perpendicular" and "substantially perpendicular" refer to a value, amount, or characteristic that departs from exactly perpendicular by less than or equal to 15°, 10°, 5°, 3°, 1°, 0.1°, or otherwise.

The above description discloses several methods and materials. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A compound of Formula I:

(I)

wherein:
- $R^1$ and $R^2$ are each independently selected from the group consisting of H, M, an optionally substituted $C_1$-$C_6$ alkyl, an optionally substituted $C_1$-$C_6$ alkyloxy, an optionally substituted $C_1$-$C_6$ acyloxy, an optionally substituted aryl, and an optionally substituted heteroaryl;
- $R^3$ is selected from the group consisting of H and an optionally substituted $C_1$-$C_6$ alkyl; or $R^3$ optionally forms an optionally substituted ring with $R^2$; or $R^3$ together with $R^2$ form a methylene or =CRR'; or $R^3$ together with $R^2$ form an oxo (=O) or =NR";
- M is a biological agent or a prodrug of a biological agent; wherein the biological agent is selected from the group consisting of:
  - a nucleoside antiviral or nucleoside anticancer agent;
  - a HMG-CoA reductase inhibitor, a selective thyroid hormone receptor modulator, a peroxisome proliferator-activated receptor modulator, a fibrate, a nicotinic acid, a bile acid, an omega-3 fatty acid;
  - a glucose modulator;
  - a peroxisome proliferator-activated receptor modulator, a glucose biosynthesis inhibitor, a dipeptidyl peptidase 4 inhibitor; and
  - a nuclear hormone receptor modulator;
- X is $OR^4$;
- Y and Y' are each O;
- Z is selected from the group consisting of O, $NR^5$, $CR^8R^6$, C=O, C=$NR^7$, and null; or Z is a 2-5 atom spacer selected from an optionally substituted $C_1$-$C_6$ alkyl, an optionally substituted $C_1$-$C_6$ alkyloxy, and an optionally substituted $C_1$-$C_6$ heteroalkyl;
- $R^4$ is selected from the group of H, an optionally substituted $C_1$-$C_6$ alkyl, and an optionally substituted $C_1$-$C_6$ heteroalkyl;
- $R^5$ is selected from the group consisting of H, M, an optionally substituted $C_1$-$C_6$ alkyl, an optionally substituted $C_1$-$C_6$ heteroalkyl, and an optionally substituted $C_1$-$C_6$ acyl;
- $R^6$ is selected from the group consisting of F, Cl, and an optionally substituted $C_1$-$C_6$ alkyl; or $R^6$ is H provided that $R^1$ or $R^2$ or $R^8$ is connected to a cyclic core carbon atom through an oxygen-carbon (O—C) bond;
- $R^7$ is selected from the group consisting of H, an optionally substituted $C_1$-$C_6$ alkyl, and an optionally substituted $C_1$-$C_6$ heteroalkyl;
- $R^8$ is selected from the group consisting of F, Cl, M, and an optionally substituted $C_1$-$C_6$ alkyl; or $R^8$ is H provided that $R^1$ or $R^2$ is connected to a cyclic core carbon atom through an oxygen-carbon (O—C) bond;
- R and R' are each independently selected from the group consisting of an optionally substituted $C_1$-$C_6$ alkyl, an optionally substituted $C_2$-$C_6$ alkenyl, and M; and
- R" is selected from the group consisting of H, $C_1$-$C_6$ alkyl, $C_1$-$C_6$ alkoxyl, and $C_1$-$C_6$ alkylamino;

provided that at least one of $R^1$, $R^2$, $R^5$, and $R^8$ is M;

or a stereoisomer or a pharmaceutically acceptable salt thereof.

2. A compound of Formula Ib or Ic:

(Ib)

-continued

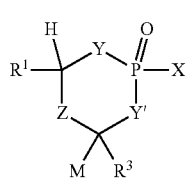

(Ic)

wherein:
$R^1$ is selected from the group consisting of H, an optionally substituted $C_1$-$C_6$ alkyl, an optionally substituted aryl, and an optionally substituted heteroaryl;
$R^2$ and $R^3$ are each independently selected from the group consisting of H and an optionally substituted $C_1$-$C_6$ alkyl; or $R^2$ and $R^3$ optionally form an optionally substituted ring; or $R^2$ and $R^3$ optionally form a methylene or =CRR'; or $R^2$ and $R^3$ optionally form an oxo (=O) or =NR";
M is a biological agent or a prodrug of a biological agent; wherein the biological agent is selected from the group consisting of:
  a nucleoside antiviral or nucleoside anticancer agent;
  a HMG-CoA reductase inhibitor, a selective thyroid hormone receptor modulator, a peroxisome proliferator-activated receptor modulator, a fibrate, a nicotinic acid, a bile acid, an omega-3 fatty acid;
  a glucose modulator;
  a peroxisome proliferator-activated receptor modulator, a glucose biosynthesis inhibitor, a dipeptidyl peptidase 4 inhibitor; and
  a nuclear hormone receptor modulator;
X is $OR^4$;
Y and Y' are each independently O;
Z is selected from the group consisting of O, $NR^5$, $CR^8R^6$, C=O, C=$NR^7$, and null; or Z is a 2-5 atom spacer selected from an optionally substituted $C_1$-$C_6$ alkyl, an optionally substituted $C_1$-$C_6$ alkyloxy, an optionally substituted $C_1$-$C_6$ heteroalkyl, and an optionally substituted aryl;
$R^4$ is selected from the group consisting of H, an optionally substituted $C_1$-$C_6$ alkyl, and an optionally substituted $C_1$-$C_6$ heteroalkyl;
$R^5$ is selected from the group consisting of H, an optionally substituted $C_1$-$C_6$ alkyl, an optionally substituted $C_1$-$C_6$ heteroalkyl, and an optionally substituted $C_1$-$C_6$ acyl;
$R^6$ is selected from the group consisting of F, Cl, and an optionally substituted $C_1$-$C_6$ alkyl; or $R^6$ is H provided that $R^1$ or $R^2$ or $R^8$ is connected with the cyclic core carbon atom through an oxygen-carbon (O—C) bond;
$R^7$ is selected from the group consisting of H, an optionally substituted $C_1$-$C_6$ alkyl, and an optionally substituted $C_1$-$C_6$ heteroalkyl;
$R^8$ is selected from the group consisting of F, Cl, M, and an optionally substituted $C_1$-$C_6$ alkyl; or $R^8$ is H provided that $R^1$ or $R^2$ is connected to a cyclic core carbon atom through an oxygen-carbon (O—C) bond;
R and R' are each independently selected from the group consisting of an optionally substituted $C_1$-$C_6$ alkyl, an optionally substituted $C_2$-$C_6$ alkenyl, and M; and
R" is selected from the group consisting of H, $C_1$-$C_6$ alkyl, $C_1$-$C_6$ alkoxyl, and $C_1$-$C_6$ alkylamino;
or a stereoisomer or a pharmaceutically acceptable salt thereof.

3. A compound of Formula III:

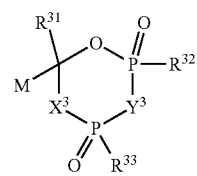

(III)

wherein:
$R^{31}$ is H; or $R^{31}$ optionally forms a bond with M or $X^3$ when $X^3$ is N;
$R^{32}$ and $R^{33}$ are each independently selected from the group consisting of Cl, OH, $NH_2$, an optionally substituted $C_1$-$C_6$ alkyl, an optionally substituted $C_1$-$C_6$ alkyloxy, and an optionally substituted $C_1$-$C_6$ alkylamino;
M is a biological agent or a prodrug of a biological agent;
  wherein the biological agent is selected from the group consisting of:
    a nucleoside antiviral or nucleoside anticancer agent;
    a lipid modulator;
    a HMG-CoA reductase inhibitor, a selective thyroid hormone receptor modulator, a peroxisome proliferator-activated receptor modulator, a fibrate, a nicotinic acid, a bile acid, an omega-3 fatty acid;
    a glucose modulator;
    a peroxisome proliferator-activated receptor modulator, a glucose biosynthesis inhibitor, a dipeptidyl peptidase 4 inhibitor; and
    a nuclear hormone receptor modulator;
$X^3$ is O or $NR^{34}$;
$Y^3$ is selected from the group consisting of O, $NR^{34}$, and an optionally substituted $C_1$-$C_6$ alkyl;
$R^{34}$ is selected from the group consisting of H, an optionally substituted $C_1$-$C_6$ alkyl, and an optionally substituted $C_1$-$C_6$ heteroalkyl;
or a stereoisomer or a pharmaceutically acceptable salt thereof.

4. A compound selected from the group consisting of:

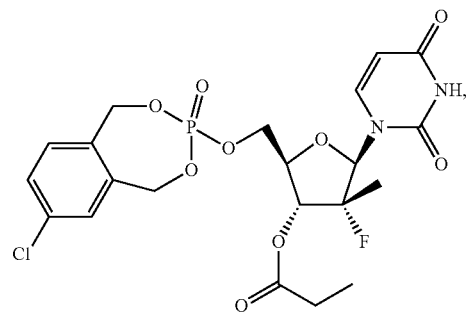

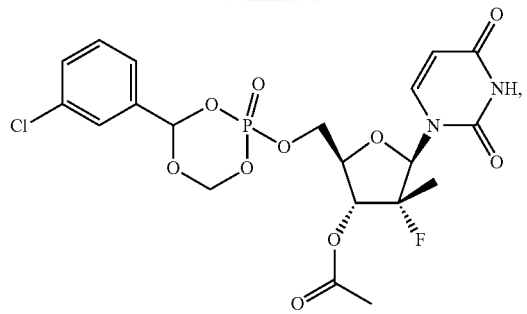

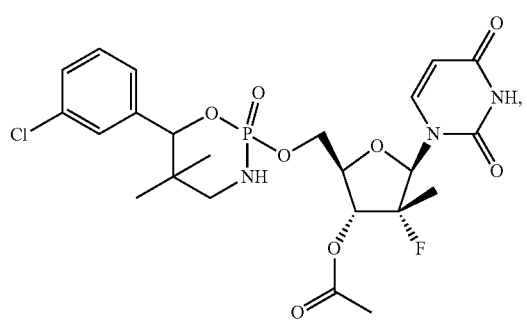

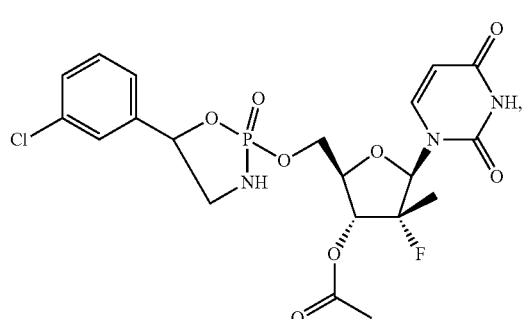

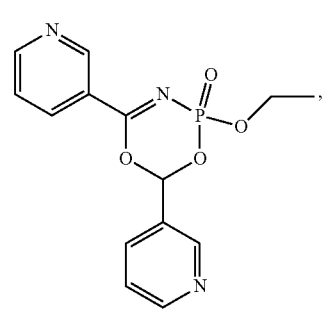

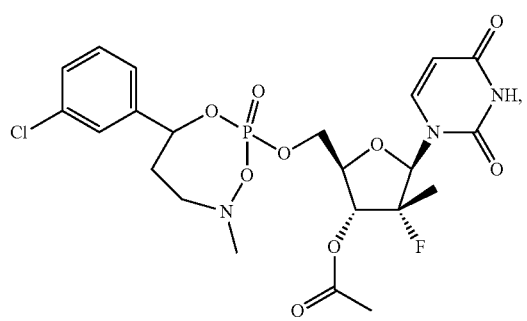

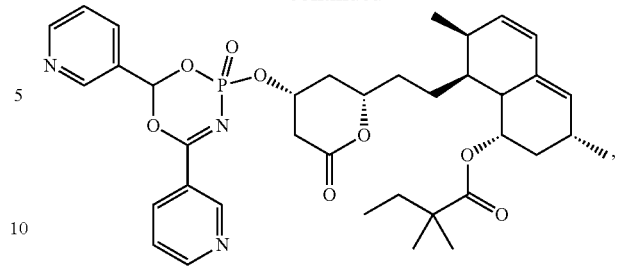

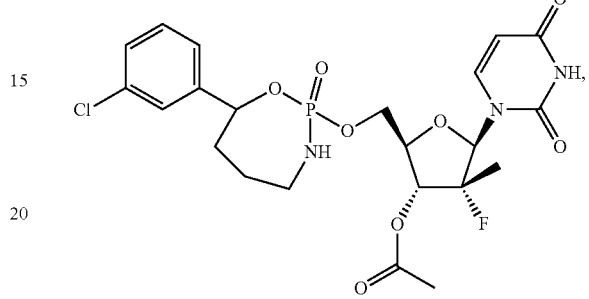

or a stereoisomer or a pharmaceutically acceptable salt thereof.

5. A pharmaceutical composition comprising the compound of claim 1 and a pharmaceutically acceptable excipient.

6. A method of treating a disease, disorder or condition comprising administering an effective amount of the compound of claim 1 to a subject in need thereof;
wherein the disease, disorder or condition is a disease, disorder or condition of the liver.

7. The method of claim 6, wherein the disease, disorder or condition is a metabolic, cardiovascular or hormonal disease in which the liver is involved in the production and/or the homeostasis control of the biochemical end products of the disease, disorder or condition.

8. The method of claim 6, wherein the disease, disorder or condition is selected from the group consisting of hepatitis, liver cancer, liver fibrosis, fatty liver, malaria, viral infection, parasitic infection, diabetes, hyperlipidemia, atherosclerosis, obesity, dyslipidemia, hyperglycemia and a hormonal condition.

9. A pharmaceutical composition comprising the compound of claim 1 and a pharmaceutically acceptable excipient.

10. A method of treating a disease, disorder or condition comprising administering an effective amount of the compound of claim 4 to a subject in need thereof;
wherein the disease, disorder or condition is a disease, disorder or condition of the liver.

11. The method of claim 10, wherein the disease, disorder or condition is a metabolic, cardiovascular or hormonal disease in which the liver is involved in the production and/or the homeostasis control of the biochemical end products of the disease, disorder or condition.

12. The method of claim 10, wherein the disease, disorder or condition is selected from the group consisting of hepatitis, liver cancer, liver fibrosis, fatty liver, malaria, viral infection, parasitic infection, diabetes, hyperlipidemia, atherosclerosis, obesity, dyslipidemia, hyperglycemia and a hormonal condition.

* * * * *

UNITED STATES PATENT AND TRADEMARK OFFICE
CERTIFICATE OF CORRECTION

PATENT NO. : 10,449,210 B2  
APPLICATION NO. : 15/118821  
DATED : October 22, 2019  
INVENTOR(S) : Lin Zhi Page 1 of 11

It is certified that error appears in the above-identified patent and that said Letters Patent is hereby corrected as shown below:

On the Title Page

On Page 4, Column 1, Item (56), Line 1, under Other Publications, delete "Modifictions" and insert --Modifications--.

On Page 4, Column 1, Item (56), Line 4, under Other Publications, delete "Diasteroselectivity" and insert --Diastereoselectivity--.

On Page 4, Column 1, Item (56), Line 15, under Other Publications, delete "Arznemittelforschung." and insert --Arzneimittelforschung.--.

On Page 4, Column 1, Item (56), Line 17, under Other Publications, delete "dioxphospholane" and insert --dioxaphospholane--.

On Page 4, Column 1, Item (56), Line 37, under Other Publications, delete "γ" and insert --β--.

On Page 4, Column 1, Item (56), Line 46, under Other Publications, delete "Syntheis" and insert --Synthesis--.

On Page 4, Column 1, Item (56), Line 48, under Other Publications, delete "Phosphoalkyl" and insert --Phosphonoalkyl--.

On Page 4, Column 1, Item (56), Line 52, under Other Publications, delete "Frutofuranoses" and insert --Fructofuranoses--.

On Page 4, Column 1, Item (56), Line 55, under Other Publications, delete "Gluthione" and insert --Glutathione--.

On Page 4, Column 1, Item (56), Line 61, under Other Publications, delete "Pyrophossphate" and insert --Pyrophosphate--.

Signed and Sealed this  
Fourth Day of August, 2020

Andrei Iancu  
*Director of the United States Patent and Trademark Office*

On Page 4, Column 1, Item (56), Line 64, under Other Publications, delete "Diposphate" and insert --Diphosphate--.

On Page 4, Column 1, Item (56), Line 68, under Other Publications, delete "diamiopurine" and insert --diaminopurine--.

On Page 4, Column 2, Item (56), Line 26, under Other Publications, delete "mehtyl" and insert --methyl--.

On Page 4, Column 2, Item (56), Line 39, under Other Publications, delete "Cyclis" and insert --Cyclo--.

On Page 4, Column 2, Item (56), Line 43, under Other Publications, delete "Diasteromeric" and insert --Diastereomeric--.

On Page 4, Column 2, Item (56), Line 47, under Other Publications, delete "oxazapphosphorinanes" and insert --oxazaphosphorinanes--.

On Page 4, Column 2, Item (56), Lines 58-59, under Other Publications, delete "Parenchyman" and insert --Parenchyma--.

On Page 4, Column 2, Item (56), Line 61, under Other Publications, delete "fasciclue" and insert --fascicule--.

On Page 4, Column 2, Item (56), Line 63, under Other Publications, delete "Prologation" and insert --Prolongation--.

On Page 4, Column 2, Item (56), Line 66, under Other Publications, delete "Phospolipids" and insert --Phospholipids--.

On Page 5, Column 1, Item (56), Line 10, under Other Publications, delete "Hydroxgyclophosphamide" and insert --Hydroxycyclophosphamide--.

On Page 5, Column 1, Item (56), Line 28, under Other Publications, delete "Ocfostate" and insert --Ocfosfate--.

On Page 5, Column 1, Item (56), Line 29, under Other Publications, delete "non-Hodgkins's" and insert --non-Hodgkin's--.

On Page 5, Column 1, Item (56), Line 63, under Other Publications, delete "Esthers" and insert --Esters--.

On Page 5, Column 1, Item (56), Line 64, under Other Publications, delete "Reation" and insert --Reaction--.

CERTIFICATE OF CORRECTION (continued)
U.S. Pat. No. 10,449,210 B2

On Page 5, Column 2, Item (56), Line 2, under Other Publications, delete "Arylphoshonate" and insert --Arylphosphonate--.

On Page 5, Column 2, Item (56), Line 10, under Other Publications, delete "Cycophosphamide" and insert --Cyclophosphamide--.

On Page 5, Column 2, Item (56), Line 14, under Other Publications, delete "Chemotheraputic" and insert --Chemotherapeutic--.

On Page 5, Column 2, Item (56), Line 16, under Other Publications, delete "chemptherapy" and insert --chemotherapy--.

On Page 5, Column 2, Item (56), Lines 27-28, under Other Publications, delete "Activiation" and insert --Activation--.

On Page 5, Column 2, Item (56), Line 32, under Other Publications, delete "carbontlates" and insert --carboxylates--.

On Page 5, Column 2, Item (56), Line 42, under Other Publications, delete "Oxathiaphosphrinan" and insert --Oxathiaphosphorinan--.

On Page 5, Column 2, Item (56), Line 69, under Other Publications, delete "Coumpounds" and insert --Compounds--.

On Page 6, Column 1, Item (56), Line 6, under Other Publications, delete "Efficiacy" and insert --Efficacy--.

On Page 6, Column 1, Item (56), Line 6, under Other Publications, delete "Diplvoxil" and insert --Dipivoxil--.

On Page 6, Column 1, Item (56), Line 13, under Other Publications, delete "Phosphomomethyl" and insert --Phosphonomethyl--.

On Page 6, Column 1, Item (56), Line 34, under Other Publications, delete "Glutathlone" and insert --Glutathione--.

On Page 6, Column 1, Item (56), Line 47, under Other Publications, delete "Identifcation" and insert --Identification--.

On Page 6, Column 1, Item (56), Line 56, under Other Publications, delete "Tiophosphates" and insert --Thiophosphates--.

On Page 6, Column 1, Item (56), Line 59, under Other Publications, delete "Enkephalinas" and insert --Enkephalinase--.

On Page 6, Column 1, Item (56), Line 60, under Other Publications, delete "Erwme" and insert --Enzyme--.

On Page 6, Column 1, Item (56), Line 61, under Other Publications, delete "Aadenine" and insert --Adenine--.

On Page 6, Column 1, Item (56), Line 62, under Other Publications, delete "Cynthesis" and insert --Synthesis--.

On Page 6, Column 2, Item (56), Line 21, under Other Publications, delete "Diasteroselective" and insert --Diastereoselective--.

On Page 6, Column 2, Item (56), Line 52, under Other Publications, delete "y1" and insert --yl--.

On Page 6, Column 2, Item (56), Line 65, under Other Publications, delete "Acyloxymethyyl" and insert --Acyloxymethyl--.

On Page 6, Column 2, Item (56), Line 65, under Other Publications, delete "Pyridmidenc" and insert --Pyrimidine--.

On Page 6, Column 2, Item (56), Line 71, under Other Publications, delete "famiciclovir" and insert --famciclovir--.

On Page 7, Column 1, Item (56), Line 8, under Other Publications, delete "alpha" and insert --δ--.

On Page 7, Column 1, Item (56), Line 10, under Other Publications, delete "Organosphosphates" and insert --Organophosphates--.

On Page 7, Column 1, Item (56), Line 13, under Other Publications, delete "Seletive" and insert --Selective--.

On Page 7, Column 1, Item (56), Line 49, under Other Publications, delete "Nucelear" and insert --Nuclear--.

On Page 7, Column 1, Item (56), Line 53, under Other Publications, delete "tetracmgenated" and insert --tetraoxygenated--.

On Page 7, Column 2, Item (56), Line 2, under Other Publications, delete "Monophospates" and insert --Monophosphates--.

On Page 7, Column 2, Item (56), Line 44, under Other Publications, delete "Alkenoy1" and insert --Alkenoyl--.

On Page 7, Column 2, Item (56), Line 52, under Other Publications, delete "fluorouride" and insert --fluorouridine--.

CERTIFICATE OF CORRECTION (continued)
U.S. Pat. No. 10,449,210 B2

On Page 8, Column 1, Item (56), Line 17, under Other Publications, delete "Guaninylalkl" and insert --Guaninylalkyl--.

On Page 8, Column 1, Item (56), Line 28, under Other Publications, delete "VII. 1)" and insert --VII.--.

On Page 8, Column 1, Item (56), Line 29, under Other Publications, delete "N3" and insert --$N^3$--.

On Page 8, Column 1, Item (56), Line 62, under Other Publications, delete "Hydroxycylophosphamide" and insert --Hydroxycyclophosphamide--.

On Page 8, Column 2, Item (56), Line 25, under Other Publications, delete "Hapatology" and insert --Hepatology--.

On Page 9, Column 1, Item (56), Line 18, under Other Publications, delete "proposy)" and insert --propoxy--.

On Page 9, Column 1, Item (56), Line 24, under Other Publications, delete "dechlorethylation" and insert --dechloroethylation--.

On Page 9, Column 1, Item (56), Line 28, under Other Publications, delete "activiated" and insert --activated--.

On Page 9, Column 1, Item (56), Line 48, under Other Publications, delete "Diasteroselectivity" and insert --Diastereoselectivity--.

On Page 9, Column 1, Item (56), Line 57, under Other Publications, delete "Stercochemical" and insert --Stereochemical--.

On Page 9, Column 2, Item (56), Line 10, under Other Publications, delete "Mutagenisis" and insert --Mutagenesis--.

On Page 9, Column 2, Item (56), Line 20, under Other Publications, delete "Effeciently" and insert --Efficiently--.

On Page 10, Column 1, Item (56), Line 20, under Other Publications, delete "Snthesis" and insert --Synthesis--.

On Page 10, Column 1, Item (56), Lines 21-22, under Other Publications, delete "Phosphopepties" and insert --Phosphopeptides--.

On Page 10, Column 1, Item (56), Line 43, under Other Publications, delete "Cucloadditions" and insert --Cycloadditions--.

On Page 10, Column 1, Item (56), Line 51, under Other Publications, delete "phosphatidylhydrcwhomochoLine" and insert --phosphatidylhydroxyhomochoLine--.

CERTIFICATE OF CORRECTION (continued)
U.S. Pat. No. 10,449,210 B2

On Page 10, Column 1, Item (56), Line 54, under Other Publications, delete "Deriviates" and insert --Derivatives--.

On Page 10, Column 1, Item (56), Line 54, under Other Publications, delete "Dihydorzy" and insert --Dihydroxy--.

On Page 10, Column 2, Item (56), Line 4, under Other Publications, delete "dichlorophospates" and insert --dichlorophosphates--.

On Page 10, Column 2, Item (56), Line 50, under Other Publications, delete "Clinincal" and insert --Clinical--.

On Page 10, Column 2, Item (56), Line 63, under Other Publications, delete "Activc" and insert --Active--.

On Page 11, Column 1, Item (56), Line 19, under Other Publications, delete "Japanes" and insert --Japanese--.

On Page 11, Column 1, Item (56), Line 21, under Other Publications, delete "Sythesis" and insert --Synthesis--.

On Page 11, Column 1, Item (56), Line 35, under Other Publications, delete "Vescicles" and insert --Vesicles--.

On Page 11, Column 1, Item (56), Lines 37-38, under Other Publications, delete "Toxixity" and insert --Toxicity--.

On Page 11, Column 1, Item (56), Line 43, under Other Publications, delete "Cobald" and insert --Cobalt--.

On Page 11, Column 1, Item (56), Line 46, under Other Publications, delete "acetaminopen" and insert --acetoaminophen--.

On Page 11, Column 1, Item (56), Line 53, under Other Publications, delete "Evalution" and insert --Evaluation--.

On Page 11, Column 2, Item (56), Line 16, under Other Publications, delete "Homochrial" and insert --Homochiral--.

On Page 11, Column 2, Item (56), Line 20, under Other Publications, delete "Systhesis" and insert --Synthesis--.

On Page 11, Column 2, Item (56), Line 52, under Other Publications, delete "Appproach" and insert --Approach--.

On Page 11, Column 2, Item (56), Line 70, under Other Publications, delete "destruktiv-selektive Oxidation" and insert --destruktiv-Oxidation--.

On Page 12, Column 1, Item (56), Line 11, under Other Publications, delete "Dialkyphosphonamidates" and insert --Dialkylphosphonamidates--.

On Page 12, Column 2, Item (56), Line 36, under Other Publications, delete "Adophosphamide" and insert --Aldophosphamide--.

On Page 12, Column 2, Item (56), Line 62, under Other Publications, delete "758" and insert --768--.

In the Specification

In Column 1, Line 33, delete "2014 ," and insert --2014,--.

In Column 1, Line 53, delete "art," and insert --art.--.

In Column 3, Line 35, delete "agent:" and insert --agent;--.

In Column 3, Line 65, delete "$R^8$ and" and insert --$R^8$, and--.

In Column 4, Line 13, delete "wherein;" and insert --wherein:--.

In Column 5, Line 9, delete "$NR,^5$" and insert --$NR^5$--.

In Column 5, Line 52, delete "methnylene" and insert --methylene--.

In Column 5, Line 67, delete "heteroalkyl:" and insert --heteroalkyl;--.

In Column 6, Line 44, delete "NR" and insert --$NR^5$--.

In Column 6, Lines 56-61, delete " " and insert -- --. 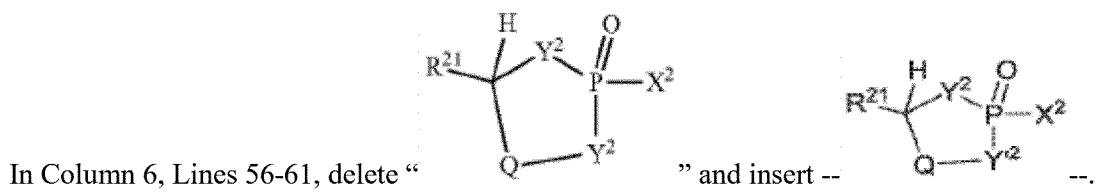

In Column 7, Line 13, delete "$N(R,^{24})_2$" and insert --$N(R^{24})_2$--.

In Column 7, Lines 25-33, delete " " and insert -- --. 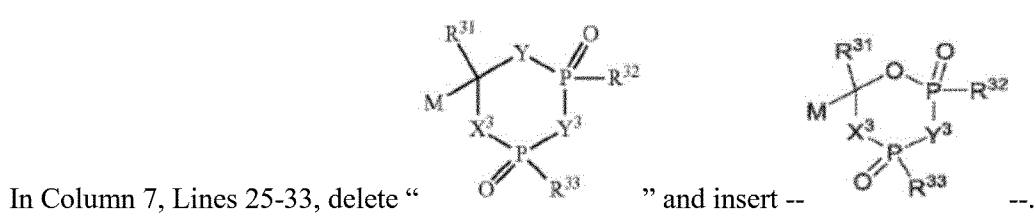

CERTIFICATE OF CORRECTION (continued)
U.S. Pat. No. 10,449,210 B2

In Column 7, Line 36, delete "N:" and insert --N;--.

In Column 7, Line 44, delete "$N^{34}$" and insert --$NR^{34}$--.

In Column 7, Line 64, delete "N:" and insert --N;--.

In Column 7, Line 66, delete "$C(O)NR^{48}$ ," and insert --$C(O)NR^{48}$,--.

In Column 8, Line 5, delete "hereroalkyl" and insert --heteroalkyl--.

In Column 8, Line 13, delete "o:" and insert --of--.

In Column 9, Lines 2-3, delete "heterocycle:" and insert --heterocycle;--.

In Column 9, Line 13, delete "agent:" and insert --agent;--.

In Column 11, Lines 25-33, delete " 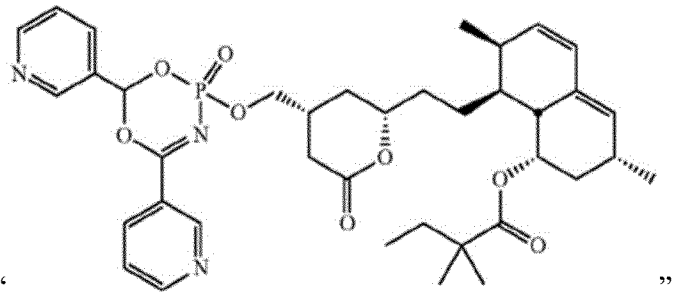 " and insert -- 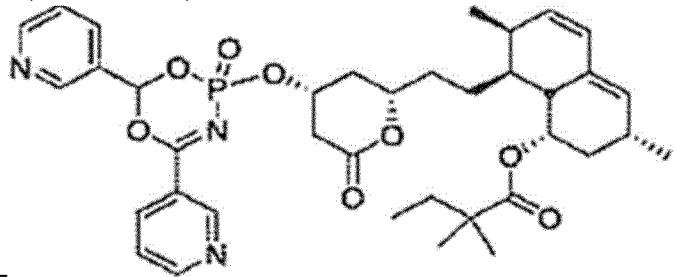 --.

In Column 11, Line 58, delete "embodiments." and insert --embodiments,--.

In Column 13, Line 61, delete "C $_1$-C$_6$" and insert --$C_1$-$C_6$--.

In Column 17, Lines 22-23, delete "N(R $^{24}$)$_2$" and insert --$N(R^{24})_2$--.

In Column 17, Line 27, delete "$NR_{24}$" and insert --$NR^{24}$--.

In Column 18, Line 33, delete "$R_{50}$" and insert --$R^{50}$--.

In Column 18, Line 34, delete "R $^{48}$" and insert --$R^{48}$--.

In Column 19, Line 60, delete "$R^{63}$, and $R^{64}$, $R^{65}$" and insert --$R^{63}$, $R^{64}$, and $R^{65}$--.

CERTIFICATE OF CORRECTION (continued)
U.S. Pat. No. 10,449,210 B2

In Column 21, Line 63, delete "mammalian," and insert --mammalian.--.

In Column 21, Line 64, delete "human," and insert --human.--.

In Column 22, Line 25, delete "limiting," and insert --limiting.--.

In Column 22, Line 50, delete "aralkyl;" and insert --aralkyl,--.

In Column 22, Line 50, delete "heterocycloalkyl;" and insert --heterocycloalkyl,--.

In Column 22, Line 61, delete "tower" and insert --lower--.

In Column 22, Line 66, delete "alkyl.," and insert --alkyl,--.

In Column 23, Line 9, delete "heteroalkyl;" and insert --heteroalkyl,--.

In Column 23, Line 19, delete "W" and insert --R'--.

In Column 23, Line 27, delete "haloalkyl," and insert --haloalkyl--.

In Column 23, Line 48, delete "to $NR_2$" and insert --to the $NR_2$--.

In Column 24, Line 21, delete "1,24-thiadiazole" and insert --1,2,4-thiadiazole--.

In Column 25, Line 2, delete "ring," and insert --ring.--.

In Column 25, Lines 9-10, delete "limiting," and insert --limiting--.

In Column 27, Lines 1-2, delete "7,666,85.5" and insert --7,666,855--.

In Column 28, Line 34, delete "tale." and insert --talc.--.

In Column 29, Lines 17-18, delete "crytallization" and insert --crystallization--.

In Column 33, Line 14, delete "methyl)" and insert --oxy)methyl)--.

In Column 34, Line 5, delete "12" and insert --2--.

In Column 34, Line 32, delete "3H," and insert --3H)--.

In Column 34, Line 60, delete "ethan-l-ol," and insert --ethan-1-ol--.

In Column 34, Line 61, delete "derivative," and insert --derivative.--.

In Column 34, Line 61, delete "11" and insert --H--.

In Column 34, Line 62, delete "14" and insert --H--.

In Column 34, Line 64, delete "314" and insert --3H--.

In Column 34, Line 64, delete "1111" and insert --1H--.

In Column 34, Line 66, delete "9bs," and insert --(9bs,--.

In Column 34, Line 66, delete "3.1_4" and insert --3.14--.

In Column 35, Line 42 (Approx.), delete "butan-l-ol" and insert --butan-1-ol--.

In Column 35, Line 43 (Approx.), delete "derivative," and insert --derivative.--.

In Column 36, Line 25, delete "butan-l-ol" and insert --butan-1-ol--.

In Column 36, Lines 54-55, delete "dioxadiphospinane" and insert --dioxadiphosphinane--.

In Column 37, Line 33, delete "pyrophosphate," and insert --pyrophosphate.--.

In Column 37, Line 36, delete "1,95" and insert --1.95--.

In Column 37, Line 43, delete "(Hydroxy" and insert --((Hydroxy--.

In Column 37, Line 65, delete "6:52" and insert --6.52--.

In Column 38, Line 16, delete "11.3" and insert --113--.

In Column 38, Line 20, delete "CDOD" and insert --CD$_3$OD--.

In Column 38, Line 21, delete "6 H" and insert --6H--.

In Column 38, Line 25, delete "(Di" and insert --((Di--.

In Column 38, Line 65, delete "617,14" and insert --617.14--.

In Column 40, Line 3, delete "phosphate," and insert --phosphate.--.

In Column 40, Line 4, delete "424,14" and insert --424.14--.

In Column 40, Line 7, delete "1,25" and insert --1.25--.

In Column 41, Line 45, after "diol," delete "diol,".

In Column 41, Line 49, delete "122," and insert --122.--.

In Column 41, Line 51, delete "2 H" and insert --2H--.

In Column 41, Line 53, delete "3H)," and insert --3H).--.

In Column 41, Line 56, delete "13" and insert --1,3--.

In Column 43, Line 46 (Approx.), delete "314H" and insert --3H--.

In Column 43, Line 58, delete "Microsomes," and insert --Microsomes.--.

In Column 43, Line 63, delete "liver," and insert --liver.--.

In Column 43, Line 67, delete "CYP3A,4" and insert --CYP3A4--.

In Column 44, Line 3, delete "min," and insert --min.--.

In Column 44, Line 67, delete "toxicity," and insert --toxicity.--.